United States Patent [19]

Yasuhiro et al.

[11] Patent Number: 5,412,098
[45] Date of Patent: May 2, 1995

[54] QUINOLONE DERIVATIVE OR SALT THEREOF AND ANTIBACTERIAL CONTAINING THE SAME

[75] Inventors: Kuramoto Yasuhiro; Noda Shuichiro; Shinobu Maruyama; Shunso Hatono; Haruyo Mochizuki; Akira Yazaki, all of Hiroshima, Japan

[73] Assignees: Wakunaga Seiyaku Kabushiki Kaisha; Fujisawa Pharmaceutical Co., Ltd., both of Osaka, Japan

[21] Appl. No.: 104,137

[22] PCT Filed: Dec. 25, 1992

[86] PCT No.: PCT/JP92/01712

§ 371 Date: Aug. 19, 1993

§ 102(e) Date: Aug. 19, 1993

[87] PCT Pub. No.: WO93/13091

PCT Pub. Date: Aug. 7, 1993

[30] Foreign Application Priority Data

Dec. 27, 1991 [JP] Japan .................. 3-346577

[51] Int. Cl.$^6$ .............. C07D 471/04; C07D 471/02; A61K 31/435; A61K 31/41
[52] U.S. Cl. .................... 546/156; 546/123
[58] Field of Search ............ 546/123, 156; 514/300, 514/312

[56] References Cited

U.S. PATENT DOCUMENTS

| | | | |
|---|---|---|---|
| 4,617,308 | 10/1986 | Mich et al. | 514/312 |
| 5,137,892 | 8/1992 | Chu et al. | 514/278 |
| 5,153,203 | 10/1992 | Yatsunami et al. | 514/312 |
| 5,245,037 | 9/1993 | Kuramoto et al. | 546/156 |

FOREIGN PATENT DOCUMENTS

| | | |
|---|---|---|
| 54-132582 | 10/1979 | Japan . |
| 61-251667 | 11/1986 | Japan . |
| 62-33176 | 2/1987 | Japan . |
| 2-85255 | 3/1990 | Japan . |

*Primary Examiner*—C. Warren Ivy
*Assistant Examiner*—D. Margaret M. Mach
*Attorney, Agent, or Firm*—Oblon, Spivak, McClelland, Maier & Neustadt

[57] ABSTRACT

A quinolone derivative represented by the below-described formula (1), or a salt thereof:

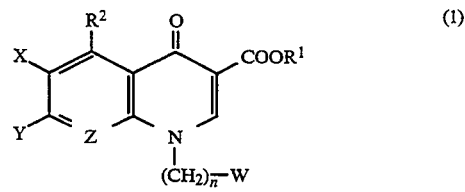

wherein $R^1$ represents a hydrogen atom, or a carboxyl protective group, $R^2$ represents a hydrogen atom, halogen atom or a lower alkyl group, X represents a hydrogen atom or a halogen atom, Y represents a halogen atom, a cyclic amino group which may have a substituent, a cyclo- lower alkenyl group which may have a substituent, or a group $R^3$—$(CH_2)_m$—A— (wherein $R^3$ represents a hydrogen atom or an amino group which may have a substituent, A represents an oxygen atom or a sulfur atom and m represents a number of 0 to 3), Z represents a nitrogen atom or a group C—$R^4$ (wherein $R^4$ represents a hydrogen atom or a halogen atom), W represents a five-membered heterocyclic group which may have a substituent and which has 3 or more heteroatoms, among which at least 2 hetero-atoms are nitrogen atoms, and n represents a number of 0 to 2; and an antibacterial agent containing the compounds.

Since the above-mentioned compounds exhibit excellent antibacterial activities and are highly safe, they are useful as pharmaceuticals for the human and animals, medicines for fishes, pesticides, preservatives for foods, and the like.

4 Claims, No Drawings

QUINOLONE DERIVATIVE OR SALT THEREOF AND ANTIBACTERIAL CONTAINING THE SAME

This application is a 371 of PCT/JP 92/01712, filed Dec. 25, 1992.

TECHNICAL FIELD

The present invention relates to novel quinolone derivatives and salts thereof having excellent antibacterial activity and oral-route absorption, and antibacterial agents containing the compounds.

BACKGROUND ART

Among the compounds which have pyridonecarboxylic acid as a basic skeleton, many are known to be useful as synthetic antibacterial agents due to their excellent antibacterial activities and a broad antibacterial spectrum. Mention may be given to norfloxacin (Japanese Patent Application Kokai No. 141286/1978), enoxacin (Japanese Patent Application Kokai No. 31042/1980), ofloxacin (Japanese Patent Application Kokai No. 46986/1982), cyprofloxacin (Japanese Patent Application Kokai No. 76667/1983) and the like, which have widely found a clinical utility as therapeutic agents for infectious diseases.

These compounds, however, are not sufficiently satisfactory in terms of antibacterial activities, intestinal tract absorption, metabolic stability, minimized adverse side effects, and the like, and hence novel compounds which meet these requirements have been desired.

Under the above circumstances, the present inventors have conducted careful studies with a view toward obtaining clinically excellent synthetic antibacterial agents, and have found that the compounds represented by formula (1) described hereinafter provide excellent oral absorption, exhibit excellent antibacterial activities against gram negative and gram positive bacteria and thus are very useful as synthetic antibacterial agents, leading to the completion of the invention.

DISCLOSURE OF THE INVENTION

The present invention is to provide quinolone derivatives represented by the below-described formula (1), salts thereof and antibacterial agents containing the derivatives or salts:

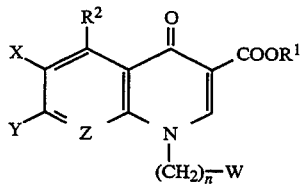

wherein $R^1$ represents a hydrogen atom, halogen atom or a carboxyl protective group, $R^2$ represents a hydrogen atom, halogen atom or a lower alkyl group, X represents a hydrogen atom or a halogen atom, Y represents a halogen atom, a cyclic amino group which may have a substituent, a cyclo- lower alkenyl group which may have a substituent, or a group $R^3$—$(CH_2)_m$—A—(- wherein $R^3$ represents a hydrogen atom or an amino group which may have a substituent, A represents an oxygen atom or a sulfur atom and m represents a number of 0 to 3), Z represents a nitrogen atom or a group C—$R^4$ (wherein $R^4$ represents a hydrogen atom or a halogen atom), W represents a five-membered heterocyclic group which may have a substituent and which has 3 or more hetero-atoms, among which at least 2 hetero-atoms are nitrogen atoms, and n represents a number of 0 to 2.

Since the present compounds (1) exhibit excellent antibacterial activities and are highly safe, they are useful as pharmaceuticals for the human and animals, medicines for fishes, pesticides, preservatives for foods, and the like.

BEST MODE FOR CARRYING OUT THE INVENTION

In the present invention, the term "lower" used in the expressions of the substituents of the quinolone derivatives or their salts (1) means that the group referred to has 1–7, preferably 1–5 carbon atoms when the substituents are linear or branched, and has 3–7 carbon atoms when the substituents are cyclic.

The carboxy protective group represented by $R^1$ is the ester residue of a carboxylic acid ester, and encompasses any groups which are relatively easily cleaved and produce corresponding free carboxyl groups. Examples of the carboxy protective group include those removable upon treatment under mild conditions such as hydrolysis or catalytic reduction, such as lower alkyl groups (e.g., methyl, ethyl, n-propyl, t-butyl, etc.), lower alkenyl groups (e.g., allyl, etc.), aralkyl groups (e.g., benzyl, etc.) or aryl groups (e.g., phenyl, etc.); and those readily removable in a living body, such as lower alkanoyloxy-lower alkyl groups (e.g., acetoxymethyl, pivaloyloxymethyl, etc.), lower alkoxycarbonyloxy-lower alkyl groups (e.g., methoxycarbonyloxymethyl, 1-ethoxycarbonyloxyethyl, etc.), lower alkoxymethyl groups (e.g. methoxymethyl, etc.), lactonyl groups (e.g., phthalidyl, etc.), di(lower alkyl)amino-lower alkyl groups (e.g., 1-dimethylaminoethyl, etc.), (5-methyl-2-oxo-1,3-dioxol-4-yl)methyl group, and the like.

Examples of lower alkyl groups represented by $R^2$ include methyl group, ethyl group, n-propyl group and t-butyl group.

Examples of halogen atoms represented by X and $R^2$ include a fluorine atom, chlorine atom, bromine atom, with a fluorine atom being preferred.

Halogen atoms represented by Y are the same as those represented by X, among which a fluorine atom and a chlorine atom are preferred.

Cyclic amino groups, represented by Y, which may have a substituent are saturated or unsaturated, and they may contain further one or more hetero-atoms such as nitrogen, oxygen, sulfur, etc., or a carbonyl carbon in the ring thereof. They may be mono, di, or tri-cyclic. Examples of such cyclic amino groups include: saturated or unsaturated monocyclic 3 to 7 membered cyclic amino groups having one nitrogen atom, such as azirydin-1-yl, azetidin-1-yl, pyrrolidin-1-yl, pyrrolin-1-yl, pyrrol-1-yl, dihydropyridin-1-yl, piperidino, dihydroazepin-1-yl, perhydroazepin-1-yl; saturated or unsaturated monocyclic 3 to 7 membered cyclic amino groups having two nitrogen atoms, such as imidazol-1-yl, imidazolidin-1-yl, imidazolin-1-yl, pyrazolidin-1-yl, piperazin-1-yl, 1, 4-dihydropyridin-1-yl, 1,2-dihydropyrimidin-1-yl, perhydropyrazin-1-yl and homopiperazin-1-yl; saturated or unsaturated monocyclic 3 to 7 membered cyclic amino groups having three or more nitrogen atoms, such as 1,2,4-triazole-1-yl, 1,2,3-triazole-1-yl, 1,2-dihydro-1,2,4-triazin-1-yl and perhydro-S-triazin-1-yl; saturated or unsaturated monocyclic 3 to 7 membered cyclic amino group which has a hetero-atom selected from the group consisting of nitrogen, oxygen and sulfur, as well as a nitrogen atom, such as oxazolidin-3-yl, isoxazolidin-2-yl, morpholino, 1,3-oxazin-3-yl, tiazolidin-1-yl, isotiazolidin-1-yl, thiomorpholin-1-yl, homothiomorpholin-1-yl, 1,2,4-thiadiazolin-2-yl, 1,2,3-thiadiazolidin-2-yl; saturated or unsaturated monocyclic cyclic amino groups of di or tri-cyclic, such as isoindolin-2-yl, indolin-1-yl, 1H-indazol-1-yl, purin-7-yl and tetrahydroquinolin-1-yl; and spiro or bridge type, saturated or unsaturated 5 to 12 membered cyclic amino groups, such as 2,8-diazaspiro[4,4]nonan-2-yl, 7-azabicyclo-[2.2.1]heptan-7-yl, 2,8-diazabicyclo-[4,3,0]nonane, 5-methyl-2,5-diazabicyclo[2.2.1]heptane and 2,5-diazabicyclo[2.2.1]heptane. Preferred examples of such cyclic amino groups are those represented by the following formulas (a)–(t):

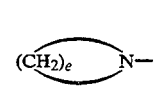 (a)

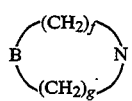 (b)

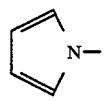 (c)

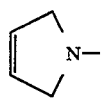 (d)

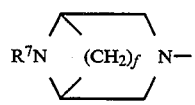 (e)

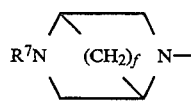 (f)

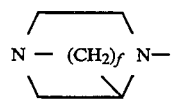 (g)

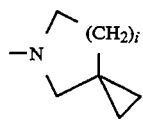 (h)

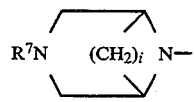 (i)

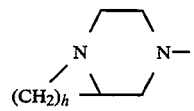 (j)

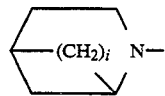 (k)

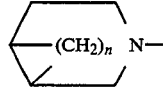 (l)

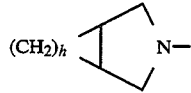 (m)

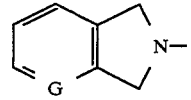 (n)

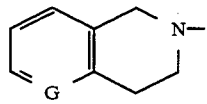 (o)

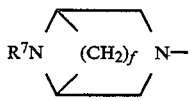 (p)

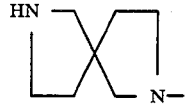 (q)

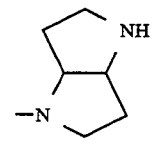 (r)

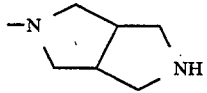 (s)

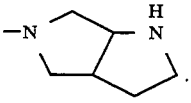 (t)

In the above formulas, E is an oxygen atom, a sulfur atom, $-NR^7$ or $-CONR^7$ ($R^7$ is a hydrogen atom, a hydroxyl group, a lower alkyl group, a cyclo- lower alkyl group, an aralkyl group, an alkenyl group, and acyl group or a hydroxy- lower alkyl group), G is CH or N, e is a number of 3–5, f is a number of 1–3, g is a number of 0–2 and h is 3 or 4, i is 1 or 2.

Cyclic atoms of these cyclic amino groups may be substituted with suitable substituents. Preferable examples of such substituents include lower alkyl groups, lower alkenyl groups, lower aralkyl groups, aryl groups, hydroxyl groups, hydroxy-lower alkyl groups, substituted or unsubstituted amino groups, substituted or unsubstituted amino- lower alkyl groups, cyclic amino groups as mentioned above, alkoxy groups, alkoxy- lower alkyl groups, halogen atoms, halo- lower alkyl groups, acyloxy groups, acyloxy- lower alkyl groups, acyl groups, carboxyl groups, carboxy- lower alkyl groups, alkoxycarbonyl- lower alkyl groups, mercapto groups, lower alkylthio groups, cyano groups and nitro groups.

Examples of the lower alkyl groups include methyl group and ethyl group, n-propyl group and the like. Examples of the lower alkenyl groups include vinyl group and allyl group and the like. Examples of the lower aralkyl groups include benzyl group and 1-phenylethyl group and the like. Examples of the aryl groups include phenyl group and the like. Examples of the hydroxy-lower alkyl groups include hydroxymethyl group, hydroxyethyl group, hydroxypropyl group and the like. Examples of the amino-lower alkyl groups include aminomethyl group, 1-aminoethyl group, 2-aminoethyl group, 1-amino-1-methylethyl group and the like. Examples of the alkoxy groups include methoxy group, ethyoxy group, n-propoxy group and the like. Examples of the alkoxy-lower alkyl groups include methoxymethyl group, ethoxymethyl group and the like. Examples of the halogen atoms include fluorine atom, chlorine atom, bromine atom and the like. Examples of the halo- lower alkyl groups include fluoromethyl group, trifluoromethyl group and the like. Examples of the acyloxy groups include acetoxy group, benzoyloxy group and the like. Examples of the acyloxy- lower alkyl groups include acetoxymethyl group benzoyloxymethyl group and the like. Examples of the acyl groups include lower alkanoyl group such as formyl, acetyl and the like, lower alkoxycarbonyl group such as methoxycarbonyl and ethoxycarbonyl, and aromatic acyl group such as benzoyl, phenoxycarbonyl, and the like. Examples of the carboxy- lower alkyl groups include carboxymethyl group, carboxyethyl group and the like. Examples of the alkoxycarbonyl- lower alkyl groups include methoxycarbonylmethyl group, t-butoxycarbonylmethyl group and the like. Examples of the lower alkylthio groups include methylthio group, ethylthio group and the like.

As the substituent of the substituted amino group and the substituted amino- lower alkyl group, there can be mentioned lower alkyl groups (e.g., methyl group, ethyl group, etc.), lower cycloalkyl groups (e.g., cyclopropyl group, cyclobutyl group, cyclopentyl group, etc.), lower alkenyl groups (e.g., vinyl group, ally group, etc.), lower aralkyl groups (e.g., benzyl group, 1-phenylethyl group, etc.), aryl groups (e.g., phenyl group, etc.), acyl groups (e.g., lower alkanoyl groups such as formyl and acetyl, lower alkoxycarbonyl groups such as methoxycarbonyl and ethoxycarbonyl, etc.), amino acid residues or peptide residues (e.g., glycyl-, leucyl-, valyl, alanyl-, phenylalanyl-, alanyl-alanyl, glycyl-valyl and glycyl-glycyl-valyl- groups, etc.), amino acid residues or peptide residues such as the above-described groups protected by a protection group such as acyl group, lower aralkyl group or the like commonly used in the peptide chemistry; and cyclic amino groups. The same or different kinds of 1 to 2 substituents can be freely selected. Compounds protected by the above-mentioned amino acid residues or peptide residues expectedly have an improved water-solubility.

Preferable examples of the substituted amino group and the substituted amino- lower alkyl group include methylamino group, ethylamino group, dimethylamino group, methylaminomethyl group, ethylaminomethyl group, dimethylaminomethyl group, glycyl-amino group, leucyl-amino group, valyl-amino group, alanyl-amino group, alanyl-alanyl-amino group and the like.

Regarding the groups represented by $R^7$, there are given methyl group, ethyl group or the like for the lower alkyl group; cyclopropyl group, cyclobutyl group or the like for the cyclo-lower alkyl group; benzyl group, 1-phenylethyl group or the like for the aralkyl group; vinyl group, allyl group or the like for the alkenyl group; formyl group, acetyl group, methoxycarbonyl group, ethoxycarbonyl group or the like for the acyl group; and hydroxymethyl group, hydroxyethyl group or the like for the hydroxy- lower alkyl group.

Among the cyclic amino groups represented by the formulas (a) and (b), those represented by the following formulas (a') and (b') are particularly preferred.

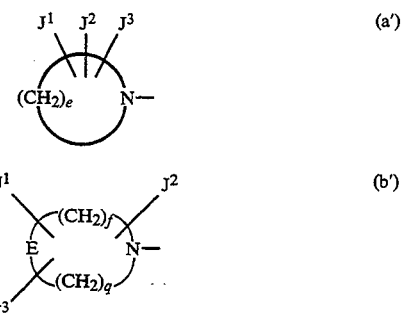

wherein E, e, f and g have the same meaning as defined for the formulas (a) and (b), $j^1$, $j^2$ and $j^3$ may be the same or different and are one of a hydrogen atom, a lower alkyl group, a lower alkenyl group, a lower aralkyl group, an aryl group, a hydroxyl group, a hydroxy-lower alkyl group, a amino group which may have a substituent, a amino- lower alkyl group which may have a substituent, a pyrrolidinyl group, a piperidino group, an azetidinyl group, an alkoxy group, an alkoxy- lower alkyl group, a halogen atom, a halo- lower alkyl group, an acyloxy group, an acyloxy- lower alkyl group, an acyl group, a carboxyl group, a carboxy- lower alkyl group, an alkoxycarbonyl- lower alkyl group, a mercapto group, a lower alkylthio group, a cyano group and nitoro group.

The definitions of substituents of the $j^1$, $j^2$ and $j^3$ and their preferable examples are the same as those described in relation to the substituents for the above-mentioned cyclic amino groups.

Examples of the heterocyclic ring groups represented by formula (a') include azetidinyl group, pyrrolidinyl group and piperidino group. Examples of the heterocyclic ring groups represented by formula (b') include piperazinyl group, morpholino group, thiomorpholino group, homopiperazinyl group, thiazolidinyl group, oxazolidinyl group and 3-oxo-1-piperazinyl group.

Particularly, preferable examples of groups represented by formulas (a') and (b') are as follows:
3-hydroxyazetidinyl group, 3-aminoazetidinyl group, 3-(N-t-butoxycarbonylamino)azetidinyl group, 3-acetylamino-azetidinyl group, 3-methylaminoazetidinyl group, 3-dimethyl-aminoazetidinyl group, 3-methylazetidinyl group, 3-amino-2-methylazetidinyl group; pyrrolidinyl group, 3-hydroxy- pyrrolidinyl group, 3,4-dihydroxypyrrolidinyl group, 3-methoxypyrrolidinyl group, 3-methylpyrrolidinyl group, 3-hydroxy-4-methyl-pyrrolidinyl group, 3-aminopyrrolidinyl group, 3-methylaminopyrrolidinyl group, 3-dimethylamino pyrrolidinyl group, 3-ethylaminopyrrolidinyl group, 3-diethylaminopyrrolidinyl group, 3-acetylaminopyrrolidinyl group, 3-t-butoxycarbonylaminopyrrolidinyl group, 3-(N-acetyl)methylaminopyrrolidinyl group, 3-(t-butoxy-carbonyl)methylaminopyrrolidinyl group, 3-amino-methylpyrrolidinyl group, 3-methylaminomethylpyrrolidinyl group, 3-dimethylaminomethylpyrrolidinyl group; 3-ethylaminomethylpyrrolidinyl group, 3-diethylaminomethylpyrrolidinyl group, 3-(N-acetyl)aminomethylpyrrolidinyl group, 3-(t-butoxycarbonyl)aminomethylpyrrolidinyl group, 3-(N-acetyl)methylaminomethylpyrrolidinyl group, 3-(t-butoxy-carbonyl)methylaminomethylpyrrolidinyl group, 3-(1-amino-ethyl)pyrrolidinyl group, 3-(2-aminoethyl)pyrrolidinyl group, 3-(1-amino-1-methylethyl)pyrrolidinyl group, 3-(1-methylaminoethyl)pyrrolidinyl group, 3-(1-dimethylamino-ethyl)pyrrolidinyl group; 3-amino-3-methylpyrrolidinyl group, 3-amino-4-methylpyrrolidinyl group, 3-amino-5-methylpyrrolidinyl group, 3-methylamino-4-methylpyrrolidinyl group, 3-dimethylamino-4-methylpyrrolidinyl group, 3-ethyl-amino-4-methylpyrrolidinyl group, 3-diethylamino-3-methylpyrrolidinyl group, 3-diethylamino-4-methylpyrrolidinyl group, 3-aminomethyl-4-methylpyrrolidinyl group, 3-methyl-aminomethyl-4-methylpyrrolidinyl group; 3-dimethylaminomethyl-4-methylpyrrolidinyl group, 3-ethyl-aminomethyl-4-methylpyrrolidinyl group, 3-(1-aminoethyl)-4-methylpyrrolidinyl group, 3-(2-aminoethyl)-4-methylpyrrolidinyl group, 3-amino-4-ethylpyrrolidinyl group, 3-methylamino-4-ethylpyrrolidinyl group, 3-dimethylamino-4-ethylpyrrolidinyl group, 3-ethylamino-4-ethylpyrrolidinyl group, 3-diethylamino-4-ethylpyrrolidinyl group, 3-aminomethyl-4-ethylpyrrolidinyl group, 3-methylaminomethyl-4-ethylpyrrolidinyl group; 3-dimethylaminomethyl-4-ethylpyrrolidinyl group; 3-amino-3-methylpyrrolidinyl group, 3-methylamino-3-methylpyrrolidinyl group, 3-dimethylamino-3-methylpyrrolidinyl group, 3-amino-3,4-dimethylpyrrolidinyl group, 3-amino-4,4-dimethylpyrrolidinyl group, 3-amino-4,5-dimethylpyrrolidinyl group, 3-amino-2,4-dimethylpyrrolidinyl group, 3-methylamino-3,4-dimethylpyrrolidinyl group; 2-methyl-3-aminopyrrolidinyl group, 2-methyl-3-dimethylaminopyrrolidinyl group, 3-amino-4-vinylpyrrolidinyl group, 3-amino-4-methoxypyrrolidinyl group, 3-amino-4-methoxymethylpyrrolidinyl group, 3-methylamino-4-methoxypyrrolidinyl group, 3-dimethylamino-4-methoxypyrrolidinyl group, 3-ethylamino-4-methoxypyrrolidinyl group, 3-dimethylamino-4-methoxypyrrolidinyl group; 3-benzylamino-4-methoxypyrrolidinyl group, 3-aminomethyl-4-methoxypyrrolidinyl group, 3-methylaminomethyl-4-methoxypyrrolidinyl group, 3-dimethylaminomethyl-4-methoxypyrrolidinyl group, 3-ethylaminomethyl-4-methoxypyrrolidinyl group, 3-aminomethyl-3-methoxypyrrolidinyl group, 3-methylaminomethyl-3-methoxypyrrolidinyl group, 3-dimethylaminomethyl-3-methoxypyrrolidinyl group, 3-amino-4ethoxypyrrolidinyl group, 3-methylamino-4-ethoxypyrrolidinyl group, 3-dimethylamino-4-ethoxypyrrolidinyl group, 3-methylamino-4-ethoxypyrrolidinyl group, 3-aminomethyl-4-ethoxypyrrolidinyl group, 3-dimethylaminomethyl-4-ethoxypyrrolidinyl group, 3-amino-4-aminocarbamoylpyrrolidinyl group, 3-amino-4-dimethylaminocarbamoylpyrrolidinyl group, 3-amino-4-hydroxypyrrolidinyl group, 3-amino-4-hydroxymethyl-pyrrolidinyl group, 3-amino-4-hydroxyethylpyrrolidinyl group; 3-amino-4-methyl-4-hydroxymethylpyrrolidinyl group, 3-aminomethyl-4-hydroxypyrrolidinyl group, 3-dimethylaminomethyl-4-hydroxypyrrolidinyl group, 3,4-dihydroxypyrrolidinyl group, 3,4-dimethoxypyrrolidinyl group, 3-hydroxy-4-methylpyrrolidinyl group, 3-amino-4-fluoropyrrolidinyl group, 3-amino-4-fluoromethylpyrrolidinyl group, 3-amino-4-trifluoromethylpyrrolidinyl group, 3-methylamino-4-fluoropyrrolidinyl group, 3-dimethylamino-4-fluoropyrrolidinyl group, 3-aminomethyl-4-fluoropyrrolidinyl group, 3-methylaminomethyl-4-fluoropyrrolidinyl group, 3-dimethylaminomethyl-4-fluoropyrrolidinyl group; 3-methylamino-4-chloropyrrolidinyl group; 3-aminomethyl-4-chloropyrrolidinyl group, 3-methylaminomethyl-4-chloropyrrolidinyl group, 3-(2-hydroxyethyl) aminomethylpyrrolidinyl group, 3-(2-fluoroethyl) aminometylpyrrolidinyl group, 3-amino-4-methylthiopyrrolidinyl group, 3-amino-4-methyl-sulfinylpyrrolidinyl group, 3-formimidoylaminopyrrolidinyl group, 3-(2-dimethylhydrazino)pyrrolidinyl group; 3-amino-4-methylenepyrrolidinyl group, 3-(t-butoxycarbonyl aminoacetyl)amino-4-methylpyrrolidinyl group, 3-aminoacetylamino-4-methylpyrrolidinyl group, 3-(2-aminopropanoyl)amino-4-methylpyrrolidinyl group, 3-(2-amino-3-phenylpropanoyl)amino-4-methylpyrrolidinyl group, 3-(2-benzyloxycarbonylamino-3-methylbutanoyl)amino-4-methylpyrrolidinyl group, 3-(2-amino-3-methylbutanoyl)amino-4-methylbutanoyl)amino-4-methylpyrrolidinyl group, 3-(2-amino-2-methylpropanoyl)amino-4-methylpyrrolidinyl group, 7-amino-5-azaspiro[2,4]heptan-5-yl group; piperazinyl group, 4-methylpiperazinyl group, 3-methylpiperazinyl group, 2-methylpiperazinyl group, 3,4-dimethylpiperazinyl group, 3,5-dimethylpiperazinyl group, 3,3-dimethylpiperazinyl group, 3,4,5-trimethylpiperazinyl group, 4-ethoxycarbonylpiperazinyl group, 4-t-butoxycarbonylpiperazinyl group, 4-acetylpiperazinyl group, 4-benzyloxycarbonylpiperazinyl group, 4-ethylpiperazinyl group, 3,4-diethylpiperazinyl group, 3,4,5-triethylpiperazinyl group, 4-ethyl-3,5-dimethylpiperazinyl group, 3-methyl-4-acetylpiperazinyl group, 3-methyl-4-t-butoxycarbonylpiperazinyl group, 4-benzylpiperazinyl group, 4-n-propylpiperazinyl group; 4-isopropylpiperazinyl group, 4-t-butylpiperazinyl group, 4-cyclopyperazinyl group, 4-cyclopentylpiperazinyl group, 4-cyclopropylmethylpiperazinyl group, 4-phenylpiperazinyl group, 4-(p-dimethylaminophenyl)piperazinyl group, 4-(p-methoxyphenyl)piperazinyl group, 4-(p-fluorophenyl)-piperazinyl group, 3-phenylpiperazinyl group, 3-(p-fluorophenyl)piperazinyl group, 3-(p-chlorophenyl)piperazinyl group, 3-(p-hydroxyphenyl)piperazinyl group, 3-(p-methylphenyl)-piperazinyl group, 4-hydroxyethylpiperazinyl group; 4-aminoethylpiperazinyl group, 4-allylpiperazinyl group, 4-cinnamylpiperazinyl group, 4-cyanoethylpiperazinyl group, 4-carboxyethylpiperazinyl group, 4-carboxymethylpiperazinyl group, 4-(1,2-dicarboxyethyl)piperazinyl group, 4-hydroxypiperazinyl group, 3-fluoromethylpiperazinyl group, 3-trifluoromethylpiperazinyl group, 4-formimidoylpiperazinyl group, 4-acetoimidoylpiperazinyl group; piperidino group, 4-amino piperidino group, 4-dimethylaminopiperidino group, 4-hydroxypiperidino group, morpholino group, 2-aminomethylmorpholino group, 2-methylaminomorpholino group, 2-dimethylaminomorpholino group, thiomorpholino group, homopiperazinyl group, 4- methylhomopiperazinyl group, thiazolidinyl group, and oxazolidinyl group.

Examples of the cyclo- lower alkenyl group represented by Y include unsaturated 5 to 7 membered aliphatic carbocyclic groups, such as cyclopentenyl group, cyclohexenyl group and cyclohexedienyl group. Examples of the cyclo- lower alkenyl groups represented by Y which may have a substituent include oxo-cyclohexenyl group, oxo-cyclopentenyl group, amino-cyclohexenyl group and amino-cyclopentenyl group, among which 3-oxo-cyclohexenyl group, 3-oxo-cyclopentenyl group, 3-aminocyclohexenyl group and 3-amino-cyclopentenyl group are preferred.

In case where Y is the group represented by the formula $R^3$—$(CH_2)_m$—A—, groups similar to those capable of substituting the cyclic amino group described above may be mentioned as substitutable groups among the amino groups of $R^3$ which may have a substituent.

In case where Z is the group represented by the formula C—$R^4$, the atoms similar to X may be mentioned as the halogen atoms represented by $R^4$, among which fluorine atom and chlorine atom are preferred.

Example of the five-membered heterocyclic group represented by W which has 3 or more hetero atoms, among which at least 2 hetero-atoms are nitrogen atoms include saturated or unsaturated five-membered heterocyclic group which has two nitrogen atoms and a hetero-atom selected from the group consisting of nitrogen, oxygen and sulfur. The heterocyclic group represented by W may be substituted with a suitable substituent such as amino group, above-mentioned substituted amino group, oxo group or the like. Preferable examples of such substituents are as follows:

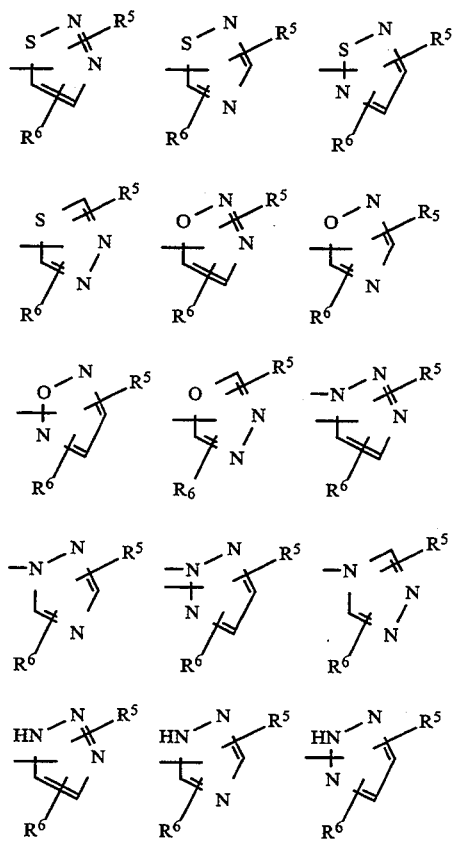

-continued

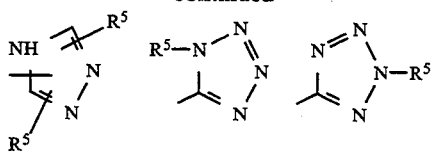

Examples of the two kinds of substituents $R^5$ and $R^6$ in W individually include a hydrogen atom, a lower alkyl group similar to $R^2$, and halo lower alkyl groups such as fluoromethyl trifluoromethyl and fluoroethyl.

Preferable examples of the group represented by W include: 1,2,3-thiadiazole-4-yl, 5-methyl-1,2,3-thiadiazole-4-yl, 1,3,4-thiadiazole-2-yl, 5-methyl-1,3,4-thiadiazole-2-yl, 5-trifluoromethyl-1,3,4-thiadiazole-2-yl, 1,2,3-thiadiazole-5-yl, 4-methyl-1,2,3-thiadiazole-5-yl, 1,2,4-thiadiazole-3-yl, 5-methyl-1,2,4-thiadiazole-3-yl, 1,2,4-thiadiazole-5-yl, 3-methyl-1,2,4-thiadiazole-5-yl, 1,2,5-thiadiazole-3-yl, 4-methyl-1,2,5-thiadiazole-3-yl, 4-fluoromethyl-1,2,5-thiadiazole-3-yl, 1,2,3-triazole-4-yl, 1-methyl-1,2,3-triazole-5-yl, 1,2,4-triazole-4-yl, 3-methyl-1,2,4-triazole-4-yl, 1,2,4-triazole-3-yl, 1-methyl-1,2,4-triazole-5-yl, 1-benzyl-1,2,4-triazole-3-yl, 1,2,4-triazole-5-yl, 2-methyl-1,2,4-triazole-5-yl, 2-benzyl-1,2,4-triazole-5-yl, 3,5-dimethyl-1,2,4-triazole-4-yl, 1,2,3-oxadiazole-4-yl, 5-methyl-1,2,3-oxadiazole-4-yl, 1,3,4-oxadiazole-2-yl, 5-methyl-1,3,4-oxadiazole-2-yl, 5-trifluoromethyl-1,3,4-oxadiazole-2-yl, 1,2,3-oxadiazole-5-yl, 4-methyl-1,2,3-oxadiazole-5-yl, 1,2,4-oxadiazole-3-yl, 5-methyl-1,2,4-oxadiazole-3-yl, 1,2,4-oxadiazole-5-yl, 3-methyl-1,2,4-oxadiazole-5-yl, 1,2,5-oxadiazole-3-yl, 4-methyl-1,2,5-oxadiazole-3-yl, tetrazole-5-yl, 1-methyl-tetrazole-5-yl, 2-methyl-tetrazole-5-yl, 1,2,5-thiadiazole-3-ylmethyl, and 1,2,3-thiadiazole-4-ylmethyl.

The quinolone derivatives or salts thereof of formula (1) can be converted into both of acid addition salts and base addition salts, and the salts include those forming chelate salts with boron compounds. Examples of acid addition salts include: (a) salts with mineral acids such as hydrochloric acid and sulfuric acid; (b) salts with organic carboxylic acids such as formic acid, citric acid, trichloroacetic acid, trifluoroacetic acid, fumaric acid and maleic acid; and (c) salts with sulfonic acids such as methanesulfonic acid, benzenesulfonic acid, p-toluensulfonic acid, mesitylenesulfonic acid and naphthalenesulfonic acid. On the other hand, examples of base addition salts include: (a') salts with alkali metals such as sodium and potassium; (b') salts with alkaline earth metals such as calcium and magnesium; (c') ammonium salts; and (d') salts with nitrogen-containing organic bases such as trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-beta-phenethylamine, 1-ephenamine and N,N'-dibenzylethylenediamine. Examples of boron compounds include boron halides such as boron fluoride, and lower acyloxy borons such as acetoxy boron, The quinolone derivatives or salts thereof of formula (1) may be not only in unsolvated forms but also in hydrated or solvated forms. The present invention therefore embraces the compounds (1) in any crystalline forms and their hydrated and solvated products.

The quinolone derivatives or salts thereof of formula (1) include those containing an asymmetric carbon atom which can exist as optically active substances. These optically active substances are also embraced in the compounds of the present invention. The compounds of formula (1) further include those containing two or more asymmetric carbon atoms which can exist as different stereoisomers (cis-form and trans-form). These stereoisomers are also included in the compounds of the present invention.

Each of the quinolone derivatives or salts thereof of formula (1) can be prepared by a process suited for the types of its substituent groups. Preferred preparation processes are as follows.

Process 1

Among the compounds represented by formula (1), those in which $R^1$ is a hydrogen atom or a lower alkyl group and Y is a halogen atom can be prepared, for example, by the series of steps shown in the following reaction scheme (1):

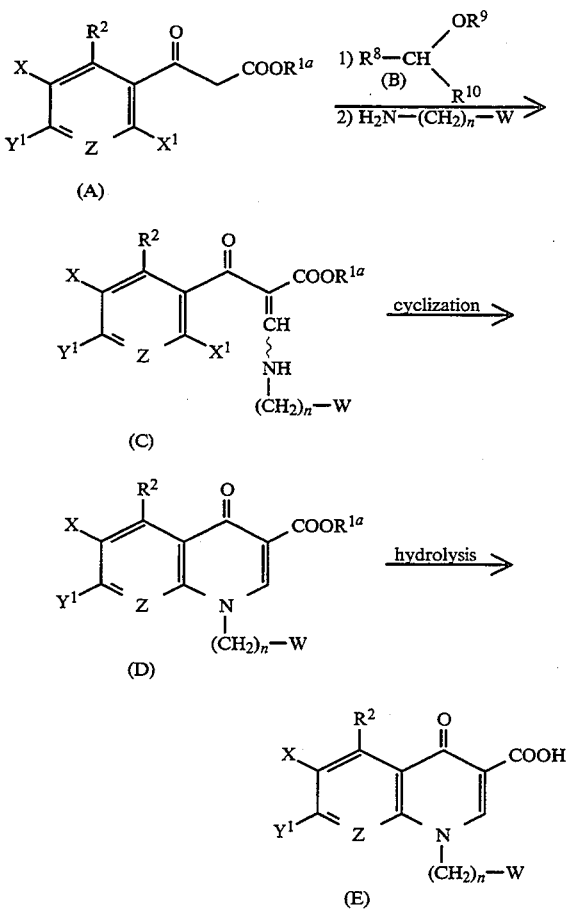

wherein $X^1$ and $y^1$ individually represent a halogen atom; $R^{1a}$ represents a lower alkyl group; $R^8$ represents a lower alkoxy group or a group

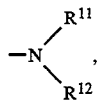

wherein $R^{11}$ and $R^{12}$ individually represent a lower alkyl group; $R^9$ and $R^{10}$ individually represent a lower alkyl group; and X, Z, W, $R^2$ and n have the same meaning as defined above.

Namely, the compound (C) can be obtained by reacting the compound (A) with an orthoformic acid ester (B) such as ethyl orthoformate or methyl orthoformate in acetic anhydride, and then reacting the resulting product with the compound $H_2N-(CH_2)_n-W$. The reaction between the compound (A) and the orthoformic acid ester is conducted generally at $0 \geq -160°$ C., preferably at $50°-150°$ C. The reaction time is generally from 10 minutes to 48 hours, preferably from 1 hour to 10 hours. The orthoformic acid ester (B) can be used in at least an equimolar amount, preferably in a molar amount about 1 to 10 times relative to the compound (A).

The subsequent reaction with the compound $H_2N-(CH_2)_n-W$ is conducted in a suitable solvent. Any solvent can be used here, as long as it does not affect the reaction. Examples of such solvents include: aromatic hydrocarbons such as benzene, toluene and xylene; ethers such as diethyl ether, tetrahydrofuran, dioxane, monoglyme and diglyme; aliphatic hydrocarbons such as pentane, hexane, heptane and ligroin; halogenated hydrocarbons such as methylene chloride, chloroform and carbon tetrachloride; dipolar aprotic solvents such as dimethylformamide and dimethylsulfoxide; and alcohols such as methanol, ethanol and propanol. This reaction is conducted generally at $0°-150°$ C., preferably at $0°-100°$ C. The reaction time generally ranges from 10 minutes to 48 hours. The compound $H_2N-(CH_2)_n-W$ can be used in at least an equimolar amount, preferably in a molar amount 1-2 times relative to the compound (A).

As an alternative, the compound (C) may be obtained by a reaction of the compound (A) with an acetal such as N,N-dimethylformamide dimethyl acetal or N,N-dimethylformamide diethyl acetal, followed by a reaction with the compound $H_2N-(CH_2)_n-W$. Any solvent may be used for the reaction with the acetal, as long as it is inert to the reaction. The abovementioned solvents can be used as such inert solvent. This reaction is conducted generally at $0°-150°$ C., preferably at room temperature to $100°$ C. The reaction time is generally from 10 minutes to 48 hours, preferably from 1 to 10 hours.

The compound (C) thus obtained is subjected to cyclization reaction to obtain compound (D). This reaction is conducted in a suitable solvent in the presence of a basic compound. Any solvent can be used for this reaction, as long as it does not affect the reaction. Examples of such solvents include: aromatic hydrocarbons such as benzene, toluene and xylene; ethers such as diethyl ether, tetrahydrofuran, dioxane and monoglyme; halogenated hydrocarbons such as methylene chloride, chloroform and carbon tetrachloride; alcohols such as methanol, ethanol, propanol and butanol; dipolar aprotic solvents such as dimethylformamide and dimethylsulfoxide. Preferable examples of basic compounds include: alkali metals such as metallic sodium and metallic potassium; metal hydrides such as sodium hydride and calcium hydride; inorganic bases such as sodium hydroxide, potassium hydroxide and sodium carbonate; alkoxides such as sodium methoxide, sodium ethoxide and potassium-t-butoxide; metal fluorides such as potassium fluoride and sodium fluoride; and organic bases such as triethylamine and 1,8-diazabicyclo [5.4.0]-undecene (DBU). This reaction is conducted generally at $0°-200°$ C., preferably from room temperature to $180°$ C. The reaction can be brought to completion usually in 5 minutes to 24 hours. The basic compound may be used in at least an equimolar amount, preferably in a molar amount 1-2 times relative to the compound (c).

If desired, the compound (D) thus obtained is further subjected to hydrolysis to obtain compound (E). This reaction can be conducted under reaction conditions which are employed in usual hydrolysis reactions. For example, the hydrolysis reaction is carried out in the presence of a basic compound such as sodium hydroxide, potassium hydroxide, sodium carbonate or potassium carbonate; a mineral acid such as hydrochloric acid, sulfuric acid or hydrobromic acid; or an organic acid such as p-toluenesulfonic acid, and in a solvent, e.g. water; an alcohol such as methanol, ethanol or propanol; an ether such as tetrahydrofuran or dioxane; a ketone such as acetone or methyl ethyl ketone; or an acetic acid; or a mixed solvent thereof. This reaction is conducted generally at room temperature to 180° C., preferably from room temperature to 140° C. The reaction time generally ranges from 1 hour to 24 hours.

Process 2

Among the compounds represented by formula (1), those in which $R^1$ is a hydrogen atom or a lower alkyl group; and Y is a cyclic amino group which may have a substituent, a cyclo lower alkenyl group which may have a substituent, or a group $R^3-(CH_2)_m-A-$, wherein $R^3$, A and m have the same meaning as defined above can be produced by the steps shown in the following reaction scheme (2):

Reaction Scheme (2):

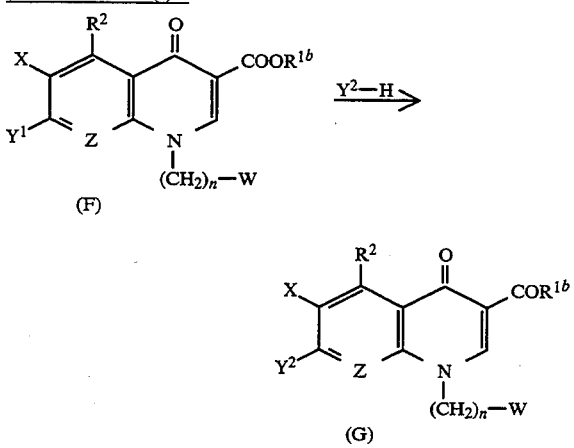

wherein $X^{1b}$ represents a halogen atom or a lower alkyl group, $y^2$ is a cyclic amino group which may have a substituent, a cyclo lower alkenyl group which may have a substituent or a group $R^3-(CH_2)_m-A-$, wherein $R^3$, A and m have the same meaning as defined above, and $R^2$, X, $Y^1$, W and n have the same meaning as defined above.

Namely, the compound (F) obtained in the process 1 is reacted with the compound represented by the formula $Y^2-H$ to obtain compound (G).

This reaction is carried out in a suitable solvent at room temperature to 160° C., if desired, in the presence of an acid-neutralizing agent such as sodium carbonate, calcium carbonate, sodium hydrogencarbonate, triethylamine or 1,8-diazabicyclo [5.4.0]-undecene (DBU). Examples of solvents which are usable in this reaction include: aromatic hydrocarbons such as benzene, toluene and xylene; alcohols such as methanol and ethanol; ethers such as tetrahydrofuran, dioxane and monoglyme; halogenated hydrocarbons such as methylene chloride, chloroform and carbon tetrachloride; dipolar aprotic solvents such as dimethylformamide and dimethylsulfoxide; and other solvents which do not adversely affect the reaction such as acetonitrile and pyridine. The reaction can generally be brought to completion in a few minutes to 48 hours, preferably from 10 minutes to 24 hours. The compound $Y^2-H$ may be used in at least an equimolar amount, preferably in a molar amount 1-5 times relative to the compound (F).

In cases where the $R^{1b}$ of the compound (G) is a lower alkyl group, the group may be substituted with a hydrogen atom by hydrolysis.

When the starting compounds used in the processes 1 and 2 contain one or more reactive groups which do not take part in the reactions, such as amino group, imino group, hydroxyl group, mercapto group or carboxyl group, these starting compounds may be used in a form with these groups being protected. In such case, the protective groups are removed in a general manner after the completion of the reaction. Any group can be used as the protective group, as long as it can be removed without destroying the structure of the compound of the present invention to be formed by the reaction. Groups usually employed in the chemical field of peptides, aminosaccharides and nucleic acids can be used.

The starting compound (A) can be prepared by one of the processes described in the following documents or by a similar process:

1) *J. Heterocyclic Chem.* 2.2, 1033 (1985)
2) *Liebigs Ann. Chem.* 29 (1987)
3) *J. Med. Chem.* 31, 911 (1988)
4) *J. Org. Chem.* 35, 930 (1970)
5) Japanese Patent Application Laid-open (Kokai) No. 246541/1987
6) Japanese Patent Application Laid-open (Kokai) No. 26272/1987
7) Japanese Patent Application Laid-open (Kokai) No. 145268/1988
8) *J. Med. Chem.* 29, 2363 (1986)
9) *J. Fluorin Chem.* 28, 361 (1985)
10) Japanese Patent Application Laid-open (Kokai) No. 198664/1988
11) Japanese Patent Application Laid-open (Kokai) No. 264461/1988
12) Japanese Patent Application Laid-open (Kokai) No. 104974/1988
13) European Patent Application No. 230948
14) Japanese Patent Application Laid-open (Kokai) No. 282384/1990
15) Japanese Kohyo Publication No. 502452/1991
16) *J. Het. Chem.* 27, 1609 (1990)

Process 3

Among the compounds represented by formula (1), those in which $R^1$ is a carboxy protective group can be prepared by the steps shown in the following reaction scheme (3):

Reaction Scheme (3):

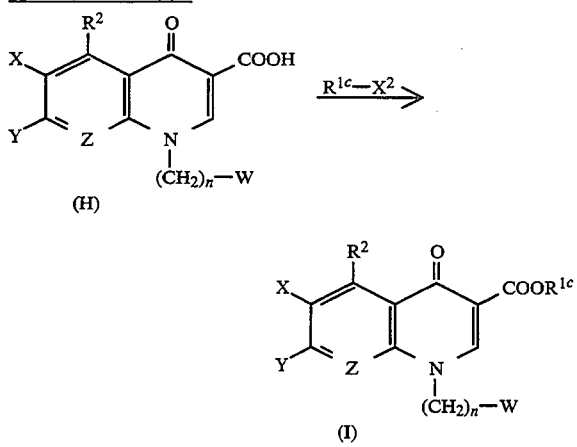

wherein $R^{1c}$ represents a carboxy protective group, $X^2$ represents a halogen atom, and $R^2$, X, Y, Z, W and n have the same meaning as defined above.

Compound (I) is obtained by reacting the compound (H) with the halogen compound $R^{1c}$—$X^2$. Examples of the preferred solvents include: aromatic hydrocarbons such as benzene and toluene; halogenated hydrocarbons such as methylene chloride and chloroform; dipolar aprotic solvents such as dimethylformamide and dimethyl sulfoxide; and other inactive solvents such as acetonitrile. The reaction is carried out at room temperature to 100° C. It is preferred that this reaction be carried out in the presence of a basic compound such as triethylamine, diisopropylethylamine, dicyclohexylamine, DBU, sodium carbonate, potassium carbonate or sodium hydroxide.

Among the compounds represented by the formula (1), those containing a primary or secondary amino group as heterocyclic group indicated by Y can be converted to the compounds which have a formimidoyl group or lower alkylimdoyl group on the amino group by reacting with formimidic acid ester or lower alkanecarboximidic acid ester.

The compounds of the present invention thus obtained are isolated and purified by methods known per se in the art. They are obtained in the form of salts, free carboxylic acids or free amines, depending on the conditions for isolation and purification. However, they can be converted mutually from one of these forms into another one, whereby the compounds of the present invention can be prepared in a desired form.

When the compounds (1) of the present invention are used as antibacterial agents, the compositions can be treated as compositions together with pharmaceutical allowable carriers for parenteral dosage such as injection, per rectum, eye instillation and the like and oral administration in the form of solid and solution.

Relating to the form of the composition for injection, pharmaceutical allowable axenic water or nonaqueous solution, suspension or emulsion and the like are give. As examples of appropriate nonaqueous carrier, diluent, solution or vehicle, propylene glycol, polyethylene glycol and vegetable oils such as olive oil and injectable organic esters including, for example, oleic acid ethyl are given. There compositions may include supplementary agents such as antiseptics, wetting agents, emulsifiers, dispersants and the like. The compositions, for example, can be sterilized by filtering with a bacteria holding filter or by mixing with a sterilizer in the form of an axenic solid composition soluble in sterilized water or other several sterilized injectable solutes or media right before the use.

The preparation for eye instillation dosage can preferably include dissolution adjuvants, preservatives, isotonic agents, mucilages and the like.

The solid preparations for oral dosage can include capsules, tablets, pills, powders and granules. In preparing the solid preparations, generally, the compound of the present invention is mixed with at least one kind of an inert diluent such as sucrose, lactose or starch. In a usual preparation, the preparations can further include a supplementary material except the inert diluent, for example, a lubricant such as magnesium stealate or the like. Further, the capsules, tablets and pills can further include a buffer. The tablets and pills can further apply an enteric coat thereon.

The solution preparations for oral dosage can include inert diluents usually used by a person skilled in the art, for instance, pharmaceutical allowable emulsifiers including water, solutions, suspensions, syrups and elixirs. In addition to such inert diluents, the compositions can be blended with supplementary agents such as wetting agents, emulsifiers, suspensions, edulcorants, flavors and perfumes.

The preparations for per rectum dosage may preferably include excipients such as cocoa butter or suppository wax in addition to the compound of the present invention.

The dose of the compound represented by general formula (1) depends on the properties of the compound to be dosed, dosing route, the desired treating period and other factors, and is, in general, approximately 0.1 to 1000 mg/kg a day, and preferably approximately 1 to 100 mg/kg a day. If necessary, this dose for one day can be divided into 2-4 times.

EXAMPLE 1

Ethyl 3-(1,2,5-thiadiazol-3-yl-amino)-2-(2,6-dichloro-5-fuluoronicotinoyl)acrylate (Compound No.1)

A mixture of ethyl 2,6-dichloro-5-fluoronicotinoylacetate (5.4 g), triethyl orthoformate (4.8 ml) and acetic anhydride (5.5 ml) was stirred at 130° C. for 2 hours. After the solvent was removed in vacuo, a solution of 3-amino-1,2,5-thiadiazole hydrochloride (2.75 g) and triethylamine (2 g) in chloroform (20 ml) was added to the residue. The mixture was stirred at room temperature for 20 hours. The solvent was removed in vacuo. The residue was purified by chromatography on silicagel (chloroform as an eluent). The title compound No. 1 was obtained as a yellow oil ( 6.8 g).

$^1$H-NMR(CDCl$_3$) δ; 0.96 and 1.17(t,J=7 Hz,3H), 4.16(q,J=7 Hz,2H), 7.43 and 7.56(d,J=7 Hz,1H), 8.33 and 8.38(s,1H), 8.95 and 9.03(d,J=12.5 Hz,1H)

EXAMPLE 2

Ethyl 7-chloro-6-fluoro-1(1,2,5-thiadiazol-3-yl)-1,4-dihydro-4-oxo-1,8-naphthyridine-3-carboxylate (Compound No.2)

To a solution of compound No. 1 (6.8 g) in tetrahydrofuran (200 ml), 0.7 g of sodium hydride (60% in oil) was added with ice cooling. Then the solution was stirred for 1 hour at the same temperature. After addition of aqueous 5% citric acid solution (50 ml), tetrahydrofuran was removed in vacuo. The aqueous solution was extracted with chloroform (200 ml). The organic phase was washed with water, dried over $Na_2SO_4$ and evaporated under reduced pressure. To the residue was added diisopropylether and filtrated. The title compound No. 2 was obtained as a yellow solid (5.2 g).

Melting point: 175°–178° C. $^1$H-NMR(CDCl$_3$) δ; 1.43(t,J=7 Hz,3H), 4.43(q,J=7 Hz,2H), 8.54(d,J=6.9 Hz,1H), 9.26(s,1H), 9.27(s,1H)

EXAMPLE 3

7-Chloro-6-fluoro-1-(1,2,5-thiadiazol-3-yl)-1,4-dihydro-4-oxo-1,8-naphthyridine-3-carboxylic acid (Compound No.3)

Compound No.2 (5 g) was dissolved in acetic acid (50 ml) and 6N-HCl (20 ml). The solution was stirred at 100° C. for 0.5 hour. After cooling, the precipitate was filtrated and washed with water, ethanol and ether. The title compound No. 3 was obtained as pale yellow needles (4.5 g).

Melting point: 222°–223° C. $^1$H-NMR(DMSO-d$_6$) δ; 8.8(d,J=7.8 Hz,1H), 9.24(s,1H), 9.26(s,1H)

EXAMPLE 4

6-Fluoro-7-(pyrrolidin-1-yl)-1-(1,2,5-thiadiazole-3-yl)-1,4-dihydro-4-oxo-1,8-naphthyridine-3-carboxylic acid (Compound No.4)

A mixture of compound No.3 (80 mg), pyrrolidine (21 mg) and triethylamine (50 mg) in acetonitrile (5 ml) was stirred at 80° C. for 30 minutes. After cooling, the precipitate was filtrated and washed with ethanol and diisopropylether successively. The title compound No. 4 was obtained as a pale yellow solid (85 mg).

Melting point: 269°–273° C. $^1$H-NMR(CDCl$_3$) δ; 1.9–2.1(m,4H), 3.7(brs,4H), 8.0(d,J=12.8 Hz,1H), 9.12(s,1H), 9.18(s,1H)

EXAMPLE 5

Compounds Nos. 5–11 listed in Tables 1 and 2 were prepared in a similar manner to Example 4. The data are also shown in Tables 1–2.

TABLE 1

Compound:

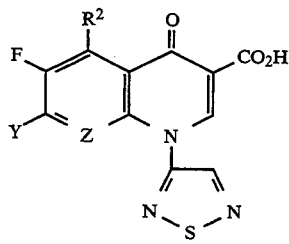

| Compound No. | R$^2$ | Group Y | Z | Property | Melting point (°C.) | $^1$H-NMR | Solvent |
|---|---|---|---|---|---|---|---|
| 5 | H | ⌬N— (tetrahydropyridine) | N | Pale yellow solid | 274 ∫ 276 | [CDCl$_3$+DMSO-d$_6$] δ; 4.25–4.45(m, 2H), 4.65–4.85(m, 2H), 5.95(s, 2H), 8.1(d, J=12.4Hz, 1H), 9.17(s, 1H), 9.18(s, 1H) | CH$_3$CN |
| 6 | H | O⌬N— (morpholine) | N | Colorless solid | 254 ∫ 257 | [CDCl$_3$+DMSO-d$_6$] δ; 3.65–3.85(m, 8H), 8.15(d, J=13.3Hz, 1H), 9.03(s, 1H), 9.11(s, 1H) | CH$_3$CN |
| 7 | H | S⌬N— (thiomorpholine) | N | Pale yellow solid | 244 ∫ 246 | [CDCl$_3$] δ; 2.65–2.8(m, 4H), 4.0–4.1(m, 4H), 8.15(d, J=13.3Hz, 1H), 9.0(s, 1H), 9.1(s, 1H) | CH$_3$CN |

TABLE 2

| Compound No. | R$^2$ | Group Y | Z | Property | Melting point (°C.) | $^1$H-NMR | Solvent |
|---|---|---|---|---|---|---|---|
| 8 | H | ⌬N—/N (pyrazole) | N | Red solid | 288 ∫ 292 | [DMSO-d$_6$] δ; 2.85–3.0(m, 2H), 3.8–3.9(m, 2H), 7.47(s, 1H), 8.19(d, J=12.4Hz, 1H), 9.06(s, 1H), 9.4(s, 1H) | CH$_3$CN |
| 9 | H | N⌬N— (imidazole) | N | Pale yellow solid | 233 ∫ 236 | [DMSO-d$_6$] δ; 7.22(s, 1H), 7.74(s, 1H), 8.39(s, 1H), 8.88(d, J=10.2Hz, 1H), 9.23(s, 1H), 9.4(s, 1H) | CH$_3$CN |

TABLE 2-continued

| Compound No. | R² | Group Y | Z | Property | Melting point (°C.) | ¹H-NMR | Solvent |
|---|---|---|---|---|---|---|---|
| 10 | H | S⌒N— (five-membered ring) | N | Colorless solid | 238.5 ∫ 239.5 | [DMSO-d₆] δ; 3.05-3.2(m, 2H), 3.92(brs, 2H), 4.73(s, 2H), 8.17(d, J=12.8Hz, 1H), 9.0(s, 1H), 9.35(s, 1H) | CH₃CN |
| 11 | H | HO-(S)-⌒N— (piperidine) | N | Pale ocher solid | 217 ∫ 219 | [DMSO-d₆] δ; 1.91(brs, 2H), 4.36(brs, 1H), 5.09(brs, 1H), 8.04(d, J=12.7Hz, 1H), 8.96(s, 1H), 9.33(s, 1H) | CH₃CN ET₃N |

EXAMPLE 6

6-Fluoro-7-(7-amino-5-azaspiro[2.4]heptan-5-yl)-1-(1,2,5-thiadiazol-3-yl)-1,4-dihydro-4-oxo-1,8-naphthyridine-3-carboxylic acid hydrochloride (Compound No.12)

A mixture of compound No.3 (114 mg), triethylamine (70 mg) and 7-t-buthoxycarbonylamino-5-azaspiro[2.4]heptane (90 mg) in acetonitrile (5 ml) was stirred at 80° C. for 10 minutes. After the solvent was removed in vacuo, the residue was extracted with chloroform (50 ml). The organic layer was washed with 5% aqueous citric acid solution and water successively, then dried. After the solvent was removed in vacuo, 4N-HCl/1,4-dioxane (5 ml) was added to the residue. The solution was stirred at room temperature for 1 hour. The precipitate was collected by filtration. The title compound No. 12 was obtained as a yellow solid (110 mg).

Melting point: 216°–221.5° C. ¹H-NMR(DMSO-d₆) δ; 0.7–1.0(m,3H), 1.0–1.2(m,1H), 3.8–4.4(m,3H), 8.16(d,J=12.2 Hz,1H), 8.35(brs,3H), 9.0(s,1H), 9.36(s,1H)

EXAMPLE 7

Compounds Nos. 13 and 14 listed in Table 3 were prepared in a similar manner to Example 6. The results are also shown in Table 3.

TABLE 3

Compound:

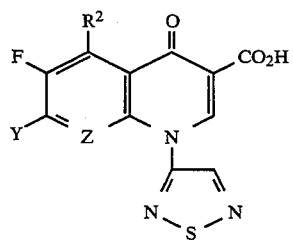

| Compound No. | R² | Group Y | Z | Property | Melting point (°C.) | ¹H-NMR | Solvent |
|---|---|---|---|---|---|---|---|
| 13 | H | H₂N-spiro[2.5] N— ·HCl isomer A | N | Yellow solid | 215 ∫ 220.5 | [DMSO-d₆] δ; 0.7–1.0(m, 3H), 1.0–1.2(m, 1H), 3.7–4.4(m, 3H), 8.16(d, J=12.4Hz, 1H), 8.25(brs, 3H), 9.0(s, 1H), 9.36(s, 1H) | CH₃CN ↓ 4N—HCl/ 1,4-dioxane |
| 14 | H | H₂N-spiro[2.5] N— ·HCl isomer B | N | Yellow solid | 217 ∫ 224 | [DMSO-d₆] δ; 0.7–1.0(m, 3H), 1.0–1.2(m, 1H), 3.7–4.3(m, 3H), 8.16(d, J=12.2Hz, 1H), 8.37(brs, 3H), 9.0(s, 1H), 9.36(s, 1H) | CH₃CN ↓ 4N—HCl/ 1,4-dioxane |

EXAMPLE 8

6-Fluoro-7-(2-aminoethylthio)-1-(1,2,5-thiadiazole-3-yl)-1,4-dihydro-4-oxo-1,8-naphthyridine-3-carboxylic acid hydrochloride (Compound No.15)

A mixture of compound No.3 (100 mg), triethylamine (60 mg) and 2-t-buthoxycarbonylaminoethanethiol (71 mg) in acetonitrile (5 ml) was stirred at room temperature for 30 minutes. The precipitate was collected by filtration and dissolved in acetic acid (1 ml) and 6N-HCl(1 ml). After stirring at 100° C. for 20 minutes, 5 ml of water was added to this solution. The precipitate was collected by filtration and washed with ethanol, chloroform and ether successively. The title compound No. 15 was obtained as a colorless solid (70 mg).

Melting point: Colored and decomposed at 269° C. or more ¹H-NMR(DMSO-d₆) δ; 2.84(brs,2H), 3.3(brs,2H), 8.14(brs,3H), 8.47(d,J=9.0 Hz,1H), 9.19(s,1H), 9.33(s,1H)

EXAMPLE 9

7-(3-Amino-1-cyclohexen-1-yl)-6-fluoro-1-(1,2,5-thiadiazol-3-yl)-1,4-dihydro-4-oxo-1,8-naphthyridine-3-carboxylicacid hydrochloride (Compound No.16)

EXAMPLE 10

Compound No.17 listed in Table 4 was synthesized in a similar manner to Example 9. The data are also shown in Table 4.

TABLE 4

Compound:

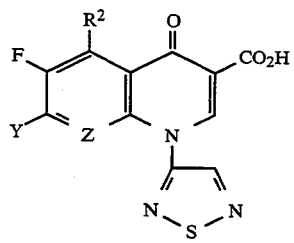

| Compound No. | Group R² | Y | Z | Property | Melting point (°C.) | ¹H-NMR | Soluent |
|---|---|---|---|---|---|---|---|
| 17 | H | O (cyclohexenone) | N | Yellow solid | 188 ∫ 195 | [CDCl₃] δ; 2.1–2.3(m, 2H), 2.5–2.65(m, 2H), 2.7–2.8(m, 2H), 6.84(s, 1H), 8.6(d, J=9.8Hz, 1H), 9.12(s, 1H), 9.46(s, 1H) | DMF |

The compound No.2 (200 mg) obtained in Example 2, bistriphenylphosphine-palladium(II)chloride (10 mg) and 2,6-di-t-butyl-4-methylphenol (2 pieces of crystal) were dissolved in N,N-dimethylformamide (2 ml). 300 mg of 3-t-buthoxycarbonylamino-1-tri-n-butylstannyl-1-cyclohexene were added thereto at 85° C. during 20 minutes. After stirring at 100° C. for 1.5 hours, the solvent was removed, the residue was added with hexane (10 ml) and filtrated. The collected solid matter was purified by chromatography on silicagel(chloroform-/ethylacetate 10:1). The pale yellow solid (100 mg) which was obtained was dissolved in a mixture of acetic acid (1 ml) and 6N-HCl (1 ml), then this solution was stirred at 100° C. for 30 minutes. After evaporation of the solvent, 5 ml of ethanol was added. The precipitate was collected by filtration and washed with diisopropylether. The title compound No. 16 was obtained as a yellow solid (30 mg).

Melting point: Colored and decomposed at 235° C. or more ¹H-NMR(DMSO-d₆) δ; 1.5–1.8(m,2H), 1.8–2.1(m,2H), 2.36(brs,2H), 4.04(brs,1H), 6.8(s,1H), 8.35(brs,3H), 8.63(d,J=10.7 Hz,1H), 9.25(brs,2H)

EXAMPLE 11

7-(3-(S)-Aminopyrrolidin-1-yl)-6-fluoro-1-(1,2,5-thiadiazol-3-yl)-1,4-dihydro-4-oxo-1,8-naphthyridine-3-carboxylic acid hydrochloride (Compound No.18)

A mixture of compound No.3 (1.5 g), triethylamine (1.06 g) and 3-(S)-aminopyrrolidine (0.46 g) in acetonitrile (150 ml) was stirred at 80° C. for 60 minutes. After cooling, the precipitate was filtrated and washed with ethanol (5 ml), then dissolved in 10 ml of c-HCl and stirred for 10 minutes. After the solvent was evaporated, ethanol (10 ml) was added for filtration. A yellow solid of the title compound was obtained (1.6 g). Crystallization from ethanol-water yielded the title compound No. 18 in pale yellow needles (1.5 g).

Melting point: Colored from 235° C., and melted at 257°–260° C. ¹H-NMR(DMSO-d₆) δ; 2.5(brs,1H), 2.51(brs,1H), 8.13(d,J=12.7 Hz,1H), 8.0–8.8(br,3H), 9.00(s,1H), 9.33(s,1H)

EXAMPLE 12

Compounds Nos. 19–31 listed in Tables 5–8 were synthesized in a similar manner to Example 11. The data are also shown in Tables 5–8.

TABLE 5

Compound:

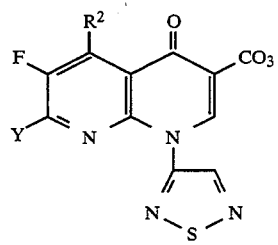

| Compound No. | R² | Group Y | Z | Property | Melting point (°C.) | ¹H-NMR | Solvent |
|---|---|---|---|---|---|---|---|
| 19 | H | H₂N, Me, Cis-(−) .HCl | N | Pale yellow needles | 241 ∫ 243 | [DMSO-d₆] δ; 1.10(d, J=6.8Hz, 3H), 2.5–2.7(m, 1H), 8.13(d, J=12.7Hz, 1H), 8.4(brs, 3H), 8.99(s, 1H), 9.35(s, 1H) | MeCN Et₃N |
| 20 | H | NH₂, (3R, 1S) .HCl | N | Pale ocher solid | 255 ∫ 260 | [DMSO-d₆] δ; 1.26(d, J=6.4Hz, 3H), 1.70(brs, 1H), 2.04(brs, 1H), 2.45(brs, 1H), 8.07(d, J=12.7Hz, 1H), 8.23(brs, 3H), 8.97(s, 1H), 9.36(s, 1H) | MeCN Et₃N |

TABLE 6

| Compound No. | R² | Group Y | Z | Property | Melting point (°C.) | ¹H-NMR | Solvent |
|---|---|---|---|---|---|---|---|
| 21 | H | Me, H₂N .HCl | N | Pale yellow solid | 257 ∫ 259 | [DMSO-d₆] δ; 1.46(s, 3H), 2.09(brs, 1H), 2.25(brs, 1H), 8.14(d, J=12.2Hz, 1H), 9.00(s, 1H), 9.36(s, 1H) | MeCN Et₃N |
| 22 | H | H₂N, Me .HCl Cis form | N | Pale orange solid | 207 ∫ 213 | [DMSO-d₆] δ; 0.93(d, J=6.35Hz, 3H), 2.91(brs, 2H), 8.10(brs, 1H), 8.0–8.9(br, 3H), 8.98(s, 1H), 9.42(s, 1H) | MeCN Et₃N |
| 23 | H | H₂N .HCl | N | Pale yellow solid | 250 ∫ 260 Decomposed | [DMSO-d₆] δ; 3.8–4.0(m, 2H), 8.16(d, J=11.2Hz, 1H), 8.62(brs, 3H), 9.03(s, 1H), 9.30(s, 1H) | MeCN Et₃N |
| 24 | H | HN .HCl | N | Pale yellow solid | 268 ∫ 275 Decomposed | [DMSO-d₆] δ; 3.48(s, 4H), 3.86(s, 4H), 8.27(d, J=13.2Hz, 1H), 9.04(s, 1H), 9.32(s, 1H), 9.1–9.8(br, 2H) | MeCN Et₃N |

TABLE 7

| Compound No. | R² | Group Y | Z | Property | Melting point (°C.) | ¹H-NMR | Solvent |
|---|---|---|---|---|---|---|---|
| 25 | H | MeN⟨ ⟩N— .HCl | N | Pale yellow solid | Colored from 240° C., decomposed | [DMSO-d₆+D₂O] δ; 2.82(s, 3H), 8.24(d, J=13.2Hz, 1H), 9.01(s, 1H), 9.27(s, 1H) | CH₃CN Et₃N |
| 26 | H | HN⟨ ⟩N— Me (S) .HCl | N | Colorless solid | Colored from 268° C., decomposed | [DMSO-d₆] δ; 1.2(d, J=6.4Hz, 3H), 3.0–3.15(m, 1H), 3.45–3.6(m, 1H), 4.1–4.3(m, 2H), 8.27(d, J=13.2Hz, 1H), 9.04(s, 1H), 9.31(s, 1H), 9.4–9.7(br, 2H) | CH₃CN Et₃N |
| 27 | H | HN⟨ ⟩N— FCH₂ (R) .HCl | N | Colorless solid | 251 ∫ 253 | [DMSO-d₆] δ; 3.1–3.3(m, 2H), 3.5–3.8(m, 2H), 4.15–4.32(m, 2H), 4.6(brs, 1H), 4.8(brs, 1H), 8.3(d, J=13.2Hz, 1H), 9.05(s, 1H), 9.32(s, 1H), 9.9(brs, 1H) | CH₃CN Et₃N |
| 28 | H | Me, HN⟨ ⟩N— Me Cis.HCl | N | Colorless solid | Colored from 292° C., decomposed | [DMSO-d₆] δ; 1.22(d, J=7.3Hz, 6H), 3.15–3.5(m, 4H), 4.22(d, J=12.7Hz, 2H), 8.27(d, J=12.7Hz, 1H), 9.05(s, 1H), 9.32(s, 1H), 9.7(brs, 1H) | CH₃CN Et₃N |

TABLE 8

| Compound No. | R² | Group Y | Z | Property | Melting point (°C.) | ¹H-NMR | Solvent |
|---|---|---|---|---|---|---|---|
| 29 | H | HN⟨ ⟩N— .HCl (1R, 4R) | N | Pale yellow solid | Colored from 259° C., decomposed | [DMSO-d₆] δ; 1.9–2.2(m, 2H), 4.48(s, 1H) 8.2(d, J=12.2Hz, 1H), 9.01(s, 1H), 9.26(brs, 1H), 9.31(s, 1H), 9.71(brs, 1H) | CH₃CN Et₃N |
| 30 | H | MeN⟨ ⟩N— .HCl (1R, 4R) | N | Colorless solid | Colored from 277° C., decomposed | [DMSO-d₆] δ; 2.0–2.2(brs, 1H), 2.3–2.5(brs, 1H), 2.83(s, 3H), 3.05–3.2(m, 1H), 3.6–3.9(br, 1H), 4.44(s, 1H), 8.20(d, J=12.2Hz, 1H), 9.0(s, 1H), 9.33(s, 1H), 11.1(brs, 1H) | CH₃CN Et₃N |
| 31 | H | HN⟨ ⟩N— .HCl | N | Colorless solid | Colored from 278° C., decomposed | [DMSO-d₆] δ; 1.8–2.9(m, 4H), 3.5–3.6(m, 2H), 4.0–4.15(m, 4H), 8.26(d, J=13.2Hz, 1H), 9.03(s, 1H), 9.30(s, 1H), 9.4–9.9(br, 1H) | CH₃CN Et₃N |

EXAMPLE 13

Ethyl 3-(1,2,5-thiadiazol-3-yl-amino)-2-(2,3,4,5-tetra-fluorobenzoyl)acrylate (Compound No.32)

A mixture of ethyl 2,3,4,5-tetrafluorobenzoylacetate(2.64 g), ethyl orthoformate(2.5 ml) and acetic anhydride(2.8 ml) was stirred at 130° C. for 6 hours. After the solvent was removed in vacuo, a solution of 3-amino-1,2,5-thiadiazole hydrochloride (1.38 g) and triethylamine(1 g) in benzene(20 ml) was added to the residue. The mixture was stirred at room temperature for 2 hours. The solvent was removed in vacuo. The residue was purified by chromatography on silicagel(chloroform/ethyl acetate 50:1 as an eluent). The title compound NO. 32 was obtained as a yellow solid (3.7 g).

Melting point: 81°-83° C. ¹H-NMR(CDCl₃) δ;1.06 and 1.22 (t,J=7 Hz,3H) 4.15 and 4.18 (q,J=7 Hz,2H) 7.05-7.2 and 7.25-7.4 (m,1H) 8.31 and 8.36 (s,1H) 8.74 and 8.95 (d,J=12.2 Hz,1H)

EXAMPLE 14

Ethyl 1-(1,2,5-thiadiazol-3-yl)-6,7,8-trifluoro-1,4-dihydro-4-oxoquinoline-3-carboxylate (Compound No.33)

To a solution of compound No.32 (3.7 g) in tetrahydrofuran (100 ml), 0.4 g of sodium hydride (60% in oil) was added with ice cooling over 20 minutes. Then the solution was stirred for 20 minutes at room temperature. After addition of 5% aqueous citric acid solution (10 ml), tetrahydrofuran was removed in vacuo. The aqueous solution was extracted with chloroform (100 ml). The organic phase was washed with water, dried (MgSO₄) and evaporated. The residue was added with diisopropylether and the solid matter was collected by filtration. The title compound No. was obtained as a colorless solid (2.7 g).

Melting point: 167°-169° C. ¹H-NMR(CDCl₃) δ; 1.39(t,J=7 Hz, 3H), 4.39(q,J=7 Hz, 2H), 8.1-8.25(m,1H), 8.48(s,1H), 8.72(s,1H)

EXAMPLE 15

1-(1,2,5-Thiadiazol-3-yl)-6,7,8-trifluoro-1,4-dihydro-4-oxoquinoline-3-carboxylic acid (Compound No.34)

Compound No.33 (2.7 g) was dissolved in acetic acid (25 ml) and 6N-HCl (10 ml). The solution was stirred at 100° C. for 0.5 hour. After cooling, the precipitate was filtrated and washed with water, ethanol and ether successively. The title compound No. 34 was obtained as a colorless solid (2.3 g).

Melting point: 205°-207° C. ¹H-NMR(DMSO-d₆) δ; 8.15-8.3(m,1H), 9.07(s,1H), 9.23(s,1H)

EXAMPLE 16

Compounds Nos. 35-39 listed in Tables 9 and 10 were prepared in a similar manner to Example 11, starting from compound No.34 and indicated amines. The results are shown in Tables 9 and 10.

TABLE 9

Compound:

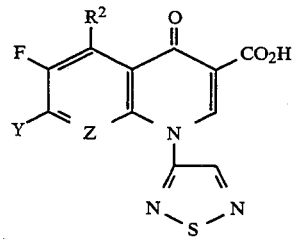

| Compound No. | R² | Group Y | Z | Property | Melting point (°C.) | ¹H-NMR | Solvent |
|---|---|---|---|---|---|---|---|
| 35 | H | H₂N(S)—(pyrrolidinyl)—N— .HCl | C\|F | Ocher solid | 206 ∫ 212 | [DMSO-d₆] δ; 1.92-2.09(m, 1H), 2.09-2.27(m, 1H), 3.6-4.0(m, 4H), 7.85(d, J=13.7Hz, 1H). 8.42(brs, 3H), 8.90(s, 1H), 9.22(s, 1H) | MeCN Et₃N |
| 36 | H | H₂N—(3-Me-pyrrolidinyl)—N— Me .HCl Cis (−) | C\|F | Pale yellow solid | 231 ∫ 234 | DMSO-d₆] δ; 1.04(d, J=6.8Hz, 3H), 2.4-2.6(m, 1H), 3.5-4.1(m, 4H), 7.85(d, J=13.7Hz, 1H), 8.0-8.75(br, 3H), 8.90(s, 1H), 9.22(s, 1H) | MeCN Et₃N |

TABLE 10

| Compound No. | R² | Y | Z | Property | Melting point (°C.) | ¹H-NMR | Solvent |
|---|---|---|---|---|---|---|---|
| 37 | H | HN⟨piperazinyl⟩N— .HCl | C\|F | Pale yellow solid | 268 ∫ 275 decomposed | [DMSO-d₆] δ; 3.15(brs, 4H), 3.46(brs, 4H), 8.00(d, J=11.7Hz, 1H), 8.98(s, 1H), 9.23(s, 1H), 9.43(brs, 1H), 9.73(brs, 1H) | MeCN Et₃N |
| 38 | H | MeN⟨piperazinyl⟩N— .HCl | C\|F | Pale yellow solid | 244 ∫ 250 decomposed | [DMSO-d₆] δ; 2.77(s, 3H), 3.53(s, 4H), 7.98(d, J=11.7Hz, 1H), 8.98(s, 1H), 9.23(s, 1H), 11.0-11.3(br, 1H) | MeCN Et₃N |

TABLE 10-continued

| Compound No. | R² | Y | Z | Property | Melting point (°C.) | ¹H-NMR | Solvent |
|---|---|---|---|---|---|---|---|
| 39 | H | H₂N—◇—N— .HCl | C\|F | Pale yellow solid | Colored from 200° C., decomposed | [DMSO-d₆] δ; 3.8–4.0(m, 2H), 7.90(d, J=12.7Hz, 1H), 8.38(brs, 3H), 8.92(s, 1H), 9.22(s, 1H), | MeCN Et₃N |

EXAMPLE 17

Ethyl 2-(2,4,5-trifluorobenzoyl)-3-(1,2,5-thiadiazol-3-ylamino)acrylate (Compound No.40)

A mixture of ethyl 2,4,5-trifluorobenzoylacetate(8.94 g), ethyl orthoformate(8.09 g) and acetic anhydride(16.7 g) was stirred at 130° C. for 3 hours. After the solvent was removed in vacuo, a solution of 3-amino-1,2,5-thiadiazole hydrochloride (5.0 g) and triethylamine (3.68 g) in benzene(50 ml) was added to the residue. The mixture was stirred at room temperature for 1 night. The solvent was evaporated and the residue was purified by chromatography on silicagel(-chloroform as an eluent). The title compound No. 40 was obtained as a colorless solid (10.4 g).

Melting point: 117°–118° C. ¹H-NMR(CDCl₃) δ; 1.04 and 1.19 (t,J=7 Hz,3H), 4.09–4.26(m,2H), 6.88–7.01(m,1H), 7.31–7.42 and 7.47–7.61(m,1H), 8.28 and 8.33(s,1H) 8.68 and 8.91(d,J=12.5 Hz,1H)

EXAMPLE 18

Ethyl 6,7-difluoro-1-(1,2,5-thiadiazol-3-yl)-1,4-dihydro-4-oxoquinoline-3-carboxylate (Compound No.41)

To a solution of compound No.40 (1.6 g) in tetrahydrofuran (50 ml), 0.22 g of sodium hydride (60% in oil) was added at room temperature for 1 hour. After addition of 5% aqueous citric acid solution, tetrahydrofuran was removed in vacuo. The aqueous solution was extracted with chloroform (50 ml). Evaporation was carried out after drying over Na₂SO₄). The residue was purified by chromatography on silicagel (chloroform as an eluent). The title compound No. 41 was obtained as a colorless solid (1.13 g).

Melting point: 189°–192° C. ¹H-NMR(DMSO-d₆) δ; 1.28(t,J=7 HZ,3H), 4.25(q,J=7 HZ,2H), 7.69(dd,J=6.5 HZ,J=12 Hz,1H), 8.14(dd,J=10.3 Hz,J=8.8 Hz,1H), 8.81(s,1H),9.25(s,1H)

EXAMPLE 19

6,7-Difluoro-1-(1,2,5-thiadiazol-3-yl)-1,4-dihydro-4-oxoquinoline-3-carboxylic acid (Compound No.42)

Compound No.41 (6.9 g) was dissolved in acetic acid (100 ml) and c-HCl (25 ml). The solution was stirred at 100° C. for 1 hour. After evaporation of the solvent, 50 ml of chloroform was added. The precipitate was filtrated and washed with diethylether (30 ml). The title compound No. 42 was obtained as a colorless solid (6.0 g).

Melting point: 255–256.5° C. ¹H-NMR(DMSO-d₆) δ; 7.86(dd,J=11.7 Hz,J=6.8 Hz,1H), 8.36(dd,J=10.2 Hz,J=8.8 Hz,1H), 9.15(s,1H), 9.26(s,1H)

EXAMPLE 20

Compound No.43 listed in Table 11 was synthesized in a similar manner to Example 4, proceeding from the corresponding compound No. 42 obtained in Example 19. The data are also shown in Table 11.

TABLE 11

Compound:

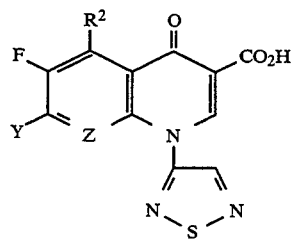

| Compound No. | R² | Group Y | Z | Property | Melting point (°C.) | ¹H-NMR | Solvent |
|---|---|---|---|---|---|---|---|
| 43 | H | HO(S)—◯—N— | C\|H | Yellow solid | 276 ∫ 280 | [DMSO-d₆] δ; 1.8–2.05(m, 2H), 3.4–3.7(m, 3H), 4.35(s, 1H), 5.05(s, 1H), 6.30(d, J=7.8Hz, 1H), 7.86(d, J=14.2Hz, 1H), 8.90(s, 1H), 9.33(s, 1H) | MeCN Et₃N |

EXAMPLE 21

Compounds Nos. 44–53 listed in Tables 12–14 were synthesized in a similar manner to Example 11, proceeding from the corresponding compound No.42 obtained in Example 19. The data are also shown in Tables 12–14.

TABLE 12

Compound:

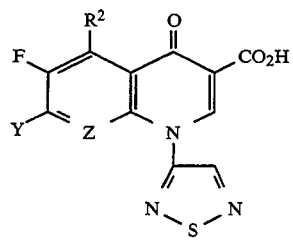

| Compound No. | Group R² | Y | Z | Property | Melting point (°C.) | ¹H-NMR | Solvent |
|---|---|---|---|---|---|---|---|
| 44 | H | H₂N-(S)-pyrrolidinyl .HCl | C—H | Yellow needles | Colored from 235, 258.5–260 | [DMSO-d₆] δ; 2.13(brs, 1H), 2.20–2.41(m, 1H), 6.34(d, J=7.3Hz, 1H), 7.91(d, J=14.2Hz, 1H), 8.48(brs, 3H), 8.94(s, 1H), 9.34(s, 1H) | MeCN Et₃N |
| 45 | H | H₂N-Me-pyrrolidinyl Cis(−).HCl | C—H | Yellow needles | Colored from 210, 256–260 | [DMSO-d₆] δ; 1.08(d, J=6.8Hz, 3H), 2.60(brs, 1H), 6.30(d, J=7.3Hz, 1H), 7.92(d, J=14.2Hz, 1H), 8.36(brs, 3H), 8.94(s, 1H), 9.34(s, 1H) | MeCN Et₃N |

TABLE 13

| Compound No. | Group R² | Y | Z | Property | Melting point (°C.) | ¹H-NMR | Solvent |
|---|---|---|---|---|---|---|---|
| 46 | H | H₂N-CH₂-Me-pyrrolidinyl .HCl Cis form | C—H | Orange solid | 190 ∫ 197 | [DMSO-d₆] δ; 0.95(brs, 3H), 2.91(brs, 2H), 6.32(brs, 1H), 7.88(d, J=13.2Hz, 1H), 7.80~8.75(br, 3H), 8.91(s, 1H), 9.36(s, 1H) | MeCN Et₃N |
| 47 | H | H₂N-CH(Me)-pyrrolidinyl (3R, 1'S).HCl | C—H | Pale red solid | 280 ∫ 285 Colored | [DMSO-d₆] δ; 1.24(brs, 3H), 1.71(brs, 1H), 2.08(brs, 1H), 2.40(brs, 1H), 6.32(brs, 1H), 7.88(d, J=14.2Hz, 1H), 8.90(s, 1H), 9.32(s, 1H) | MeCN Et₃N |
| 48 | H | Me-H₂N-pyrrolidinyl .HCl | C—H | Pale yellow solid | 273 ∫ 280 | [DMSO-d₆] δ; 1.45(s, 3H), 2.08(brs, 1H), 2.22(brs, 1H), 6.36(brs, 1H), 7.93(d, J=14.2Hz, 1H), 8.55(brs, 3H), 8.94(s, 1H), 9.35(s, 1H) | MeCN Et₃N |
| 49 | H | HN-piperazinyl .HCl | C—H | Pale yellow solid | Colored from 250, decomposed in 264–266 | [DMSO-d₆] δ; 3.34(s, 4H), 6.98(d, J=6.8Hz, 1H), 8.03(d, J=13.2Hz, 1H), 9.02(s, 1H), 9.35(s, 1H), 9.30~9.82(br, 2H) | MeCN Et₃N |

TABLE 14

| Compound No. | Group R² | Y | Z | Property | Melting point (°C.) | ¹H-NMR | Solvent |
|---|---|---|---|---|---|---|---|
| 50 | H | MeN⟨ ⟩N— ·HCl | C\|H | Pale yellow solid | Colored from 250, decomposed in 264–268 | [DMSO-d₆] δ; 2.80(s, 3H), 3.7(brs, 2H), 7.01(d, J=6.8Hz, 1H), 8.05(d, J=13.2Hz, 1H), 9.02(s, 1H), 9.35(s, 1H), 11.0~11.4(br, 1H) | MeCN Et₃N |
| 51 | H | H₂N—⟨ ⟩N— ·HCl | C\|H | Pale orange solid | 230 ∫ 245 decomposed | [DMSO-d₆] δ; 3.85(brs, 2H), 4.1~4.5(m, 2H), 6.52(d, J=6.8Hz, 1H), 7.94(d, J=11.7Hz, 1H), 8.48(brs, 3H), 8.39(s, 1H), 9.33(s, 1H) | MeCN Et₃N |
| 52 | H | Me H₂N—⟨ ⟩N— ·HCl | C\|H | Pale orange solid | Colored from 210, 220–228 | [DMSO-d₆] δ; 1.24(d, J=6.4Hz) 1.39(d, J=5.8Hz) 3H), 3.5–4.1(m, 2H), 4.44(brs, 1H), 6.36(d, J=7.3Hz, 1H), 7.96(d, J=12.7HZ), 8.59(brs, 3H), 8.98(s, 1H), 9.32(s, 1H) | MeCN Et₃N |
| 53 | H | ·HCl HN—⟨ ⟩N— (1R, 4R) | C\|H | Yellow solid | Colored from 280, decomposed | [DMSO-d₆] δ; 1.9–2.15(m, 2H), 3.6–3.8(m, 3H), 4.44(s, 1H), 4.80(s, 1H), 6.54(d, J=7.3Hz, 1H), 7.97(d, J=13.7Hz, 1H), 8.95(s, 1H), 9.15(brs, 1H), 9.32(s, 1H), 9.6(brs, 1H) | MeCN Et₃N |

EXAMPLE 22

Ethyl 3-(1,2,3-thiadiazol-4-yl-amino)-2-(2,6-dichloro-5-fluoronicotinoyl)acrylate (Compound No.54)

A mixture of ethyl 2,6-dichloro-5-fluoronicotinoylacetate (5.6 g), ethyl orthoformate (5.2 ml) and acetic anhydride (5.6 ml) was stirred at 130° C. for 3 hours. After the solvent was removed in vacuo, a solution of 4-amino-1,2,3-thiadiazole hydrochloride (2.75 g) and triethylamine (2 g) in chloroform (20 ml) was added to the residue. The mixture was stirred at room temperature for 3 hours. The solvent was removed in vacuo. The residue was purified by chromatography on silicagel (chloroform/ethyl acetate 20:1 as an eluent). The title compound No. 54 was obtained as a pale yellow solid (7.8 g).

Melting point: 110.5°–113.5° C. ¹H-NMR(CDCl₃) δ; 0.97 and 1.17 (t,J=7 Hz,3H), 4.0–4.25 (m,2H), 7.44 and 7.54 (d,J=7 Hz, 1H), 8.14 and 8.19 (s,1H), 9.0 and 9.22 (d,J=13 Hz,1H)

EXAMPLE 23

Ethyl 7-chloro-6-fluoro-1-(1,2,3-thiadiazol-4-yl)-1,4-dihydro-4-oxo-1,8-naphthyridine-3-carboxylate (Compound No.55)

To a solution of compound No.54 (7.8 g) obtained in Example 22 in tetrahydrofuran (200 ml), 0.8 g of sodium hydride (60% in oil) was added at room temperature. The solution was stirred for 0.5 hour at the same temperature. After addition of aqueous 5% citric acid solution (40 ml), tetrahydrofuran was removed in vacuo. The precipitate was filtrated and washed with water, ethanol and isopropyl ether. The title compound No. 55 was obtained as a pale yellow solid (6.1 g).

Melting point: 188°–192° C. ¹H-NMR(CDCl₃) δ; 1.42(t,J=7 Hz,3H), 4.42(q,J=7 Hz,2H), 8.55(d,J=11.8 Hz,1H), 9.26(s,1H), 9.43(s,1H)

EXAMPLE 24

7-Chloro-6-fluoro-1-(1,2,3-thiadiazol-4-yl)-1,4-dihydro-4-oxo-1,8-naphthyridine-3-carboxylic acid (Compound No.56)

Compound No.55 (1 g) obtained in Example 23 was dissolved in a mixture of acetic acid (10 ml) and 6N-HCl (4 ml). The solution was stirred at 100° C. for 0.5 hour. After cooling, the precipitate was filtrated and washed with water, ethanol and ether. The title compound No. 56 was obtained as a pale yellow solid (0.9 g).

Melting point: 219–223° C. ¹H-NMR(DMSO-d₆) δ; 8.79(d,J=7.3 Hz,1H), 9.30(s,1H), 9.63(s,1H)

EXAMPLE 25

6-Fluoro-7-(pyrrolidin-1-yl)-1-(1,2,3-thiadiazole-4-yl)-1,4-dihydro-4-oxo-1,8-naphthyridine-3-carboxylic acid (Compound No.57)

A mixture of compound No.55 (216 mg) obtained in Example 23 and pyrrolidine (100 mg) in chloroform (5 ml) was stirred at room temperature for 1 hour. After evaporation of the solvent, acetic acid (1 ml) and 6N-HCl(1 ml) were added to the residue, then stirred at 100° C. for 12 hours. After evaporation in vacuo, ethanol (5 ml) was added for filtration, followed by washing with ethanol, chloroform and ether, successively. The title compound No. 57 was obtained as a colorless solid (140 mg).

Melting point: Colored and decomposed at 273° C. or more.   ¹H-NMR(DMSO-d₆)   δ;   1.87(brs,4H), 3.2-3.9(br,4H), 8.04(d,J=12.7 Hz,1H), 9.09(s,1H), 9.65(s,1H)

EXAMPLE 26

Compounds Nos. 58-62 listed in Tables 15 and 16 were synthesized in a similar manner to Example 25. The data are also shown in Tables 15-16.

(5.6 ml) was stirred at 130° C. for 8 hours. After the solvent was removed in vacuo, a solution of 4-amino-1, 2,3-thiadiazole hydrochloride (2.75 g) and triethylamine(2 g) in chloroform(20 ml) was added to the residue. The mixture was stirred at room temperature for 1 day. The solvent was removed in vacuo. The residue was purified by chromatography on silicagel

TABLE 15

Compound:

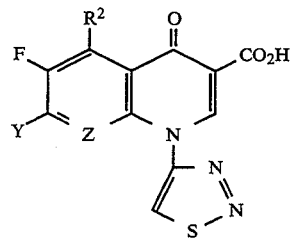

| Compound No. | Group R² | Y | Z | Property | Melting point (°C.) | ¹H-NMR | Solvent |
|---|---|---|---|---|---|---|---|
| 58 | H | H₂N-[pyrrolidine]-N— (S) .HCl | N | Yellow solid | Colored from 212, decomposed | [DMSO-d₆] δ; 1.95~2.3(m, 2H), 3.85(brs, 2H), 8.15(d, J=12.2Hz, 1H), 8.36(brs, 3H), 9.11(s, 1H), 9.70(s, 1H) | Et₃N/CHCl₃ ↓ AcOH, 6N—HCl |
| 59 | H | H₂N-[piperidine with Me]-N— Cis(−).HCl | N | Pale yellow solid | Colored from 246, 300 or more | [DMSO-d₆] δ; 1.06(d, J=6.4Hz, 3H), 2.4–2.7(br, 1H), 3.1–4.2(m, 5H), 8.14(d, J=12.2Hz, 1H), 8.35(brs, 3H), 9.11(s, 1H), 9.72(s, 1H), | " |

TABLE 16

| Compound No. | Group R² | Y | Z | Property | Melting point (°C.) | ¹H-NMR | Solvent |
|---|---|---|---|---|---|---|---|
| 60 | H | MeN-[piperazine]-N— .HCl | N | Pale yellow solid | Colored from 288, decomposed | [DMSO-d₆] δ; 2.74(s, 3H), 2.9–3.2(m, 2H), 4.1–4.3(m, 2H), 8.32(d, J=13.2Hz, 1H), 9.17(s, 1H), 9.67(s, 1H), 10.4–10.6(br, 1H) | Et₃N/CHCl₃ ↓ ACOH, 6N—HCl |
| 61 | H | HN-[piperazine]-N— .HCl | N | Pale yellow solid | Colored from 239, decomposed | [DMSO-d₆] δ; 3.13(s, 4H), 3.80(s, 4H), 8.26(d, J=12.7Hz, 1H), 9.14(s, 1H), 9.50(brs, 2H), 9.67(s, 1H) | " |
| 62 | H | H₂N-[azetidine ring]-N— .HCl | N | Colorless solid | Colored from 240, decomposed | [DMSO-d₆] δ; 3.51(brs, 3H), 3.73(brs, 2H), 8.15(d, J=10.2Hz, 1H), 8.42(brs, 2H), 8.56(brs, 1H), 9.1(s, 1H), 9.75(s, 1H) | " |

EXAMPLE 27

Ethyl 2-(2,4,5-trifluorobenzoyl)-3-(1,2,3-thiadiazol-4-ylamino)acrylate (Compound No.63)

A mixture of ethyl 2,4,5-trifluorobenzoylacetate (4.92 g), ethyl orthoformate (5.2 ml) and acetic anhydride (chloroform/ethyl acetate 30:1 as an eluent). The title compound No. 63 was obtained as a pale yellow solid (7.1 g).

Melting point: 104°–106° C. ¹H-NMR(CDCl₃) δ; 1.04 and 1.18(t,J=7 Hz,3H), 4.05–4.2(m,2H), 6.85-7.0(m,1H), 7.2-7.6(m,1H), 8.02 and 8.09(s,1H) 8.73 and 9.06(d,J=13 Hz,1H),

EXAMPLE 28

Ethyl 6,7-difluoro-1-(1,2,3-thiadiazol-4-yl)1,4-dihydro-4-oxoquinoline-3-carboxylate (Compound No.64)

To a solution of compound No.63 (7.1 g) obtained in Example 27 in tetrahydrofuran (200 ml), 0.8 g of sodium hydride (60% in oil) was added. Then the solution was stirred for 1 hour at room temperature. After addition of 5% aqueous citric acid solution (30 ml), tetrahydrofuran was removed in vacuo. The aqueous solution was extracted with chloroform (300 ml). The organic phase was dried ($Na_2SO_4$) and evaporated. The residue was purified by chromatography on silicagel (chloroform/ethyl acetate 5:1 as an eluent). The title compound No. 64 was obtained as a yellow solid (3.3 g).

Melting point: 198°-203° C. $^1$H-NMR(CDCl$_3$) δ; 1.34(t,J=7 Hz,3H), 4.29(q,J=7 Hz,2H), 6.81(dd,J=5.9 Hz,J=10.7 Hz,1H), 8.08(dd,J=8.3 Hz,J=10.2 Hz,1H), 8.46(s,1H), 9.43(s,1H)

EXAMPLE 29

6,7-Difluoro-1-(1,2,3-thiadiazol-4-yl)-1,4-dihydro-4-oxoquinoline-3-carboxylic acid (Compound No.65)

Compound No.64 (0.18 g) obtained in Example 28 was dissolved in acetic acid (1 ml) and 6N-HCl (1 ml). The solution was stirred at 100° C. for 1 hour. Water (30 ml) was added thereto, and the solid matter was collected by filtration, followed by washing with water, ethanol and ether successively. The title compound No. 65 was obtained as a yellow solid (115 mg).

Melting point: 239°-244° C. $^1$H-NMR(DMSO-d$_6$) δ;7.54(dd,J=11.7 Hz,J=6.8 Hz,1H), 8.36(dd,J=9.8 Hz,J=8.8 Hz,1H), 9.10(s,1H), 9.77(s,1H)

EXAMPLE 30

Ethyl 7-chloro-6-fluoro-1-(3-methyl-1,2,4-thiadiazol-5-yl)-1,4-dihydro-4-oxo-1,8-naphthyridine-3-carboxylate (Compound No.66)

A mixture of ethyl 2,6-dichloro-5-fluoronicotinoylacetate (4.2 g), ethyl orthoformate (3.9 ml) and acetic anhydride (4.3 ml) was stirred at 135° C. for 2 hours. After the solvent was removed in vacuo, the residue was added with chloroform (20 ml) and ethanol (10 ml). 3-Methyl-5-amino-1,2,4-thiadiazole (1.73 g) was added thereto at room temperature and allowed to react at the same temperature for 1 hour. The solvent was removed. The residue was purified by chromatography on silica-gel (chloroform/methanol 40:1 as an eluent). An yellow oil (5.8 g) was obtained. To a solution of this oily compound (400 g) in N,N-dimethylformamide (5 ml), 40 mg of sodium hydride (60% in oil) was added. Then the solution was stirred for 0.5 hour at 100° C. The solvent was removed. The residue was added with chloroform and water for separating an organic phase. The organic phase was washed dried ($Na_2SO_4$) and evaporated for collecting the precipitated solid. The title compound No.66 was obtained as a colorless solid (0.18 g).

Melting point: 235°-237° C. $^1$H-NMR(CDCl$_3$) δ; 1.46(t,J=7 Hz,3H), 2.69(s,3H), 4.47(q,J=7 Hz,2H), 8.54(d,J=7 Hz,1H), 9.96(s,1H)

EXAMPLE 31

7-Chloro-6-fluoro-1-(3-methyl-1,2,4-thiadiazol-5-yl)-1,4-dihydro-4-oxo-1,8-naphthyridine-3-carboxylic acid (Compound No.67)

Compound No.66 (1g) obtained in Example 30 was dissolved in acetic acid (40 ml) and c-HCl (10 ml). The solution was stirred at 100° C. for 0.5 hour. After evaporating the solvent, the residue was added with water followed by filtration, washing with water, ethanol, ether and n-hexane successively. The title compound No. 67 was obtained as a colorless solid (0.84 g).

Melting point: 260°-262° C. $^1$H-NMR(DMSO-d$_6$) δ; 2.63(s,3H), 8.78(d,J=8 Hz,1H), 9.75(s,1H)

EXAMPLE 32

6-Fluoro-7-(pyrrolidin-1-yl)-1-(3-methyl-1,2,4-thiadiazol-5-yl)-1,4-dihydro-4-oxo-1,8-naphthyridine-3-carboxylic acid (Compound No.68)

Compound No.66 (100 mg) obtained in Example 30 was dissolved in chloroform (4 ml), to which pyrrolidine (44 mg) and triethylamine (30 mg) were added for allowing to react at room temperature for 10 minutes. After evaporation of the solvent, acetic acid (2 ml) and c-HCl (1 ml) were added, then stirred at 100° C. for 1.5 hours. The precipitated solid was collected by filtration and washed with ethanol, ether and n-hexane, successively. The title compound No. 68 was obtained as a pale yellow solid (40 mg).

Melting point: 300° C. or more $^1$H-NMR(CDCl-$_{13}$) δ; 2.15(brs,4H), 2.66(s,3H), 3.98(s,4H), 8.01(d,J=13 Hz,1H), 10.02(s,1H)

EXAMPLE 33

Compounds Nos. 69-72 listed in Tables 17-18 were synthesized in a similar manner to Example 32. The data are also shown in Tables 17-18.

TABLE 17

Compound:

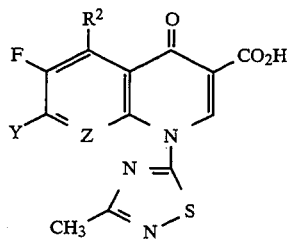

| Compound No. | Group R² | Y | Z | Property | Melting point (°C.) | ¹H-NMR | Solvent |
|---|---|---|---|---|---|---|---|
| 69 | H | H₂N—[piperidine-S]—N— .HCl | N | Pale yellow solid | Colored from 220, decomposed | [DMSO-d₆] δ; 2.26(brs, 1H), 2.40(brs, 1H), 2.64(s, 3H), 4.07–4.25(br, 4H), 8.19(d, J=13Hz, 1H), 8.0–8.7(br, 3H), 9.73(s, 1H) | MeCN Et₃N ↓ Hydrochloric acid |
| 70 | H | MeN[piperazine]N— .HCl | N | Colorless solid | Colored from 250, decomposed | [DMSO-d₆] δ; 2.65(s, 1H), 2.84(s, 3H), 8.35(d, J=13Hz, 1H), 9.75(s, 1H), 11.0–11.5(br, 1H) | " |

TABLE 18

| Compound No. | Group R² | Y | Z | Property | Melting point (°C.) | ¹H-NMR | Solvent |
|---|---|---|---|---|---|---|---|
| 71 | H | HN[piperazine]N— .HCl | N | Yellow solid | Colored from 260, decomposed | [DMSO-d₆]δ; 2.65(s, 3H), 4.09(brs, 4H), 8.33(d, J=13Hz, 1H), 9.75(s, 1H) | MeCN Et₃N ↓ Hydrochloric acid |
| 72 | H | H₂N—[Me-piperidine]—N— .HCl Cis (—) | N | Pale yellow solid | Colored from 190, decomposed | [DMSO-d₆] δ; 1.16(d, J=7Hz, 3H), 2.64(s, 3H), 2.80(brs, 1H), 3.74–4.04(br, 2H), 8.18(d, J=13Hz, 1H), 9.72(s, 1H) | MeCN Et₃N ↓ Hydrochloric acid |

EXAMPLE 34

Ethyl 6,7-difluoro-1-(3-methyl-1,2,4-thiadiazol-5-yl)-1,4-dihydro-4-oxoquinoline-3-carboxylate (Compound No.73)

A mixture of ethyl 2,4,5-trifluorobenzoylacetate (3.7 g), ethyl orthoformate (3.9 ml) and acetic anhydride (4.3 ml) was stirred at 135° C. for 3 hours. After the solvent was removed in vacuo, the residue was added with chloroform (20 ml) and ethanol (10 ml). 3-Methyl-5-amino-1,2,4-thiadiazole (1.73 g) was added thereto for allowing to react for 15 hours at the same temperature. The solvent was removed. The residue was purified by chromatography on silicagel(chloroform/ethyl acetate 1:1 as an eluent). An yellow oil (4.9 g) was obtained. To a solution of this oily compound (4.5 g) in N,N-dimethylformamide (60 ml), 490 mg of sodium hydride (60% in oil) was added . Then the solution was stirred for 5 minutes at 100° C. The solvent was removed. The residue was added with chloroform and water, for extracting an organic layer, followed by evaporation. The precipitated solid was collected and washed with ethanol, ether and n-hexane, successively. The title compound No. 73 was obtained as a pale brown solid (2.4 g).

Melting point: 157°–159° C. ¹H-NMR(CDCl₃) δ; 1.42(t,J=7 Hz,3H), 2.78(s,3H), 4.43(q,J=7 Hz,2H), 8.17–8.32(m,2H), 8.77(s,1H)

EXAMPLE 35

6,7-Difluoro-1-(3-methyl-1,2,4-thiadiazol-5-yl)-1,4-dihydro- 4-oxoquinoline-3-carboxylic acid (Compound No.74)

Compound No.73 (1.2 g) obtained in Example 34 was dissolved in a mixture of tetrahydrofuran (40 ml) and HCl (10 ml). The solution was reacted at 100° C. for 40 minutes. After evaporation, to the residue was added water, and the solid matter was collected by filtration, followed by washing with water, ethanol, ether and n-hexane, successively. The title compound No. 74 was obtained as a pale brown solid (0.9 g).

Melting point: 235°–238° C. $^1$H-NMR(DMSO-d$_6$) δ; 2.69(s,3H), 8.06(dd,J=7 Hz,J=12 Hz,1H), 8.32(dd,J=9 Hz,J=10 Hz,1H), 9.04(s,1H)

EXAMPLE 36

6-Fluoro-7-(3-aminoazetidin-1-yl)-1-(3-methyl-1,2,4-thiadiazol-5-yl)-1,4-dihydro-4-oxoquinoline-3-carboxylicacid hydrochloride (Compound No. 75)

Compound No.74 (90 mg) obtained in Example 35 was added to acetonitrile (4 ml), to which triethylamine (0.12 g) and 3-aminoazetidine dihydrochloride (54 mg) were further added for allowing to react at 80° C. for 60 minutes. After cooling, the precipitate was filtrated and washed with ethanol, ether and n-hexane, successively to obtain a pale yellow solid (43 mg). A 20 mg portion was taken and added to a mixture of tetrahydrofuran (2 ml) and 6N-HCl (0.5 ml), and stirred for 5 minutes. The precipitate was collected by filtration and washed with water, ethanol, ether and n-hexane successively. The title compound No. 75 was obtained as a pale yellow solid (15 mg).

Melting point: Colored and decomposed at 270° C. or more. $^1$H-NMR(DMSO-d$_6$) δ; 2.69(s,3H), 4.16(br,3H), 4.42(brs,2H), 6.67(d,J=8 Hz,1H), 7.92(d,J=13 Hz,1H), 8.5–8.7(brs,3H), 8.89(s,1H)

EXAMPLE 37

Compound No.76 listed in Table 19 was prepared in a similar manner to Example 36. The data are also shown in Table 19.

was removed and the residue was purified by chromatography on silicagel(chloroform as an eluent). The title compound No. 77 was obtained as a colorless solid (770 mg).

Melting point: 139–141.5° C. $^1$H-NMR(CDCl$_3$) δ; 0.97 and 1.18(t,J=7 Hz,3H), 2.47 and 2.51(s,3H), 4.05–4.3(m,2H), 7.3 and 7.43(d,J=6.8 Hz,1H), 8.72 and 8.82(d,J=12.4 Hz,1H)

EXAMPLE 39

Ethyl 7-chloro-6-fluoro-1-(4-methyl-1,2,5-oxadiazol-3-yl)-1,4-dihydro-4-oxo-1,8-naphthyridine-3-carboxylate (Compound No.78)

To a solution of compound No.77 (0.7 g) obtained in Example 38 in tetrahydrofuran (30 ml), 0.074 g of sodium hydride (60% in oil) was added with ice cooling. Then the solution was stirred for 4 hours at room temperature. The solvent was removed. After addition of aqueous 5% citric acid solution (20 ml), extraction was carried out with chloroform (50 ml). The chloroform was evaporated and the residue was purified by chromatography on silicagel (chloroform/ethyl acetate 1:1 as an eluent). The title compound No. 78 was obtained as a pale yellow solid (0.41 g).

Melting point: 211°–216° C. $^1$H-NMR(CDCl$_3$) δ; 1.40(t,J=7 Hz,3H), 2.41(s,3H), 4.41(q,J=7 Hz,2H), 8.49(d,J=7.8 Hz,1H), 8.66(s,1H)

EXAMPLE 40

7-Chloro-6-fluoro-1-(4-methyl-1,2,5-oxadiazol-3-yl)-1,4-dihydro-4-oxo-1,8-naphthyridine-3-carboxylic acid (Compound No.79)

TABLE 19

Compound:

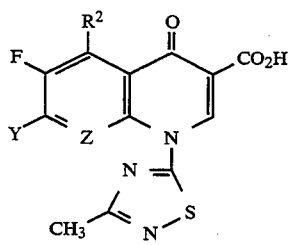

| Compound No. | Group R² | Y | Z | Property | Melting point (°C.) | ¹H-NMR | Solvent |
|---|---|---|---|---|---|---|---|
| 76 | H | H₂N—[cyclohexyl with Me]—N— ·HCl  Cis (−) | C\|H | Pale yellow solid | Colored from 159, decomposed | [DMSO-d₆] δ; 1.09(brs, 3H), 2.51–2.71(m, 1H), 2.71(s, 3H), 3.08–3.90(m, 5H), 6.72(d, J=7Hz, 1H), 7.92(d, J=14Hz, 1H), 8.2–8.6(br, 3H) 8.92(s, 1H) | MeCN Et₃N ↓ Hydrochloric acid |

EXAMPLE 38

Ethyl 3-(4-methyl-1,2,5-oxadiazol-3-ylamino)-2-(2,6-dichloro-5-fluoronicotinoyl)acrylate (Compound No.77)

A mixture of ethyl 2,6-dichloro-5-fluoronicotinoylacetate (1.4 g), ethyl orthoformate (1.3 ml) and acetic anhydride (1.4 ml) was stirred at 130° C. for 17 hours. After the solvent was removed in vacuo, a solution of 3-amino-4-methyl-1,2,5-oxadiazole (545 mg) in chloroform (5 ml) was added to the residue. The mixture was stirred at room temperature for 24 hours. The solvent Compound No. 78 (30 mg) obtained in Example 39 was dissolved in acetic acid (2 ml) and 6N-HCl (0.5 ml). The solution was stirred at 100° C. for 0.5 hour. After cooling and addition of water (10 ml), the precipitate was filtrated and washed with ethanol and ether. The title compound No. 79 was obtained as a colorless solid (5 mg).

Melting point: 242°–247° C. $^1$H-NMR(DMSO-d$_6$) δ; 2.33(s,3H), 8.77(d,J=8 HZ,1H), 9.09(s,1H)

EXAMPLE 41

6-Fluoro-7-(4-methylpiperazin-1-yl)-1-(4-methyl-1,2,5-oxadiazol-3-yl)-1,4-dihydro-4-oxo-1,8-naphthyridine-3-carboxylic acid hydrochloride (Compound No.80)

A mixture of compound No.78 (0.15 g)obtained in Example 40, triethylamine (40 mg) and N-methylpiperazine (70 mg) in acetonitrile (5 ml) was stirred at 50° C. for 20 minutes. After the solvent was removed, 1 ml of 6N-HCl and 1 ml of acetic acid were added, then stirred at 100° C. for 1 hour. After the solvent was removed in vacuo, ethanol(5 ml) was added to the residue. The precipitate was collected by filtration and washed with ethanol and ether. The title compound No. 80 was obtained as a colorless solid (0.16 g).

Melting point: 254°–258° C. $^1$H-NMR(DMSO-$d_6$) δ; 2.31(s,3H), 2.74(s,3H), 3.08(brs,2H), 3.3–3.6(m,4H), 4.18(brs,2H), 8.29(d,J=13.2 Hz,1H), 9.00(s,1H)

EXAMPLE 42

Compounds Nos. 81–89 listed in Tables 20-22 were synthesized in a similar manner to Example 41. The data are also shown in Tables 20-22.

TABLE 20

Compound:

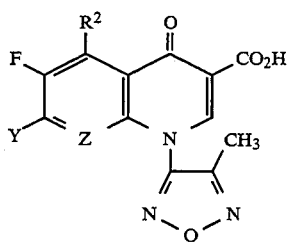

| Compound No. | Group R² | Y | Z | Property | Melting point (°C.) | ¹H-NMR | Solvent |
|---|---|---|---|---|---|---|---|
| 81 | H | (S) H₂N-⟨pyrrolidinyl⟩-N— .HCl | N | Pale yellow solid | Colored from 245, decomposed from 272 | [DMSO-$d_6$] δ; 2.0–2.4(m, 2H), 2.34(s, 3H), 3.2–4.1(m, 5H), 8.13(d, J=12Hz, 1H), 8.37(brs, 3H), 8.92(s, 1H) | Et₃N/CH₃CN ↓ AcOH, 6N—HCl |
| 82 | H | H₂N-⟨pyrrolidinyl-Me⟩-N— Cis(−).HCl | N | Pale yellow solid | Colored from 255, decomposed from 294 | [DMSO-$d_6$] δ; 1.08(d, J=6.8Hz, 3H), 2.34(s, 3H), 2.4–2.7(br, 1H), 3.4–4.2(m, 3H), 8.14(d, J=12.2Hz, 1H), 8.37(brs, 3H), 8.92(s, 1H) | " |

TABLE 21

| Compound No. | Group R² | Y | Z | Property | Melting point (°C.) | ¹H-NMR | Solvent |
|---|---|---|---|---|---|---|---|
| 83 | H | Me, H₂N-⟨pyrrolidinyl⟩-N— .HCl | N | Colorless solid | 300 or more | [DMSO-$d_6$] δ; 1.44(s, 3H), 1.9–2.4(m, 2H), 2.34(s, 3H), 3.4–4.3(m, 4H), 8.13(d, J=14.7Hz, 1H), 8.56(brs, 3H), 8.92(s, 1H) | Et₃N/CH₃CN ↓ AcOH, 6N—HCl |
| 84 | H | HO-⟨pyrrolidinyl⟩-N— (S) | N | Colorless solid | 224 ∫ 226.5 | [DMSO-$d_6$] δ; 1.9(brs, 2H), 2.31(s, 3H), 3.9(brs, 1H), 4.3(brs, 1H), 5.05(brs, 1H), 8.06(d, J=12.2Hz, 1H), 8.91(s, 1H) | " |
| 85 | H | HN⟨piperazinyl⟩N— .HCl | N | Pale yellow solid | Decomposed from 276 | [DMSO-$d_6$] δ; 2.32(s, 3H), 3.18(s, 4H), 3.81(s, 4H), 8.24(d, J=13.2Hz, 1H), 8.98(s, 1H), 9.59(brs, 1H), 9.79(brs, 1H) | " |

TABLE 21-continued

| Compound No. | Group R² | Y | Z | Property | Melting point (°C.) | ¹H-NMR | Solvent |
|---|---|---|---|---|---|---|---|
| 86 | H | (1R, 4R) HN⟨⟩N— ·HCl | N | Colorless solid | Decomposed from 292 | [DMSO-d₆] δ; 1.9–2.2(m, 2H), 2.32(s, 3H), 4.45(s, 1H), 8.21(d, J=13Hz, 1H), 8.96(s, 1H), 8.95(brs, 2H) | " |

TABLE 22

| Compound No. | Group R² | Y | Z | Property | Melting point (°C.) | ¹H-NMR | Solvent |
|---|---|---|---|---|---|---|---|
| 87 | H | (1R, 4R) MeN⟨⟩N— ·HCl | N | Colorless solid | Decomposed from 297 | [DMSO-d₆] δ; 2.1–2.4(m, 2H) 2.33(s, 3H), 2.83(s, 3H), 3.0–3.2(m, (1H) 3.5–3.7(m, 1H), 4.38(s, 1H), 8.22(d J=11.7Hz, 1H), 8.96(s, 1H), 10.4(brs, 1H) | Et₃N/CH₃CN ↓ AcOH, 6N—HCl |
| 88 | H | H₂N—⟨⟩N— ·HCl | N | Colorless solid | Decomposed from 241 | [DMSO-d₆] δ; 2.31(s, 3H), 3.57(brs, 2H), 3.72(brs, 2H), 8.14(d, J=10.2Hz, 1H), 8.44(brs, 2H), 8.65(brs, 1H), 8.93(s, 1H) | " |
| 89 | H | H₂N⌒S— ·HCl | N | Colorless solid | 218 ∫ 225 | [DMSO-d₆] δ; 2.33(s, 3H), 2.85(brs, 2H), 3.18(brs, 2H), 8.12(brs, 3H), 8.47(d, J=8.8Hz, 1H), 9.18(s, 1H) | " |

EXAMPLE 43

Ethyl 3-(4-methyl-1,2,5-oxadiazol-3-ylamino)-2-(2,4,5-trifluorobenzoyl)acrylate (Compound No.90)

A mixture of ethyl 2,4,5-trifluorobenzoylacetate (2.46 g), ethyl orthoformate (2.6 ml) and acetic anhydride (2.8 ml) was stirred at 130° C. for 6 hours. After the solvent was removed in vacuo, a solution of 3-amino-4-methyl-1, 2,5-oxadiazole (1.04 g) in chloroform (10 ml) was added to the residue. The mixture was stirred at room temperature for 24 hours, then the solvent was removed. The residue was purified by chromatography on silicagel (chloroform as an eluent). The title compound No. 90 was obtained as a colorless solid (1.95 g).

Melting point: 104°–107° C. ¹H-NMR(CDCl₃) δ; 1.05 and 1.20(t,J=7 Hz,3H), 2.45 and 2.48(s,3H), 4.1–4.3(m,2H), 6.85–7.0(m,1H), 7.3–7.41 and 7.48–7.6(m,1H), 8.39 and 8.69(q,J=12 Hz,1H)

EXAMPLE 44

Ethyl 6,7-difluoro-1-(4-methyl-1,2,5-oxadiazol-3-yl)-1,4-dihydro-4-oxoquinoline-3-carboxylate (Compound No.91)

To a solution of compound No.90 (1.9 g) obtained in Example 43 in tetrahydrofuran (50 ml), 216 mg of sodium hydride (60% in oil) was added. Then the solution was stirred for 6 hour at the room temperature. The solvent was removed and the residue was added with aqueous 5% citric acid solution (30 ml), followed by extraction with chloroform (50 ml), and evaporation. The residue was purified by chromatography on silicagel (chloroform/ethyl acetate 1:1 as an eluent). The title compound No. 91 was obtained as a colorless solid (1.18 g).

Melting point: 178°–180.5° C. ¹H-NMR(CDCl₃) δ; 1.40(t,J=7 Hz,3H), 2.41(s,3H), 4.39(q,J=7 Hz,2H), 6.81(dd,J=10.2 Hz,J=5.8 Hz,1H), 8.30(dd,J=9.8 Hz,J=8.8 Hz,1H), 8.39(s,1H)

EXAMPLE 45

6,7-Difluoro-1-(4-methyl-1,2,5-oxadiazol-3-yl)-1,4-dihydro-4-oxoquinoline-3-carboxylic acid (Compound No.92)

Compound No.91 (0.1 g) obtained in Example 44 was dissolved in acetic acid (3 ml) and 6N-HCl (1 ml). The solution was stirred at 100° C. for 2 hours. After cooling, the precipitate was filtrated and washed with water, ethanol and ether. The title compound was obtained as colorless solid(60 mg).

Melting point: 238–241° C. ¹-NMR(DMSO-d₆) δ; 2.33(s,3H), 7.78(dd,J=11.2 Hz,J=6.3 Hz,1H), 8.34(dd,J=10.3 Hz,J=8.3 Hz,1H), 9.16(s,1H)

EXAMPLE 46

Compound Nos. 93–95 listed in Tables 23 and 24 were synthesized in a similar manner to Example 11, proceeding from the corresponding compound No.92 obtained in Example 45. The data are also shown in Tables 23–24.

TABLE 23

Compound:

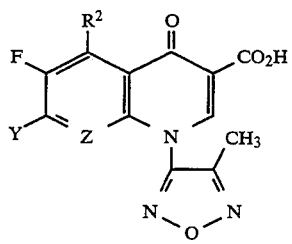

| Compound No. | Group R² | Y | Z | Property | Melting point (°C.) | ¹H-NMR | Solvent |
|---|---|---|---|---|---|---|---|
| 93 | H | (S) H₂N–[pyrrolidinyl]–N— .HCl | C\|H | Pale yellow solid | Decomposed from 292 | [DMSO-d₆] δ; 2.0–2.3(m, 2H), 2.36(s, 3H), 3.74–4.0(m, 2H), 598(d, J=6.8Hz, 1H), 7.93(d, J=14Hz, 1H), 8.37(brs, 3H), 8.97(s, 1H) | Et₃N/CH₃CN ↓ AcOH, 6N—HCl |
| 94 | H | .Cis (−) H₂N–[pyrrolidinyl with Me]–N— .HCl | C\|H | Pale yellow solid | 274 ∫ 279 | [DMSO-d₆] δ; 1.08(d, J=6.8Hz, 3H), 2.36(s, 3H), 2.5–2.7(m, 1H), 3.5–4.0(m, 4H), 5.95(d, J=7.3Hz, 1H), 7.93(d, J=14Hz, 1H), 8.1–8.8(br, 3H) 8.97(s, 1H) | " |

TABLE 24

| Compound No. | Group R² | Y | Z | Property | Melting point (°C.) | ¹H-NMR | Solvent |
|---|---|---|---|---|---|---|---|
| 95 | H | HN–[piperazinyl]–N— .HCl | C\|H | Colorless solid | 278 ∫ 285 | [DMSO-d₆] δ; 2.34(s, 3H), 3.23(s, 4H), 3.44(s, 4H), 6.66(d, J=6.8Hz, 1H), 8.04(d, J=12.7Hz, 1H), 9.06(s, 1H), 9.52(brs, 2H) | Et₃N/CH₃CN ↓ AcOH, 6N—HCl |

EXAMPLE 47

Ethyl 3-(1,2,4-triazol-4-ylamino)-2-(2,4,5-trifluorobenzoyl)acrylate (Compound No.96)

A mixture of ethyl 2,4,5-trifluorobenzoylacetate (4.29 g), ethyl orthoformate (5.2 ml) and acetic anhydride (5.6 ml) was stirred at 130° C. for 6 hours. After the solvent was removed in vacuo, a solution of 4-amino-1,2,4-triazole (1.77 g) and ethanol (5 ml) in chloroform (30 ml) was added to the residue. The mixture was stirred at room temperature for 6 hours. The solvent was removed, the residue was added with 100 ml of hexane, then the solution was stirred for 1 hour. The precipitate was filtrated. The title compound No. 96 was obtained as a colorless solid (6.2 g).

Melting point: 239°–240° C. ¹H-NMR(CDCl₃) δ; 1.0–1.2(m,3H), 4.14(q,J=7 Hz,2H), 6.85–7.1(m,1H), 7.3–7.6(m,1H), 8.18(brs,1H), 8.46(s,2H)

EXAMPLE 48

Ethyl 6,7-difluoro-1-(1,2,4-triazol-4-yl)-1,4-dihydro-4-oxoquinoline-3-carboxylate (Compound No.97)

A solution of compound No.96 (6.2 g) obtained in Example 47 and anhydrous potassium carbonate (2.5 g) in N,N-dimethylformamide (20 ml) was stirred for 4 hours at 90° C. The solvent was removed in vacuo. After addition of water, the precipitate was filtrated and washed with water, ethanol and ether successively. The title compound No. 97 was obtained as a pale green solid (3.7 g).

Melting point: 269°–274° C. ¹H-NMR(DMSO-d₆) δ; 1.26((t,J=7 Hz,3H), 4.22(q,J=7 Hz,2H), 6.9(dd,J=11 Hz,J=6.4 Hz,1H), 8.14(dd,J=10.2 Hz,J=8.3 Hz,1H), 9.01(s,1H),9.20(s,2H)

EXAMPLE 49

6,7-Difluoro-1-(1,2,4-triazol-4-yl)-1,4-dihydro-4-oxoquinoline-3-carboxylic acid (Compound No.98)

Compound No.97 (3.0 g) obtained in Example 48 was dissolved in a mixture of tetrahydrofuran (120 ml) and 6N-HCl (30 ml). The solution was stirred at reflux temperature for 20 minutes. After cooling, 200 ml of water was added. The precipitate was filtrated and washed with ethanol, ether and hexane. The title compound No. 98 was obtained as a colorless solid (1.6 g).

Melting point: 270° C. decomposed ¹H-NMR(DMSO-d₆) δ; 7.09(dd,J=11 Hz,J=6 Hz,1H), 8.36(dd,J=10 Hz,J=8 Hz,1H), 9.18(s,2H), 9.34(s,1H)

EXAMPLE 50

6-Fluoro-7-(4-methylpiperazin-1-yl)-1-(1,2,4-triazol-4-yl)-1,4-dihydro-4-oxoquinoline-3-carboxylic acid (Compound No.99)

A mixture of compound No.98 (50 mg) obtained in Example 49 and N-methylpiperazine (40 mg) in acetonitrile (3 ml) was stirred at 80° C. for 60 minutes. After the solvent was removed, ethanol was added to the residue. The precipitate was filtrated and washed with ethanol and ether successively. The title compound No. 99 was obtained as a yellow solid (43 mg).

Melting point: 270° C. decomposed $^1$H-NMR(DMSO-$d_6$) δ; 2.20(s,3H), 2.43(brs,4H), 3.13(brs,4H), 5.83(d,J=7 Hz,1H), 8.00(d,J=14 Hz,1H), 9.21(s,2H), 9.26(s,1H)

EXAMPLE 51

Compound Nos. 100–103 listed in Tables 25 and 26 were synthesized in a similar manner to Example 50. The data are also shown in Tables 25 and 26.

EXAMPLE 52

Ethyl 3-(1,2,4-triazol-4-ylamino)-2-(2,6-dichloro-5-fluoronicotinoyl)acrylate (Compound No.104)

A mixture of ethyl 2,6-dichloro-5-fluoronicotinoylacetate (4.2g), ethyl orthoformate (3.9 ml) and acetic anhydride (4.3 ml) was stirred at 130° C. for 2 hours. After the solvent was removed in vacuo, a solution of 4-amino-1,2,4-triazole (1.26 g) in chloroform (20 ml) was added to the residue. The mixture was stirred at room temperature for 4 hours. The solvent was removed and the residue was added with isopropylether. The precipitate was filtrated. The title compound No. 104 was obtained as a yellow solid (5.5 g).

Melting point: 89°–95° C. $^1$H-NMR(CDCl$_3$) δ; 1.27(t,J=7 Hz,3H), 4.24(q,J=7 Hz,2H), 8.6(d,J=7.6 Hz,1H), 9.04(s,2H), 9.22(s,1H)

TABLE 25

Compound:

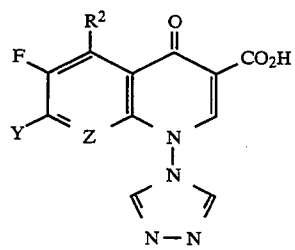

| Compound No. | Group R² | Y | Z | Property | Melting point (°C.) | ¹H-NMR | Solvent |
|---|---|---|---|---|---|---|---|
| 100 | H | HN⌒N— (piperazine) | C\|H | Pale yellow solid | 300 or more | [DMSO-d₆] δ; 2.81(brs, 4H), 3.05(brs, 4H), 5.79(d, J=7Hz, 1H), 7.98(d, J=14Hz, 1H), 9.22(s, 2H), 9.25(s, 1H) | CH₃CN Et₃N |
| 101 | H | H₂N–◇–N— (azetidine) | C\|H | Colorless solid | 300 or more | [DMSO-d₆] δ; 4.21(brs, 2H) 5.11(d, J=7Hz, 1H), 7.87(d, J=13Hz, 1H), 9.15(s, 2H), 9.20(s, 1H) | CH₃CN Et₃N |

TABLE 26

| Compound No. | Group R² | Y | Z | Property | Melting point (°C.) | ¹H-NMR | Solvetn |
|---|---|---|---|---|---|---|---|
| 102 | H | H₂N–(piperidine)–N— S-form | C\|H | Brown solid | 300 or more | [DMSO-d₆] δ; 1.59–2.01(m, 2H), 2.76–3.19(m, 5H), 5.27(d, J=7Hz, 1H), 7.86(d, J=14Hz, 1H), 9.09(s, 1H), 9.23(s, 2H) | CH₃CN |
| 103 | H | H₂N–(piperidine with H₃C)–N— Cis (−) | C\|H | Pale yellow solid | 300 or more | [DMSO-d₆] δ; 0.96(d, J=7Hz, 3H), 2.07–2.22(m, 1H), 3.17–3.52(m, 5H), 5.25(d, J=7Hz, 1H), 7.85(d, J=14Hz, 1H), 9.13(s, 1H), 9.22(s, 2H) | CH₃CN Et₃N |

EXAMPLE 53

Ethyl 7-chloro-6-fluoro-1-(1,2,4-triazol-4-yl)-1,4-dihydro-4-oxo-1,8-naphthyridine-3-carboxylate (Compound No.105)

A solution of compound No.104 (0.95 g) obtained in Example 52 and sodium hydrogencarbonate (0.21 g) in N,N-dimethylformamide (5 ml) was stirred for 1 hour at 100° C. The solution was removed in vacuo. After addition of water to the residue, the precipitate was filtrated and washed with water, ethanol and ether successively. The title compound No. 105 was obtained as a pale yellow solid (0.52 g).

Melting point: 257° C. decomposed $^1$H-NMR(CDCl$_3$) δ; 1.08(t,J=7 Hz,3H), 4.11(q,J=7 Hz,2H), 7.47(d,J=6.8 Hz,1H), 8.27(s,1H), 8.47(s,2H)

EXAMPLE 54

7-Chloro-6-fluoro-1-(1,2,4-triazol-4-yl)-1,4-dihydro-4-oxo-1,8-naphthyridine-3-carboxylic acid (Compound No.106)

Compound No.105 (1.0 g) obtained in Example 53 was dissolved in acetic acid (40 ml) and 6N-HCl (10 ml). The solution was stirred at 100° C. for 0.5 hour. After cooling, water (100 ml) is added thereto, and the precipitate was filtrated and washed with ethanol and ether successively. The title compound No. 106 was obtained as a pale yellow solid (0.48 g).

Melting point: 230° C. decomposed $^1$H-NMR( DMSO-d$_6$) δ; 8.77(d,J=8 Hz,1H), 9.03(s,2H), 9.44(s,1H)

EXAMPLE 55

6-Fluoro-7-(4-methylpiperazin-1-yl)-1-(1,2,4-triazol-4-yl)-1,4-dihydro-4-oxo-1,8-naphthyridine-3-carboxylic acid (Compound No.107)

A mixture of compound No.106 (30 mg) obtained in Example 54 and N-methylpiperazine (20 mg) in acetonitrile (2 ml) was stirred at 80° C. for 60 minutes. After the solvent was removed, ethanol (5 ml) was added to the residue. The precipitate was filtrated and washed with ethanol and ether successively. The title compound No. 107 was obtained as a colorless solid (7 mg).

Melting point: 271° C. decomposed $^1$H-NMR(DMSO-d$_6$) δ; 2.32(s,3H), 3.06(brs,4H), 3.59(brs,4H), 8.21(d,J=13 Hz,1H), 9.01(s,2H), 9.33(s,1H)

EXAMPLE 56

Compound Nos. 108–110 listed in Table 27 were prepared in a similar manner to Example 55. The data are also shown in Table 27.

TABLE 27

Compound:

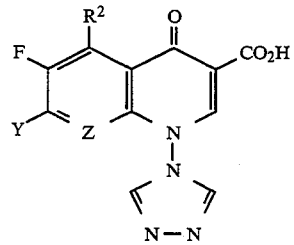

| Compound No. | Group R$^2$ | Y | Z | Property | Melting point (°C.) | $^1$H-NMR | Solvent |
|---|---|---|---|---|---|---|---|
| 108 | H | H$_2$N–, Me (Cis (−)) N— | N | Colorless solid | Decomposed from 220 | [DMSO-d$_6$] δ; 0.96(brs. 3H), 2.11–2.32(m, 1H), 2.83–3.93(m, 5H), 8.04(d, J=13Hz, 1H), 9.00(s, 2H), 9.22(s, 1H) | CH$_3$CN Et$_3$N |
| 109 | H | H$_2$N–, S N— | N | Pale brown solid | Decomposed from 238 | [DMSO-d$_6$] δ; 1.58–2.01(m, 2H), 2.73–3.95(m, 5H), 8.05(d, J=12Hz, 1H), 8.99(s, 2H), 9.23(s, 1H) | CH$_3$CN Et$_3$N |
| 110 | H | HN  N— | N | Pale brown solid | Decomposed from 240 | [DMSO-d$_6$] δ; 2.70(brs, 4H) 3.64(brs, 4H), 8.14(d, J=14Hz, 1H), 9.01(s, 2H), 9.29(s, 1H) | CH$_3$CN Et$_3$N |

EXAMPLE 57

Ethyl 3-(1,2,5-thiadiazol-3-yl-methylamino)-2-(2,6-dichloro-5-fluoronicotinoyl)acrylate (Compound No.111)

A mixture of ethyl 2,6-dichloro-5-fluoronicotinoylacetate (0.56 g), ethyl orthoformate (0.5 ml) and acetic anhydride (0.57 ml) was stirred at 130° C. for 3 hours. After the solvent was removed in vacuo, a solution of 3-aminomethyl-1, 2,5-thiadiazole (0.24 g) in benzene (5 ml) and methanol (2 ml) was added to the residue. The mixture was stirred at room temperature for 0.5 hour.

The solvent was removed, the residue was added with isopropylether (10 ml), and the precipitate was filtrated. The title compound No. 111 was obtained as a pale yellow solid (573 mg).

Melting point: 108°–110° C. $^1$H-NMR(CDCl$_3$) δ; 0.89 and 1.06(t,J=7 Hz, 3H), 3.9–4.15(m,2H), 4.97(d,J=5.8 Hz,2H), 7.37 and 7.43(d,J=7 Hz, 1H), 8.35 and 8.39(d,J=14 Hz,1H), 8.56 and 8.58(s, 1H)

EXAMPLE 58

Ethyl 7-chloro-6-fluoro-1-(1,2,5-thiadiazol-3-ylmethyl)-1,4-dihydro-4-oxo-1,8-naphthyridine-3-carboxylate (Compound No.112)

To a solution of compound No.111 (0.55 g) obtained in Example 57 in tetrahydrofuran (20 ml), 56 mg of sodium hydride (60% in oil) was added. Then the solution was stirred for 0.5 hour at room temperature. The solvent was evaporated, an aqueous 5% citric acid solution (10 ml) was added thereto, and extracted with chloroform (50 ml). The extract was dried over Na$_2$SO$_4$, and the solvent was removed. Isopropylether (10 ml) was added to the residue, and the precipitate was filtrated. The title compound No. 112 was obtained as a colorless solid (425 mg).

Melting point: 175–177° C. $^1$H-NMR(CDCl$_3$) δ; 1.41(t,J=7 Hz,3H), 4.41(q,J=7 Hz,2H), 5.79(s,2H), 8.45(d,J=7.3 Hz,1H), 8.73(s,1H), 8.83(s,1H)

EXAMPLE 59

7-Chloro-6-fluoro-1-(1,2,5-thiadiazol-3-ylmethyl)-1,4-dihydro-4-oxo-1,8-naphthyridine-3-carboxylic acid (Compound No.113)

Compound No.112 (0.4 g) obtained in Example 158 was dissolved in acetic acid (4.5 ml) and 6N-HCl (1.5 ml). The solution was stirred at 100° C. for 2 hours. After cooling, the precipitate was filtrated and washed with water, ethanol and ether. The title compound No. 113 was obtained as a pale yellow solid (0.33 g).

Melting point: 231°–232.5° C. $^1$H-NMR(DMSO-d$_6$) δ; 6.13(s,2H), 8.72(d,J=7.8 Hz,1H), 8.93(s,1H), 9.7(s,1H)

EXAMPLE 60

6-Fluoro-7-(piperazin-1-yl)-1-(1,2,5-thiadiazole-3-ylmethyl)-1,4-dihydro-4-oxo-1,8-naphthyridine-3-carboxylic acid (Compound No.114)

A mixture of compound No.113 (70 mg) obtained in Example 59, piperazine (26 mg) triethylamine (60 mg) in acetonitrile (2 ml) was stirred at 80° C. for 90 minutes. After cooling, the precipitate was filtrated and washed with ethanol and ether successively. The title compound No. 114 was obtained as a pale orange solid (71 mg).

Melting point: 219.5°–223° C. $^1$H-NMR(DMSO-d$_6$) δ; 2.64(s,4H), 3.57(s,4H), 5.99(s,2H), 8.05(d,J=14 Hz,1H), 8.91(s,1H), 9.25(s,1H)

EXAMPLE 61

Compounds Nos. 115–116 listed in Table 28 were prepared in a similar manner to Example 60. The data are also shown in Table 28.

TABLE 28

Compound:

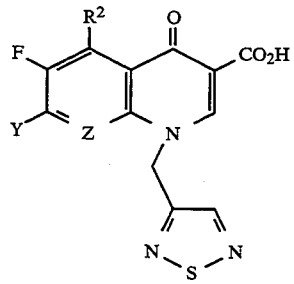

| Compound No. | Group R$^2$ | Y | Z | Property | Melting point (°C.) | $^1$H-NMR | Solvent |
|---|---|---|---|---|---|---|---|
| 115 | H | (S) H$_2$N–⟨pyrrolidinyl⟩–N— | N | Pale yellow solid | 208 ∫ 213 | [DMSO-d$_6$] δ; 1.5–1.7(br, 1H), 1.7–2.1(br, 1H), 2.9–3.2(m, 2H), 5.98(s, 2H), 7.95(d, J=13.7Hz, 1H), 8.91(s, 1H), 9.18(s, 1H) | Et$_3$N/MeCN |
| 116 | H | H$_2$N–⟨pyrrolidinyl-Me⟩–N— Cis (−) | N | Pale yellow solid | 178 ∫ 184 | [DMSO-d$_6$] δ; 0.98(d, J=6.8Hz, 3H), 2.2(brs, 1H), 3.1–3.7(m, 5H), 6.00((s, 2H), 7.98(d, J=13Hz, 1H), 8.94(s, 1H), 9.21(s, 1H) | " |

EXAMPLE 62

Ethyl 3-(1,2,5-thiadiazol-3-ylmethylamino)-2-(2,4,5-trifluorobenzoyl)acrylate (Compound No.117)

A mixture of ethyl 2,4,5-trifluorobenzoylacetate (492 mg), ethyl orthoformate (0.5 ml) and acetic anhydride (0.57 ml) was stirred at 130° C. for 3 hours. After the solvent was removed in vacuo, a solution of 3-aminomethyl-1,2,5-thiadiazole (0.24 g) in benzene (5 ml) was added to the residue. The mixture was stirred at room temperature for 24 hours. The precipitate was filtrated. The title compound No. 117 was obtained as a pale yellow solid (530 mg).

Melting point: 167.5°-170° C. $^1$H-NMR(CDCl$_3$) δ; 0.96 and 1.08(t,J=7 Hz,3H), 3.95-4.15(m,2H), 4.91(d,J=6.2 Hz,2H), 6.8-6.95(m,1H), 7.15~7.4(m,1H), 8.14 and 8.23(d,J=13.9 Hz,1H), 8.54 and 8.56(s,1H)

EXAMPLE 63

Ethyl 6,7-difluoro-1-(1,2,5-thiadiazol-3-ylmethyl)-1,4-dihydro-4-oxoquinoline-3-carboxylate (Compound No.118)

To a solution of compound No.117 (507 mg) obtained in Example 62 in tetrahydrofuran (25 ml), 55 mg of sodium hydride (60% in oil) was added. The solution was stirred for 20 minutes at the room temperature, and the solvent was removed. After addition of an aqueous 5% citric acid solution (10 ml), extraction was carried out with chloroform (50 ml). The organic phase was dried over Na$_2$SO$_4$ and evaporated. After addition of hexane (10 ml) to the residue, the precipitate was filtrated. The title compound No. 118 was obtained as a pale yellow solid (0.44 g).

Melting point: 198°-201° C. 1H-NMR(CDCl$_3$) δ; 1.40(t,J=7 Hz,3H), 4.39(q,J=7 Hz,2H), 5.62(s,2H), 7.29(dd,J=11 Hz,J=6 Hz,1H), 8.27(dd,J=10 Hz,J=9 Hz, 1H), 8.56(s,1H), 8.67(s,1H)

EXAMPLE 64

6,7-Difluoro-1-(1,2,5-thiadiazol-3-ylmethyl)-1,4-dihydro-4-oxoquinoline-3-carboxylic acid (Compound No.119)

Compound No.118 (0.42 g) obtained in Example 63 was dissolved in acetic acid (6 ml) and 6N-HCl (2 ml). The solution was stirred at 100° C. for 2 hours. After cooling, the precipitate was filtrated and washed with water, ethanol and ether. The title compound No. 119 was obtained as a colorless solid (0.325 g).

Melting point: 278°-281.5° C. $^1$H-NMR(DMSO-d$_6$) δ; 6.19(s,2H), 8.1-8.4(m,2H), 8.97(s,1H), 9.31(s,1H)

EXAMPLE 65

Compounds Nos. 120-122 listed in Table 29 were synthesized in a similar manner to Example 60, proceeding from the corresponding compound No.119. The results are also shown in Table 29.

TABLE 29

Compound:

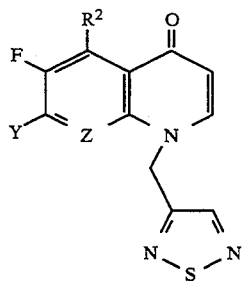

| Compound No. | Group R$^2$ | Y | Z | Property | Melting point (°C.) | $^1$H-NMR | Solvent |
|---|---|---|---|---|---|---|---|
| 120 | H | (S) H$_2$N-⟨pyrrolidine⟩-N— | C\|H | Pale yellow solid | 241 ∫ 245 | [DMSO-d$_6$] δ; 1.7(brs, 1H), 1.95(brs, 1H), 3.1-3.7(m, 5H), 6.11(s, 2H), 6.51(d, J=7.8Hz, 1H), 7.77(d, J=14.2Hz, 1H), 8.97(s, 1H), 9.12(s, 1H) | Et$_3$N/MeCN |
| 121 | H | H$_2$N-⟨pyrrolidine, Me⟩-N— Cis (−) | C\|H | Pale yellow solid | 225 ∫ 228.5 | [DMSO-d$_6$] δ; 0.97(d, J=7.3Hz, 3H), 2.4(brs, 1H), 3.1-3.8(m, 5H), 6.15((s, 2H), 6.57 (d, J=7.8Hz, 1H), 7.81(d, J=14.2Hz, 1H), 9.01(s, 1H), 9.15(s, 1H) | " |
| 122 | H | HN⟨piperazine⟩N— | C\|H | Colorless solid | 261 ∫ 265 | [DMSO-d$_6$] δ; 2.81(s, 4H), 3.09(s, 4H), 6.21(s, 2H), 7.06(d, J=7.3Hz, 1H), 7.88(d, J=13.2Hz, 1H), 9.00(s, 1H), 9.23(s, 1H) | " |

EXAMPLE 66

Ethyl 3-(1,2,5-thiadiazol-3-ylmethylamino)-2-(2,3,4,5-tetrafluorobenzoyl)acrylate (Compound No.123)

A mixture of ethyl 2,3,4,5-tetrafluorobenzoylacetate (528 mg), ethyl orthoformate (0.5 ml) and acetic anhydride (0.57 ml) was stirred at 130° C. for 3 hours. After the solvent was removed in vacuo, a solution of 3-aminomethyl-1,2,5-thiadiazole (0.24 g) in benzene (5 ml) was added to the residue. The mixture was stirred at room temperature for 40 minutes, and the solvent was removed. To the residue was added 10 ml of isopropylether. The precipitate was filtrated. The title compound No. 123 was obtained as a pale yellow solid (600 mg).

Melting point: 154°-156° C. $^1$H-NMR(CDCl$_3$) δ; 0.98 and 1.11(t,J=7 Hz,3H), 3.95-4.15(m,2H), 4.93(d,J=6.4 Hz,2H), 6.9-7.2(m1H), 8.20 and 8.27(d,J=14 Hz,1H), 8.55 and 8.57(s,1H)

EXAMPLE 67

Ethyl 6,7,8-trifluoro-1-(1,2,5-thiadiazol-3-ylmethyl)-1,4-dihydro-4-oxoquinoline-3-carboxylate (Compound No.124)

To a solution of compound No.123 (0.58 g) obtained in Example 66 in tetrahydrofuran (20 ml), 62 mg of sodium hydride (60% in oil) was added. Then the solution was stirred for 0.5 hour at room temperature. The solvent was removed, and the residue was added with an aqueous 5% citric acid solution (10 ml). Extraction was carried out with chloroform (50 ml). The organic phase was dried ($Na_2SO_4$) followed by evaporation. The residue was added with isopropylether (10 ml), and the precipitate was filtrated. The title compound No. 124 was obtained as a colorless solid (390 mg).

Melting point: 200.5°–203° C. $^1$H-NMR(CDCl$_3$) δ; 1.41(t,J=7 Hz,3H), 4.41(q,J=7 Hz,2H), 5.76(s,2H), 8.1–8.25(m,1H), 8.58(s,2H)

EXAMPLE 68

6,7,8-Trifluoro-1-(1,2,5-thiadiazol-3-ylmethyl)-1,4-dihydro-4-oxoquinoline-3-carboxylic acid (Compound No.125)

Compound No.124 (0.38 g) obtained in Example 67 was dissolved in acetic acid (4.5 ml) and 6N-HCl (1.5 ml). The solution was stirred at 100° C. for 1.5 hours. After cooling, ethanol (3 ml) was added thereto, and the precipitate was filtrated, followed by washing with ethanol and ether. The title compound No. 125 was obtained as a colorless solid (0.34 g).

Melting point: 219.5°–222° C. $^1$H-NMR(DMSO-d$_6$) δ; 6.2(s,2H),8.1–8.3(m,1H), 8.96(s,1H), 9.27(s,1H)

EXAMPLE 69

Compounds Nos. 126–128 listed in Table 30 were synthesized in a similar manner to Example 68, proceeding from the corresponding compound No.125. The data are also shown in Table 30.

TABLE 30

Compound:

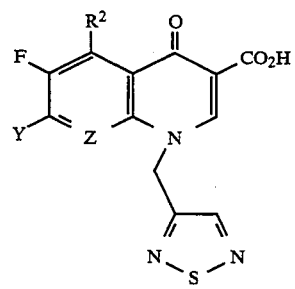

| Compound No. | Group R² | Y | Z | Property | Melting point (°C.) | ¹H-NMR | Solvent |
|---|---|---|---|---|---|---|---|
| 126 | H | H₂N–⟨pyrrolidine⟩–N— (S) | C\|F | Pale yellow solid | 227 ∫ 231 | [DMSO-d₆] δ; 1.4–1.7(m, 1H), 1.8–2.0(m, 1H), 3.1–3.8(m, 5H), 6.09 6.11(s, 2H), 7.74(d, J=14Hz, 1H), 8.91(s, 1H), 9.02(s, 1H) | Et₃N/CH₃CN |
| 127 | H | H₂N–⟨pyrrolidine-Me⟩–N— Cis (−) | C\|F | Colorless solid | 233.5 ∫ 237 | [DMSO-d₆] δ; 0.98(d, J=6Hz, 3H), 2.25(brs, 1H), 3.4–4.9(m, 5H), 6.12(s, 2H), 7.75(d, J=14Hz, 1H), 8.93(s, 1H), 9.06(s, 1H) | " |
| 128 | H | HN⟨piperazine⟩N— | C\|F | Colorless solid | 227 ∫ 228.5 | [DMSO-d₆] δ; 2.75(s, 4H), 3.11(s, 4H), 6.18(s, 2H), 7.86(d, J=13Hz, 1H), 8.95(s, 1H), 9.14(s, 1H) | " |

EXAMPLE 70

Ethyl 3-(1,2,3-thiadiazol-4-ylmethylamino)-2-(2,4,5-trifluorobenzoyl)acrylate (Compound No.129)

A mixture of ethyl 2,4,5-trifluorobenzoylacetate (418 mg), ethyl orthoformate (0.43 ml) and acetic anhydride (0.48 ml) was stirred at 130° C. for 3 hours. After the solvent was removed in vacuo, a solution of 4-aminomethyl-1,2,3-thiadiazole (0.2 g) in benzene (5 ml) was added to the residue. The mixture was stirred for 4 hours. The solvent was removed in vacuo. To the residue was added 10 ml of isopropylether. The precipitate was filtrated. The title compound No. 129 was obtained as a colorless solid (440 mg).

Melting point: 176°–178° C. $^1$H-NMR(CDCl$_3$) δ; 0.95 and 1.09(t,J=7 Hz, 3H), 3.9–4.15(m,2H), 5.14(d,J=6 Hz,2H), 6.8–7.0(m,1H), 7.1–7.3(m,1H), 8.18 and 8.29(d,J=14 Hz,1H), 8.49 and 8.51(s,1H)

EXAMPLE 71

Ethyl 6,7-difluoro-1-(1,2,3-thiadiazol-4-ylmethyl)-1,4-dihydro-4-oxoquinoline-3-carboxylate (Compound No.130)

To a solution of compound No.129 (0.44 g) obtained in Example 70 in tetrahydrofuran (30 ml), 48 mg of sodium hydride (60% in oil) was added. Then the solution was stirred for 3 hours at room temperature. The solvent was distilled off, and the residue was added with an aqueous 5% citric acid solution (10 ml), followed by extraction with chloroform (50 ml). The organic phase was dried over $Na_2SO_4$ and evaporated. After addition of isopropylether (10 ml), the precipitate was filtrated. The title compound No. 130 was obtained as a colorless solid (280 mg). Melting point: 234°–237° C. $^1$H-NMR(DMSO-$d_6$) δ; 1.30(t,J=7 Hz,3H), 4.25(B,J=7 Hz,2H), 6.11(s,2H), 8.0–8.25(m,2H), 9.06(s,1H), 9.36(s,1H)

EXAMPLE 72

6,7-Difluoro-1-(1,2,3-thiadiazol-4-ylmethyl)-1,4-dihydro-4-oxoquinoline-3-carboxylic acid (Compound No.131)

Compound No.130 (0.28 g) obtained in Example 71 was dissolved in acetic acid (4.5 ml) and 6N-HCl (1.5 ml). The solution was stirred at 100° C. for 2 hours. After cooling, water (30 ml) was added thereto, and the precipitate was filtrated and washed with water, ethanol and ether. The title compound No. 131 was obtained as a pale yellow solid (0.2 g).

Melting point: 257°–261° C. $^1$H-NMR(DMSO-$d_6$) δ; 6.30(s,2H), 8.27(dd,J=10 Hz,J=9 Hz,1H), 8.40(dd,J=12 Hz,J=6.3 Hz,1H), 9.41(s,1H), 9.44(s,1H)

EXAMPLE 73

Compounds Nos. 132–134 listed in Table 31 were synthesized in a similar manner to Example 73, proceeding from the corresponding compound No.131. The data are also shown in Table 31.

EXAMPLE 74

Ethyl 2-(2,6-dichloro-5-fluoronicotinoyl)-3-(1,3,4-thiadiazol-2-ylamino)acrylate (Compound No.135)

A mixture of ethyl 2,6-dichloro-5-fluoronicotinoylacetate (4.0 g), ethyl orthoformate (3.19 g) and acetic anhydride (4.39 g) was stirred at 130° C. for 2 hours. After the excessive acetic anhydride and ethyl orthoformate were removed in vacuo, the residue was dissolved in chloroform (50 ml), to which a methanol solution (100 ml) containing 2-amino-1,3,4-thiazole (1.44 g) was added and stirred overnight at room temperature. The solvent was removed in vacuo. After dissolved in a small amount of chloroform, hexane was added thereto for solidifying. The precipitate was filtrated. The title compound No. 135 was obtained as a pale yellow solid (5.12 g).

Melting point: 137°–140.5° C. $^1$H-NMR(CDCl$_3$) δ; 0.98 and 1.19(t,J=7 Hz, 3H), 4.08–4.27(m,2H), 7.45 and 7.58(d,J=6.8 Hz, 1H), 8.68–9.04(m,2H)

EXAMPLE 75

Ethyl 6-fluoro-7-chloro-1-(1,3,4-thiadiazol-2-yl)-1,4-dihydro-4-oxo-1,8-naphthyridine-3-carboxylate (Compound No.136)

A solution of compound No.135 (5.12 g) obtained in Example 74 and potassium carbonate (1.81 g) in dimethylformamide (20 ml) was stirred for 15 minutes at 90° C. After addition of an aqueous 5% citric acid solution (500 ml), the precipitate was filtrated and washed with

TABLE 31

Compound:

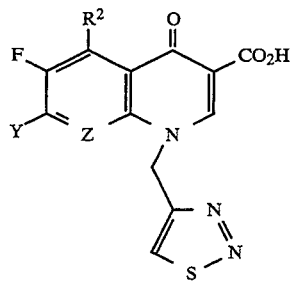

| Compound No. | Group R² | Y | Z | Property | Melting point (°C.) | ¹H-NMR | Solvent |
|---|---|---|---|---|---|---|---|
| 132 | H | H₂N–[pyrrolidine]–N– (S) | C\|H | Yellow solid | 251.5 ∫ 254 | [DMSO-$d_6$] δ; 1.7(brs, 1H), 2.0(brs, 1H), 3.1–3.9(m, 5H), 6.22(s, 2H), 6.73(brs, 1H), 7.75(d, J=14Hz, 1H), 9.23(s, 1H), 9.39(s, 1H) | Et₃N/CH₃CN |
| 133 | H | H₂N–[pyrrolidine, Me]–N– Cis (−) | C\|H | Yellow solid | Decomposed from 280 | [DMSO-$d_6$] δ; 0.99(brs, 3H), 2.2(brs, 1H), 3.1–3.8(m, 5H), 6.22(s, 2H), 6.73(brs, 1H), 7.75(d, J=14Hz, 1H), 9.23(s, 1H), 9.38(s, 1H) | " |
| 134 | H | HN–[piperazine]–N– | C\|H | Yellow solid | 231.5 ∫ 234.5 | [DMSO-$d_6$] δ; 2.84(s, 4H), 3.13(s, 4H), 6.31(s, 2H), 7.33(brs, 1H), 7.88(d, J=13.7Hz, 1H), 9.34(s, 1H), 9.40(s, 1H) | " | water, ethanol and ether successively. The title compound No. 136 was obtained as a pale yellow solid (3.83 g).

Melting point: 201°-203° C. $^1$H-NMR(CDCl$_3$) δ; 1.44(t,J=7 Hz,3H), 4.45(q,J=7 Hz,2H), 8.57(d,J=6.8 Hz,1H), 9.21(s,1H), 10.02(s,1H)

EXAMPLE 76

Ethyl 7-(pyrrolidin-1-yl)-6-fluoro-1-(1,3,4-thiadiazole-2-yl)-1,4-dihydro-4-oxo-1,8-naphthyridine-3-carboxylate (Compound No.137)

A mixture of compound No.136 (100 mg)obtained in Example 75, pyrrolidine (22 mg) and triethylamine (33 mg) in acetonitrile (10 ml) was stirred at 80° C. for 60 minutes. The precipitate was filtrated and washed with ethanol. The title compound was obtained as a pale yellow solid (79 mg).

Melting point: 238°-242° C. $^1$H-NMR(DMSO-d$_6$) δ; 1.32(t,J=7 Hz,3H), 1.99(brs,4H), 3.74(brs,4H), 4.29(q,J=7 Hz,2H), 7.84(d,J=12.7 Hz,1H), 9.48(s,1H), 9.52(s,1H)

EXAMPLE 77

7-(Pyrrolidin-1-yl)-6-fluoro-1-(1,3,4-thiadiazole-2-yl)-1,4-dihydro-4-oxo-1,8-naphthyridine-3-carboxylic acid, sodium salt (Compound No.138)

Compound No.137 (0.05 g) obtained in Example 76 was suspended in tetrahydrofuran (20 ml), to which an aqueous 1N-NaOH solution (0.13 ml) was added. The solution was stirred at room temperature for 3 days. After evaporation of the solvent, chloroform was added. The precipitate was filtrated. The title compound No. 138 was obtained as a pale brown solid (42 mg).

Melting point: 253°-263° C. $^1$H-NMR(DMSO-d$_6$) δ; 1.78(s,4H), 7.68(d,J=12.7 Hz,1H), 9.73(s,1H), 9.87(s,1H)

EXAMPLE 78

Compounds No. 139-140 were synthesized in a similar manner to Example 77.

The name of compound No. 139, its property, melting point and $^1$H-NMR data are as follows: Ethyl 6-fluoro-7-(4-methylpiperazin-1-yl)-1-(1,3,4-thiadiazol-2-yl)-1,4-dihydro-4-oxo-1,8-naphthyridine-3-carboxylate (Compound No.139).

Pale orange solid.

Melting point: 204°-206° C. $^1$H-NMR(DMSO-d$_6$) δ; 1.31(t,J=7 Hz,3H), 2.24(s,3H), 2.50(brs,4H), 3.77(brs,4H), 4.28(q,J=7 Hz,2H), 8.04(d,J=13.2 Hz, 1H), 9.46(s,1H), 9.59(s,1H)

The name of compound No. 140, its property, melting point and $^1$H-NMR data are as follows: 6-Fluoro-7-(4-methylpiperazin-1-yl)-1-(1,3,4-thiadiazol-2-yl)-1,4-dihydro-4-oxo-1,8- naphthyridine- 3-carboxylic acid, sodium salt (Compound No.140)

Pale orange solid.

Melting point: 241°-246° C., decomposed $^1$H-NMR(DMSO-d$_6$) δ; 2.13(s,3H), 2.24(s,4H), 7.77(d,J=13.7 Hz,1H), 9.74(s,1H), 9.90(s,1H)

EXAMPLE 79

Ethyl 6,7-difluoro-1-(1,3,4-thiadiazol-2-yl)-1,4-dihydro-4-oxoquinoline-3-carboxylate (Compound No.141)

A mixture of ethyl 2,4,5-trifluorobenzoylacetate (9.84 g), ethyl orthoformate (10 ml) and acetic anhydride (17 ml) was stirred at 130° C. for 12 hours. After the solvent was removed in vacuo, a solution of 2-amino-1,3,4-thiadiazole (4.55 g) and methanol (30 ml) in chloroform (40 ml) was added to the residue. The mixture was stirred at room temperature for 24 hours. The solvent was removed in vacuo. The residue was purified by chromatography on silicagel (chloroform/ethyl acetate 1:1 as an eluent) to obtain an intermediate of yellow oil (14 g). A solution of this oily material (14 g) and potassium carbonate (5.4 g) in N,N-dimethylformamide (40 ml) was stirred for 20 minutes at 100° C. The solvent was removed in vacuo. After addition of water (200 ml) to the residue, the precipitate was filtrated and washed with water, ethanol and ether successively. The title compound No. 141 was obtained as a yellow solid (9.4 g).

Melting point: 235°-238° C. $^1$H-NMR(DMSO-d$_6$) δ; 1.28(t,J=7 Hz,3H), 4.24(q,J=7 Hz,2H), 7.56(dd,J=11.7 Hz, J=6.3 Hz,1H), 8.14(dd,J=9 Hz,J=10 Hz,1H), 8.78(s,1H), 9.88(s,1H)

EXAMPLE 80

6,7-Difluoro-1-(1,3,4-thiadiazol-2-yl)-1,4-dihydro-4-oxoquinoline-3-carboxylic acid (Compound No.142)

Compound No.141 (0.5 g) obtained in Example 79 was dissolved in tetrahydrofuran (70 ml). To this solution were added 3 ml of water and 0.75 ml of 2N-NaOH, then-stirred at room temperature for 20 minutes. After evaporation of tetrahydrofuran in vacuo, the residue was neutralized with an aqueous 20% acetic acid solution. The precipitate was filtrated and washed with water, ethanol and ether successively. The title compound No. 142 was obtained as a yellow solid (0.38 g).

Melting point: 233°-236° C. $^1$H-NMR(DMSO-d$_6$) δ; 7.13(dd,J=12 Hz,J=6.8 Hz,1H), 8.15(dd,J=9 Hz,J=10 Hz,1H), 9.87(s,1H), 10.0(s,1H)

EXAMPLE 81

Ethyl 2-(2,4,5-trifluorobenzoyl)-3-(5-methyl-1,3,4-thiadiazol-2-ylamino)acrylate (Compound No.143)

A mixture of ethyl 2,4,5-trifluorobenzoylacetate (2.18 g), ethyl orthoformate (1.97 g) and acetic anhydride (4.12 g) was stirred at 130° C. for 3 hours. After the excessive acetic anhydride and ethyl orthoformate were removed in vacuo, the residue was dissolved in 50 ml benzene, to which a solution of 2-amino-5-methyl-1,3,4-thiadiazole (1.00 g) in methanol (150 ml) was added. The mixture was stirred at room temperature for 24 hours. The solvent was removed in vacuo. The residue was purified by chromatography on silicagel (chloroform/ethyl acetate 10:1 as an eluent). The title compound No. 143 was obtained as a colorless solid (1.78 g).

Melting point: 147°-151° C. $^1$H-NMR(CDCl$_3$) δ; 1.04 and 1.19(t,J=7 Hz,3H); 2.73 and 2.75(s,1H); 4.10-4.28(m,2H); 6.87-7.06(m,1H); 7.30-7.42 and 7.48-7.62(m,1H); 8.34 and 8.70(d,J=12.7 Hz,1H); 11.31(d,J=12.2 Hz,1H)

EXAMPLE 82

Ethyl 6,7-difluoro-1-(5-methyl-1,3,4-thiadiazol-2-yl)-1,4-dihydro-4-oxoquinoline-3-carboxylate (Compound No.144)

To a solution of compound No.143 (1.5 g) obtained in Example 81 in tetrahydrofuran (40 ml), 0.20 g of sodium hydride (60% in oil) was added. Then the solution was stirred for 2 days at room temperature. Tetrahydrofuran was evaporated. The residue was dissolved in chloroform (80 ml) and washed with 5% citric acid solution (10 ml). The aqueous solution was extracted with chloroform (80 ml), followed by dehydration with Glauber's salt. Chloroform was evaporated, and the residue was purified by chromatography on silicagel (chloroform/ethyl acetate 5:1 as an eluent). The title compound No. 144 was obtained as a pale yellow solid (0.85 g).

Melting point: 170°–173° C. $^1$H-NMR(CDCl$_3$) δ; 1.40(t,J=7.3 Hz,3H); 2.96(s,3H); 4.39(q,J=7 Hz,2H); 7.35(dd,J=10.7 Hz,6.3 Hz,1H); 8.28(dd,J=8.8 Hz,10 Hz,1H); 8.58(s,1H)

EXAMPLE 83

6,7-Difluoro-1-(5-methyl-1,3,4-thiadiazol-2-yl)-1,4-dihydro-4-oxoquinoline-3-carboxylic acid, sodium salt (Compound No.145)

Compound No.144 (0.1 g) obtained in Example 82 was dissolved in tetrahydrofuran (10 ml) and 1N-NaOH (0.3 ml). The solution was stirred at room temperature overnight. After addition of chloroform, the precipitate was filtrated, followed by washing with chloroform. The title compound No. 145 was obtained as a pale yellow solid (77 mg).

Melting point: Colored from 255° C., decomposed 295° C. $^1$H-NMR(DMSO-d$_6$) δ; 2.80(s,3H); 7.02(dd,J=12.7 Hz,6.8 Hz,1H); 7.92(dd, J=10.7 Hz,9.3 Hz,1H); 9.97(s,1H)

EXAMPLE 84

Ethyl 2-(2,6-dichloro-5-fluoronicotinoyl)-3-(5-methyl-1,3,4-thiadiazol-2-ylamino)acrylate (Compound No.146)

A mixture of ethyl 2,6-dichloro-5-fluoronicotinoylacetate (4.00 g), ethyl orthoformate (3.18 g) and acetic anhydride (4.38 g) was stirred at 130° C. for 2 hours. After the excessive acetic anhydride and ethyl orthoformate were removed in vacuo, the residue was dissolved in 40 ml chloroform, to which a solution of 2-amino-5-methyl-1,3,4-thiadiazole (1.61 g) in methanol (180 ml) was added. The mixture was stirred at room temperature overnight. The solvent was removed in vacuo. The residue was purified by chromatography on silicagel (chloroform/ethyl acetate 10:1 then 5:1 as an eluent). The title compound No. 146 was obtained as a pale yellow solid (4.37 g).

Melting point: 142°–152° C. decomposed $^1$H-NMR(CDCl$_3$) δ; 0.97 and 1.17(t,J=7 Hz,3H); 2.76 and 2.87(s,3H); 4.07–4.25(m,2H); 7.44 and 7.56(d,J=7 Hz,1H); 8.63 and 8.87(s,1H)

EXAMPLE 85

Ethyl 6-fluoro-7-chloro-1-(5-methyl-1,3,4-thiadiazol-2-yl)-1,4-dihydro-4-oxo-1,8-naphthyridine-3-carboxylate (Compound No.147)

To a solution of compound No.146 (4.1 g) obtained in Example 84 in tetrahydrofuran (100 ml), 0.49 g of sodium hydride (60% in oil) was added. Then the solution was stirred for 1 day at room temperature. Tetrahydrofuran was removed and the residue was dissolved in chloroform (200 ml), followed by washing with 5% citric acid solution and dried over Na$_2$SO$_4$. Chloroform was evaporated, and the residue was suspended in hexane, and the solid was filtrated. The title compound No. 147 was obtained as an orange solid (3.53 g).

Melting point: 159°–162° C. $^1$H-NMR(CDCl$_3$) δ; 1.43(t,J=7 Hz,3H); 2.86(s,3H); 4.44(q,J=7 Hz,2H); 8.55(d,J=7.3 Hz,1H); 9.89(s,1H)

EXAMPLE 86

Ethyl 7-(3-(S)-aminopyrrolidin-1-yl)-6-fluoro-1-(5-methyl-1,3,4-thiadiazol-2-yl)-1,4-dihydro-4-oxo-1,8-naphthyridine-3-carboxylate (Compound No.148)

A mixture of compound No.147 (100 mg), 3-(S)aminopyrrolidine (33 mg) and triethylamine (39 mg) in acetonitrile (10 ml) was stirred at 80° C. for 60 minutes. After cooling, the precipitate was filtrated and washed with ethanol. The title compound No. 148 was obtained as a pale orange solid (73 mg).

Melting point: 265°–268° C. $^1$H-NMR(D$_2$O) δ; 1.35(t,J=7 Hz,3H); 2.71(s,3H);4.26(q,J=7 Hz,2H); 7.59(d,J=12.2 Hz,1H); 8.90(s,1H)

EXAMPLE 87

7-(3-(S)-Aminopyrrolidin-1-yl)-6-fluoro-1-(5-methyl-1,3,4-thiadiazol-2-yl)-1,4-dihydro-4-oxo-1,8-naphthyridine-3-carboxylic acid, sodium salt (Compound No.149)

Compound No.148 (0.05 g) obtained in Example 86 was dissolved in water (3 ml) and 1N-NaOH (0.1 ml). The solution was stirred at room temperature for 24 hours. After evaporation of water, chloroform was added. The precipitate was filtrated. The title compound No. 149 was obtained as a pale orange solid (18 mg).

Melting point: Colored from 200° C., decomposed 280° C. $^1$H-NMR(D$_2$O) δ; 2.0–2.3(brs,1H); 2.43(s,3H); 3.6(brs,1H); 7.25 (d,J=12.7 Hz,1H); 8.85(s,1H)

EXAMPLE 88

Ethyl 2-(2,6-dichloro-5-fluoronicotinoyl)-3-(5-trifluoromethyl-1,3,4-thiadiazol-2-ylamino)acrylate (Compound No.150)

A mixture of ethyl 2,6-dichloro-5-fluoronicotinoylacetate (2.8 g), ethyl orthoformate (2.6 ml) and acetic anhydride (2.8 ml) was stirred at 130° C. for 6 hours. After the solvent was removed in vacuo, a solution of 2-amino-5-trifluoromethyl-1,3,4-thiadiazole (1.69 g) in chloroform (20 ml) and ethanol (8 ml) was added to the residue. The mixture was stirred at room temperature for 4 hours. The solvent was removed in vacuo. The residue was purified by chromatography on silicagel (chloroform/ethyl acetate 50:1 as an eluent). The title compound No. 150 was obtained as a yellow waxy solid (4.5 g).

Melting point: 73°–76° C. ¹H-NMR(CDCl₃) δ; 0.98 and 1.19(t,J=7 Hz,3H), 4.05–4.25(m,2H), 7.47 and 7.62(d,J=7.4 Hz,1H), 8.67 and 8.91 (d,J=12 Hz,1H)

EXAMPLE 89

Ethyl 7-chloro-6-fluoro-1-(5-trifluoromethyl-1,3,4-thiadiazole-2-yl)-1,4-dihydro-4-oxo-1,8-naphthyridine-3-carboxylate (Compound No.151)

A solution of compound No.150 (4.3 g) obtained in Example 88 and sodium hydrogencarbonate (0.79 g) in N,N-dimethylformamide (30 ml) was stirred for 15 minutes at 100° C. The solvent was removed in vacuo, and extracted with chloroform (200 ml). The organic phase was washed with water. The organic layer was dried over Na₂SO₄ and evaporated. The residue was added with ether (20 ml) and the precipitate was filtrated. The title compound No. 151 was obtained as a colorless solid (3.2 g).

Melting point: 177.5°–178.5° C. ¹H-NMR(CDCl₃) δ; 1.44(t,J=7 Hz,3H), 4.46(q,J=7 Hz,2H), 8.58(d,J=6.8 Hz,1H), 10.0(s,1H)

EXAMPLE 90

7-Chloro-6-fluoro-1-(5-trifluoromethyl-1,3,4-thiadiazole-2-yl)-1,4-dihydro-4-oxo-1,8-naphthyridine-3-carboxylic acid (Compound No.152)

Compound No.151 (30 mg) obtained in Example 89 was dissolved in a mixture of acetic acid (2 ml) and HCl (0.5 ml). The solution was stirred at 100° C. for 0.5 hour. After cooling and addition of water (4 ml), the precipitate was filtrated and washed with ethanol, ether and n-hexane. The title compound No. 152 was obtained as a colorless solid (13 mg).

Melting point: 232°–237° C. ¹H-NMR(DMSO-d₆) δ; 8.81(d,J=7 Hz,1H), 9.79(s,1H)

EXAMPLE 91

6-Fluoro-7-(pyrrolidin-1-yl)-1-(5-trifluoromethyl-1,3,4-thiadiazol-2-yl)-1,4-dihydro-4-oxo-1,8-naphthyridine-3-carboxylic acid (Compound No.153)

A mixture of compound No.151 (200 mg) obtained in Example 89 and pyrrolidine (67 mg) in chloroform (5 ml) was stirred at room temperature for 15 minutes. After evaporation of the solvent, ethanol (10 ml) was added. The precipitate was filtrated to obtain a colorless solid (170 mg). 50 mg of the obtained solid was taken and dissolved in tetrahydrofuran (3 ml), to which 6N-HCl (0.3 ml) was added. After stirring for 1 day at room temperature, the precipitate was filtrated and washed with water, ethanol and ether. The title compound No. 153 was obtained as a yellow solid (30 mg).

Melting point: 239.5°–241° C. ¹H-NMR(DMSO-d₆) δ; 2.04(brs,4H), 3.84(brs,4H), 8.04(d,J=12.7 Hz,1H), 9.63(s,1H)

EXAMPLE 92

Ethyl 2-(2,4,5-trifluorobenzoyl)-3-(5-trifluoromethyl-1,3,4-thiadiazol-2-ylamino)acrylate (Compound No.154)

A mixture of ethyl 2,4,5-trifluorobenzoylacetate (2.46 g), ethyl orthoformate (2.6 ml) and acetic anhydride (2.8 ml) was stirred at 130° C. for 6 hours. After the solvent was removed in vacuo, a solution of 2-amino-5-trifluoromethyl-1,3,4-thiadiazole (1.69 g) and ethanol (5 ml) in chloroform (20 ml) was added to the residue. The mixture was stirred at room temperature for 24 hours. The solvent was removed in vacuo. The residue was purified by chromatography on silicagel (chloroform/ethyl acetate 50:1 as an eluent). The title compound No. 154 was obtained as a yellow oil (2.3 g).

¹H-NMR(CDCl₃) δ; 1.05 and 1.21(t,J=7 Hz,3H), 4.1–4.3(m,2H), 6.85–7.05(m,1H), 7.35–7.45 and 7.52–7.7(m,1H), 8.36–8.73(d,J=12 Hz,1H)

EXAMPLE 93

Ethyl 6,7-difluoro-1-(5-trifluoromethyl-1,3,4-thiadiazole-2-yl)-1,4-dihydro-4-oxoquinoline-3-carboxylate (Compound No.155)

A solution of compound No.154 (2.3 g) obtained in Example 92 and potassium carbonate (0.75 g) in N,N-dimethylformamide (20 ml) was stirred for 10 minutes at 100° C. The solvent was removed in vacuo. After extraction with chloroform, the organic phase was washed with water, dried (Na₂SO₄) and evaporated. After addition of hexane (50 ml) to the residue, the precipitate was filtrated. The title compound was obtained as a red solid (1.1 g)

Melting point: 130°–136° C. ¹H-NMR(CDCl₃) δ; 1.37(t,J=7 Hz,3H), 4.33(q,J=7 Hz,2H), 7.46(dd, J=10.7 Hz,J=6.4 Hz,1H), 8.13(dd,J=9.8 Hz,J=8.5 Hz,1H), 8.55(s,1H)

EXAMPLE 94

6,7-Difluoro-1-(5-trifluoromethyl-1,3,4-thiadiazole-2-yl)-1,4-dihydro-4-oxoquinoline-3-carboxylic acid (Compound No.156)

Compound No.155 (30 mg) obtained in Example 93 was dissolved in a mixture of acetic acid (2 ml) and HCl (0.5 ml). The solution was stirred at 100° C. for 40 minutes. After allowed to be cooled, water (4 ml) was added to the reaction mixture, and the precipitate was filtrated and washed with ethanol, ether and n-hexane. The title compound No. 156 was obtained as a pale orange solid (18 mg).

Melting point: 272°–276° C. ¹H-NMR(DMSO-d₆) δ; 7.96(dd,J=12 Hz,J=6 Hz,1H), 8.33(dd,J=9 Hz,J=10 Hz,1H), 9.25 (s,1H)

EXAMPLE 95

Ethyl 3-(1,2,5-thiadiazole-3-ylamino)-2-(2-methyl-3,4,6-trifluorobenzoyl)acrylate (Compound No.157)

Compound No. 157 (colorless needles) was prepared in a similar manner to Example 17, proceeding from the corresponding compounds ethyl 2-methyl-3,4,6,-trifluorobenzoylacetate, ethyl orthoformate, acetic anhydride and 3-amino-1,2,5-thiadiazole hydrochloride.

Melting point: 134°–136° C. ¹H-NMR(CDCl₃) δ; 1.14(t,J=7 Hz,3H), 2.22(d,J=3 Hz,3H), 4.13(q,J=7 Hz,2H), 6.80(dt,J=10 Hz,6 Hz,1H), 8.36(s,1H), 9.00(d,J=12 Hz,1H)

EXAMPLE 96

Ethyl 5-methyl-6,7-difluoro-1-(1,2,5-thiadiazol-3-yl)-1,4-dihydro-4-oxoquinoline-3-carboxylate (Compound No.158)

Compounds No. 158 which is a pale yellow solid was prepared in a similar manner to Example 18, proceeding from the corresponding compound No.157.

Melting point: 208°–213° C. $^1$H-NMR(CDCl$_3$) δ; 1.38(t,J=7 Hz,3H), 2.89(d,J=3 Hz,3H), 4.39(q,J=7 Hz,2H), 6.86(dd,J=11 Hz,7 Hz,1H), 8.46(s,1H), 8.79(s,1H)

EXAMPLE 97

5-Methyl-6,7-difluoro-1-(1,2,5-thiadiazol-3-yl)-1,4-dihydro-4-oxoquinoline-3-carboxylic acid (Compound No.159)

Compounds No. 159 which is a colorless solid was prepared in a similar manner to Example 19, proceeding from the corresponding compound No.158.

Melting point: 264°–268° C. decomposed $^1$H-NMR(DMSO-d$_6$) δ; 2.87(d,J=3 Hz,3H), 7.58(dd,J=7 Hz,J=12 Hz,1H), 9.07(s,1H),9.22(s,1H)

EXAMPLE 98

Compounds Nos. 160–163 listed in Tables 32 and 33 were synthesized in a similar manner to Example 4, proceeding from the compound No.159 obtained in Example 97.

EXAMPLE 99

Ethyl 7-chloro-6-fluoro-1-(1,2,4-thiadiazol-5-yl)-1,4-dihydro-4-oxo-1,8-naphthyridine-3-carboxylate (Compound No.164)

A mixture of ethyl 2,6-dichloro-5-fluoronicotinoylacetate (4.2 g), ethyl orthoformate (3.9 ml) and acetic anhydride (4.3 ml) was stirred at 135° C. for 2 hours. After the solvent was removed in vacuo, the residue was added with chloroform (20 ml) and ethanol (10 ml). 5-Amino-1,2,4-thiadiazole (1.51 g) was added thereto and allowed to react for 8 hours. The solvent was removed. The residue was added with n-hexane, and the precipitate was filtrated. 4.1 g of a yellow solid was obtained. 3.5 g was taken therefrom and dissolved in dimethylformamide (35 ml). 0.36 g of sodium hydride (60% in oil) was added thereto and allowed to react at 100° C. for 5 minutes. The solvent was removed. After addition of water to the residue, the insoluble matter was filtrated and washed with water, ethanol, ether and n-hexane successively. The title compound No. 164 was obtained as a pale yellow solid (2.5 g).

TABLE 32

Compound:

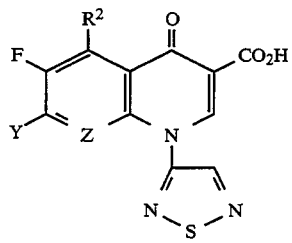

| Compound No. | R$^2$ | Y | Z | Property | Melting Point (°C.) | $^1$H-NMR | Solvent |
|---|---|---|---|---|---|---|---|
| 160 | CH$_3$ | HN⟨piperazinyl⟩N— | C\|H | Colorless solid | 194 / 198 | [DSMO-d$_6$] δ; 2.64(brs, 4H), 2.80(d, J=3Hz, 3H), 3.03(brs, 4H), 6.52(d, J=7Hz, 1H), 8.89(s, 1H), 9.30(s, 1H) | CH$_3$CN Et$_3$N |
| 161 | CH$_3$ | CH$_3$N⟨piperazinyl⟩N— | C\|H | Colorless solid | 243 / 247 | [DMSO-d$_6$] δ; 2.20(s, 3H), 2.42(brs, 4H), 2.80(d, J=3Hz, 3H), 3.12(brs, 4H), 6.57(d, J=8Hz, 1H), 8.93(s, 1H), 9.31(s, 1H) | CH$_3$CN Et$_3$N |

TABLE 33

| Compound No. | R$^2$ | Y | Z | Property | Melting Point (°C.) | $^1$H-NMR | Solvent |
|---|---|---|---|---|---|---|---|
| 162 | CH$_3$ | H$_2$N–⟨pyrrolidinyl⟩–N— (S) | C\|H | Pale yellow solid | 205 / 208 | [DMSO-d$_6$] δ; 1.58–1.72(m, 1H), 1.88–2.03(m, 1H), 2.77(brs, 3H), 3.05~3.15(m, 1H), 3.28–3.60(m), 5.99(d, J=8Hz, 1H), 8.82(s, 1H), 9.29(s, 1H) | CH$_3$CN Et$_3$N |
| 163 | CH$_3$ | H$_2$N–⟨pyrrolidinyl with CH$_3$⟩–N— Cis (−) | C\|H | Pale yellow solid | 242 / 245 | [DMSO-d$_6$] δ; 0.94(d, J=7Hz, 3H), 2.09–2.23(m, 1H), 2.75(brs, 1H), 3.10–3.62(m), 5.59(d, J=8Hz, 1H), 8.82(s, 1H), 9.28(s, 1H) | CH$_3$CN Et$_3$N |

Melting point: 203°–206° C. ¹H-NMR(CDCl₃) δ; 1.34(t,J=7 Hz,3H), 4.34(q,J=7 Hz,2H), 8.71(d,J=8 Hz,1H), 8.85(s,1H), 9.71(s,1H)

EXAMPLE 100

7-Chloro-6-fluoro-1-(1,2,4-thiadiazol-5-yl)-1,4-dihydro-4-oxo-1,8-naphthyridine-3-carboxylic acid (Compound No.165)

Compound No. 164 (1.1 g) obtained in Example 99 was dissolved in a mixture of tetrahydrofuran (40 ml) and c-HCl (10 ml). The solution was stirred at 80° C. for 1.5 hour. After the solvent was removed in vacuo, the precipitate was filtrated and washed with ethanol, ether and n-hexane. The title compound No. 165 was obtained as a slightly yellow solid.

Melting point: 278°–282° C. ¹H-NMR(DMSO-d₆) δ; 8.82(d,J=7 Hz,1H), 8.88(s,1H), 9.81(s,1H)

EXAMPLE 101

Compounds Nos. 166–167 listed in Table 34 were synthesized in a similar manner to Example 41, proceeding from the compound No.164 obtained in Example 99.

TABLE 34

Compound:

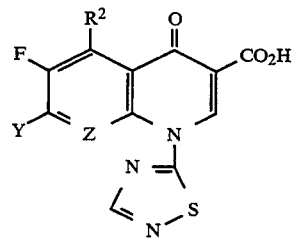

| Compound No. | Group R² | Y | Z | Property | Melting Point (°C.) | ¹H-NMR | Solvent |
|---|---|---|---|---|---|---|---|
| 166 | H | H₂N–[cyclohexyl]–N— S form.HCl | N | Dim yellow solid | Colored from 285, decomposed | [DMSO-d₆] δ; 2.28–2.50(m, 2H), 4.05–4.18(m, 3H), 8.18(d, J=13Hz, 1H), 8.49(brs, 3H), 9.53(s, 1H), 9.73(s, 1H) | CHCl₃ Et₃N ↓ 6NHCl |
| 167 | H | H₂N–[Me-cyclohexyl]–N— .HCl (−) | N | Pale yellow solid | Colored from 225, decomposed | [DMSO-d₆] δ; 1.18(d, J=6Hz, 3H), 1.49–1.57(m, 1H), 1.69–1.77(m, 1H), 3.80–4.48(s, 4H), 8.19(d, J=13Hz, 1H), 8.87(s, 1H), 9.75(s, 1H) | CHCl₃ Et₃N ↓ 6NHCl |

EXAMPLE 102

Compounds Nos. 168–170 listed in Table 35 were synthesized in a similar manner to Example 11, proceeding from the compound No.165 obtained in Example 100.

TABLE 35

Compound:

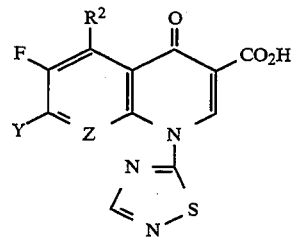

| Compound No. | Group R² | Y | Z | Property | Melting Point (°C.) | ¹H-NMR | Solvent |
|---|---|---|---|---|---|---|---|
| 168 | H | MeN–[piperazinyl]–N— .HCl | N | Dim yellow solid | Colored from 290, decomposed | [DMSO-d₆] δ; 2.49(s, 3H), 2.84(brs, 4H), 8.38(d, J=13Hz, 1H), 8.89(s, 1H), 9.83(s, 1H) | MeCN Et₃N ↓ 6N—HCl |

TABLE 35-continued

Compound:

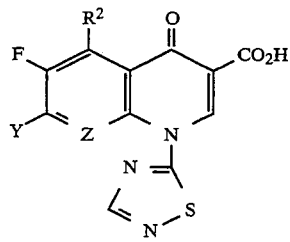

| Compound No. | Group R² | Y | Z | Property | Melting Point (°C.) | ¹H-NMR | Solvent |
|---|---|---|---|---|---|---|---|
| 169 | H | HN⟨  ⟩N— .HCl | N | Pale brown solid | Colored from 280, decomposed | [DMSO-d₆] δ; 3.43(brs, 4H), 4.38(brs, 4H), 8.37(d, J=13Hz, 1H), 8.90(s, 1H), 9.20(brs, 2H), 9.83(s, 1H) | MeCN Et₃N ↓ 6N—HCl |
| 170 | H | H₂N—⟨ ⟩N— .HCl | N | Dim yellow solid | Colored from 278, decomposed | [DMSO-d₆] δ; 4.30(brs, 1H), 4.63–4.85(m, 4H), 8.23(d, J=13Hz, 1H), 8.68(brs, 3H), 8.88(s, 1H), 9.74(s, 1H) | MeCN Et₃N ↓ 6N—HCl |

EXAMPLE 103

Ethyl 6,7-difluoro-1-(1,2,4-thiadiazol-5-yl)-1,4-dihydro-4-oxoquinoline-3-carboxylate (Compound No.171)

A mixture of ethyl 2,4,5-trifluorobenzoylacetate (3.7 g), ethyl orthoformate (3.9 ml) and acetic anhydride (4.3 ml) was stirred at 135° C. for 3 hours. After the solvent was removed in vacuo, a solution of 5-amino-1,2,4-thiadiazole (1.51 g) in chloroform (20 ml) and ethanol (10 ml) was added to the residue. The mixture was stirred at room temperature for 8 hours. The solvent was removed. The residue was purified by column chromatography on silicagel (chloroform/ethyl acetate 4:1 as an eluent) to obtain 4.4 g of a yellow oil. A solution of this oil (4 g) and sodium hydride(0.45 g) in dimethylformamide (40 ml) was stirred for 5 minutes at 100° C. The solution was removed. Chloroform and water were added to the residue, and the organic phase was extracted. After evaporation of the solvent, the residue was added with ethanol, and the precipitate was filtrated, washed with ethanol, ether and n-hexane successively. The title compound No. 171 was obtained as a yellow solid (1.5 g).

Melting point: 149°–152° C. ¹H-NMR(CDCl₃) δ; 1.42(t,J=7 Hz,3H), 4.43(q,J=7 Hz,2H), 8.23–8.33(m,2H), 8.71(s,1H), 8.79(s,1H)

EXAMPLE 104

6,7-Difluoro-1-(1,2,4-thiadiazol-5-yl)-1,4-dihydro-4-oxoquinoline-3-carboxylic acid (Compound No.172)

Compound No.171 (0.7 g) was dissolved in a mixture of tetrahydrofuran (28 ml) and c-HCl (7 ml). The solution was stirred at 80° C. for 1 hour. After evaporation of the solvent, the residue was added with ethanol. The precipitate was filtrated and washed with ethanol, ether and n-hexane. The title compound No. 172 was obtained as a brown solid (0.56 g).

Melting point: 212°–216° C. ¹H-NMR(DMSO-d₆) δ; 7.99(dd,J=6 Hz,J=12 Hz,1H), 8.34(dd,J=9 Hz,J=10 Hz,1H), 9.08(s,2H)

EXAMPLE 105

Compound No. 173 listed in Table 36 was prepared in a similar manner to Example 4, proceeding from the compound No.172.

TABLE 36

Compound:

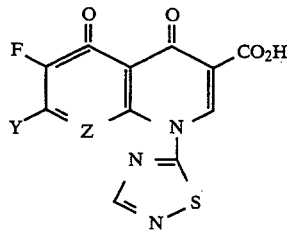

| Compound No. | R² | Group Y | Z | Property | Melting Point (°C.) | ¹H-NMR | Solvent |
|---|---|---|---|---|---|---|---|
| 173 | H | ![piperidinyl]N— | CH | Pale brown solid | 145 ∫ 147 | [DMSO-d₆] δ; 1.93(brs, 4H), 3.48(brs, 4H), 6.71(d, J=7Hz, 1H), 7.85(d, J=15Hz, 1H), 8.92(s, 1H), 9.06(s, 1H) | MeCN Et₃N |

EXAMPLE 106

Ethyl 2-(2,6-dichloro-5-fluoronicotinoyl)-3-(1H-tetrazol-5-ylamino)acrylate (Compound No.174)

A mixture of ethyl 2,6-dichloro-5-fluoronicotinoylacetate (5.6 g), ethyl orthoformate (5.2 ml) and acetic anhydride (5.6 ml) was stirred at 130° C. for 4 hours. After the solvent was removed in vacuo, a solution of 5-amino-1H-tetrazole (1.7 g) in benzene (20 ml) and methanol (40 ml) was added to the residue. The mixture was stirred at room temperature for 5 hours. The solvent was removed. After addition of hexane (100 ml.) to the residue, stirring was carried out for 1 hour. The precipitate was filtrated. The title compound No. 174 was obtained as a colorless solid (6.5 g).

Melting point: 150.5°–152° C. ¹H-NMR(DMSO-d₆) δ; 1.05(t,J=7 Hz,3H), 3.9–4.15(m,2H), 7.93(s,1H), 8.24 and 8.60(d,J=8 Hz,1H), 8.79(s,1H)

EXAMPLE 107

Ethyl 7-chloro-6-fluoro-1-(1H-tetrazol-5-yl)-1,4-dihydro-4-oxo-1,8-naphthyridine-3-carboxylate (Compound No.175)

A solution of compound No.174 (3 g) obtained in Example 106 and potassium carbonate (1.1 g) in N,N-dimethylformamide (20 ml) was stirred for 1 hour at 110° C. The solution was removed in vacuo. After addition of 6N-HCl (30 ml) to the residue, the precipitate was filtrated and washed with water, ethanol and ether successively. The title compound No. 175 was obtained as a yellow solid (2.7 g).

Melting point: 202°–207° C. ¹H-NMR(DMSO-d₆) δ; 1.28(t,J=7 Hz,3H), 4.26(q,J=7 Hz,2H), 8.57(d,J=7.7 Hz,1H), 8.92(s,1H)

EXAMPLE 108

7-Chloro-6-fluoro-1-(1H-tetrazol-5-yl)-1,4-dihydro-4-oxo-1,8-naphthyridine-3-carboxylic acid (Compound No.176)

Compound No.175 (1.2 g) obtained in Example 107 was dissolved in a mixture of acetic acid (5 ml) and 6N-HCl (5 ml). The solution was stirred at 100° C. for 2 hours. After evaporation of the solvent in vacuo, 5 ml of ethanol was added to the residue. The precipitate was filtrated and washed with ether. The title compound No. 176 was obtained as a pale yellow solid (0.68 g).

Melting point: 270° C. or more, colored and decomposed ¹H-NMR(DMSO-d₆) δ; 8.74(d,J=7.2 Hz,1H), 9.07(s,1H)

EXAMPLE 109

Compounds No. 177 listed in Table 37 was synthesized in a similar manner to Example 4, proceeding from the compound No.176 obtained in Example 108.

TABLE 37

Compound:

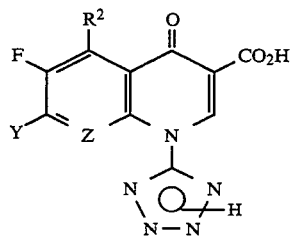

| Compound No. | Group R² | Y | Z | Property | Melting Point (°C.) | ¹H-NMR | Solvent |
|---|---|---|---|---|---|---|---|
| 177 | H | H₂N(S)—[pyrrolidinyl]—N— | N | Pale yellow solid | Colored from 250, decomposed | [DMSO-$d_6$] δ; 1.5–1.8(m, 1H), 1.8–2.05(m, 1H), 2.7–3.2(m, 4H), 8.0(d, J=12.8Hz, 1H), 8.44(s, 1H) | MeCN + DMF Et₃N |

EXAMPLE 110

Compounds Nos. 178–179 listed in Table 38 were synthesized in a similar manner to Example 11, proceeding from the compound No.177 obtained in Example 109.

solid. A solution of this solid (7.0 g) and potassium carbonate (5.5 g) in N,N-dimethylformamide (40 ml) was stirred for 1 hour at 100° C. The solution was removed in vacuo. 6N-HCl (30 ml) was added to the residue and stirred for 10 minutes. The precipitate was filtrated and washed with water, ethanol and ether suc-

TABLE 38

Compound:

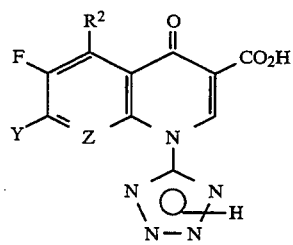

| Compound No. | Group R² | Y | Z | Property | Melting Point (°C.) | ¹H-NMR | Solvent |
|---|---|---|---|---|---|---|---|
| 178 | H | HN⟨piperazine⟩N— .HCl | N | Colorless solid | 300 or more | [DMSO-$d_6$] δ; 3.14(brs, 4H), 3.82(brs, 4H), 8.24(d, J=12.8Hz, 1H), 8.94(s, 1H), 9.57(brs, 2H), | MeCN + DMF Et₃N ↓ 6N—HCl |
| 179 | H | MeN⟨piperazine⟩N— .HCl | N | Colorless solid | Colored from 285, decomposed | [DMSO-$d_6$] δ; 2.74(s, 3H), 3.10(brs, 2H), 3.3–3.6(br, 4H), 4.15–4.4(br, 2H), 8.27(d, J=12.8Hz, 1H), 8.97(s, 1H) | MeCN + DMF Et₃N ↓ 6N—HCl |

EXAMPLE 111

Ethyl 6,7-difluoro-1-(1H-tetrazol-5-yl)-1,4-dihydro-4-oxoquinoline-3-carboxylate (Compound No.180)

A mixture of ethyl 2,4,5-trifluorobenzoylacetate (9.8 g), ethyl orthoformate (10 ml) and acetic anhydride (17 ml) was stirred at 130° C. for 4 hours. After the solvent was removed in vacuo, a solution of 5-amino-1H-tetrazole (3.4 g) in benzene (20 ml) and methanol (80 ml) was added to the residue. The mixture was stirred at 60° C. for 20 minutes. The solvent was removed in vacuo. After addition of hexane (100 ml) to the residue, the precipitate was filtrated to obtain 7 g of a colorless cessively. The title compound No. 180 was obtained as a yellow solid (4 g).

Melting point: 233–236.5° C. ¹H-NMR(DMSO-$d_6$) δ; 1.29(t,J=7 Hz,3H), 4.26(q,J=7 Hz,2H), 7.99(dd,J=12 Hz,6.3 Hz,1H), 8.15(dd,J=10.7 Hz,8.5 Hz,1H), 8.90(s,1H)

EXAMPLE 112

6,7-Difluoro-1-(1H-tetrazol-5-yl)-1,4-dihydro-4-oxoquinoline-3-carboxylic acid (Compound No.181)

Compound No.180 (2 g) obtained in Example 111 was dissolved in a solution of acetic acid (10 ml) and 6N-

HCl (10 ml). The solution was stirred at 100° C. for 1 hour, and the solvent was removed. After addition of water (100 ml) to the residue, the precipitate was filtrated and washed with ethanol and ether. The title compound No. 181 was obtained as a pale yellow solid (1.1 g).

Melting point: 246°–249° C. $^1$H-NMR(DMSO-d$_6$) δ; 8.14 (dd,J=12 Hz,6.4 Hz,1H), 8.31(dd,J=10 Hz,9 Hz,1H), 9.13(s,1H)

EXAMPLE 113

Compounds Nos. 182–183 listed in Table 39 were synthesized in a similar manner to Example 11, proceeding from the compound No.181 in Example 112.

EXAMPLE 115

Ethyl 7-chloro-6-fluoro-1-(4-methyl-1,2,5-thiadiazol-3-yl)-1,4-dihydro-4-oxo-1,8-naphthyridine-3-carboxylate (Compound No.185)

To a solution of compound No.184 (20 g) obtained in Example 114 in tetrahydrofuran (500 ml), 2.04 g of sodium hydride(60% in oil) was added at room temperature. Then the solution was stirred for 0.5 hour at 70° C. After addition of 5% citric acid solution to make the system acidic, tetrahydrofuran was removed. Extraction was carried out with chloroform (500 ml). The organic phase was dried (MgSO$_4$) and evaporated. The

TABLE 39

Compound:

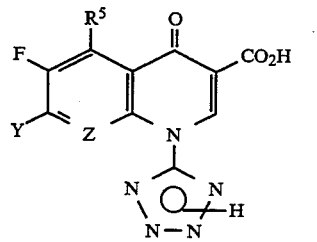

| Compound No. | Group R² | Y | Z | Property | Melting Point (°C.) | $^1$H-NMR | Solvent |
|---|---|---|---|---|---|---|---|
| 182 | H | HN⟨ ⟩N— ·HCl | C\|H | Colorless solid | Colored from 280, decomposed | [DMSO-d$_6$] δ; 3.27(s, 4H), 3.40(s, 4H), 7.64(d, J=6.4Hz, 1H), 8.0(d, J=13.3Hz, 1H), 9.02(s, 1H), 9.24(brs, 2H) | DMF Et$_3$N ↓ 6N—HCl |
| 183 | H | H$_2$N⟨(S)⟩N— ·HCl | C\|H | Yellow solid | Colored from 270, decomposed | [DMSO-d$_6$] δ; 1.95–2.2(m, 1H), 2.2–2.4(m, 1H), 3.45–4.05(m, 5H), 7.19(d, J=6.8Hz, 1H), 7.89(d, J=14.1Hz, 1H), 8.15(brs, 3H), 8.90(s, 1H) | DMF Et$_3$N ↓ 6N—HCl |

EXAMPLE 114

Ethyl 2-(2,6-dichloro-5-fluoronicotinoyl)-3-(4-methyl-1,2,5-thiadiazol-3-ylamino)acrylate (Compound No.184)

A mixture of ethyl 2,6-dichloro-5-fluoronicotinoylacetate (14.9 g), ethyl orthoformate (13.3 ml) and acetic anhydride (15 ml) was stirred at 130° C. for 3 hours. After the solvent was removed in vacuo, a solution of 3-amino-4-methyl-1,2,5-thiadiazole hydrochloride (7.7 g) and triethylamine (5.2 g) in chloroform (80 ml) was added to the residue. The mixture was stirred at room temperature for 1 hour. The solvent was removed in vacuo. The residue was purified by column chromatography on silicagel (chloroform as an eluent). The title compound No. 184 was obtained as a yellow oil (20 g).

$^1$H-NMR(CDCl$_3$) δ; 0.98 and 1.18(t,J=7 Hz,3H), 2.60 and 2.64(s,3H), 4.08–4.21(m,2H), 7.43 and 7.56(d,J=7 Hz,1H), 8.98 and 9.06(d,J=12.6 Hz,1H)

residue was purified by column chromatography on silicagel (chloroform/ethyl acetate 10:1 as an eluent). The title compound No. 185 was obtained as a colorless solid (15.1 g).

Melting point: 191.5°–192.5° C. $^1$H-NMR(CDCl$_3$) δ; 1.41(t,J=7 Hz,3H), 2.42(s,3H), 4.41(q,J=7 Hz,2H), 8.50(d,J=7 Hz,1H), 8.65(s,1H)

EXAMPLE 116

7-Chloro-6-fluoro-1-(4-methyl-1,2,5-thiadiazol-3-yl)-1,4-dihydro-4-oxo-1,8-naphthyridine-3-carboxylic acid (Compound No.186)

Compound No.185 (15.1 g) obtained in Example 115 was dissolved in acetic acid (180 ml) and c-HCl (80 ml). The solution was stirred for 1 hour with heating under reflux. After cooling, water (200 ml) was added thereto. The precipitate was filtrated and washed with water, ethanol and ether. The title compound No. 186 was obtained as pale yellow needles (13.3 g).

Melting point: 247°–249° C. $^1$H-NMR(DMSO-d$_6$) δ; 2.35(s,3H), 8.78(d,J=7.7 Hz,1H), 9.17(s,1H)

EXAMPLE 117

7-(3-(S)-Aminopyrrolidin-1-yl)-6-fluoro-1-(4-methyl-1,2,5-thiadiazol-3-yl)-1,4-dihydro-4-oxo-1,8-naphthyridine-3-carboxylic acid hydrochloride (Compound No.187)

A mixture of compound No.186 (12 g), triethylamine (7.1g) and 3-(S)-aminopyrrolidine (4.47 g) in acetonitrile (240 ml) was stirred at 80° C. for 180 minutes. After cooling, the precipitate was filtrated and washed with ethanol, followed by adding to a mixture of 200 ml of 6N-HCl and 150 ml of acetic acid and heating until dissolved. After the solvent was removed in vacuo, ethanol was added. The precipitate was collected by filtration and washed with ethanol and ether. The title compound was obtained as a pale yellow solid (15.6 g).

A water/.ethanol (1:1) solution was used for reprecipitation to obtain the title compound No. 187 in a colorless solid (9.8 g).

Melting point: 278° C. decomposed $^1$H-NMR(DMSO-d$_6$) δ; 1.95–2.30(br,2H), 2.37(s,3H), 3.7–4.2(br,2H), 8.12(d,J=12.4 Hz,1H), 8.4(brs,3H), 8.96(s,1H)

This compound can also be obtained as slightly yellow needles by crystallizing from water. It decomposes at a temperature of 299° C. or higher.

EXAMPLE 118

Compounds Nos. 188–193 listed in Tables 40 and 41 were synthesized in a similar manner to Example 117.

TABLE 40

Compound:

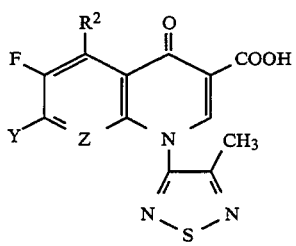

| Compound No. | R$^2$ | Y | Z | Property | Melting Point (°C.) | $^1$H-NMR | Solvent |
|---|---|---|---|---|---|---|---|
| 188 | H | HN⌐N— .HCl | N | Pale yellow solid | Decomposed from 286 | [DMSO-d$_6$] δ; 2.34(s, 3H), 3.12(s, 4H) 3.74(s, 4H), 8.23(d, J=12.8Hz, 1H), 9.04(s, 1H), 9.65(brs, 2H) | Et$_3$N/CH$_3$CN ↓ AcOH, 6N—HCl |
| 189 | H | Me, H$_2$N–<N— (3S, 4S).HCl | N | Colorless solid | Decomposed from 293 | [DMSO-d$_6$] δ; 1.03(d, J=6Hz, 3H), 2.37(s, 3H), 2.45–2.7(brs, 1H), 3.2–4.2(m, 5H), 8.13(d, J=12.4Hz, 1H), 8.25(brs, 3H), 8.95(s, 1H) | Et$_3$N/CH$_3$CN ↓ AcOH, 6N—HCl |
| 190 | H | HO—<N— | N | Colorless solid | 191.5 | [DMSO-d$_6$] δ; 2.34(s, 3H), 3.5–4.6(m, 6H), 7.98(d, J=11.6Hz, 1H), 8.70(s, 1H) | Et$_3$N CH$_3$CN (no acid treatment) |

TABLE 41

| Compound No. | R$^2$ | Y | Z | Property | Melting Point (°C.) | $^1$H-NMR | Solvent |
|---|---|---|---|---|---|---|---|
| 191 | H | H$_2$N—<N— .HCl | N | Colorless solid | 237–239.5 | [DMSO-d$_6$] δ; :2.35(s, 3H), 3.8–4.95(m, 4H), 8.15(d, J=11.6Hz, 1H), 8.59(brs, 3H), 8.96(s, 1H) | Et$_3$N/CH$_3$CN ↓ AcOH, 6N—HCl |
| 192 | H | H$_2$N—<N— | N | Pale yellow solid | 214–218 | [DMSO-d$_6$] δ; 2.35(s, 3H), 2.7–3.15(m, 3H), 3.6–4.5(m, 4H), 7.99(d, J=11.1Hz, 1H), 8.82(s, 1H) | Et$_3$N CH$_3$CN (no acid treatment |

TABLE 41-continued

| Compound No. | R² | Y | Z | Property | Melting Point (°C.) | ¹H-NMR | Solvent |
|---|---|---|---|---|---|---|---|
| 193 | H | H₂N–(cyclohexyl-F)–N (trans) | N | Pale yellow solid | Decomposed from 278 | [DMSO-d₆] δ; 2.36(s, 3H), 4.9–5.2(m, 1H), 8.13(d, J=11.1Hz, 1H), 8.97(s, 1H) | Et₃N CH₃CN (no acid treatment) |

EXAMPLE 119

Benzyl 6,7-difluoro-1-(1,2,4-triazol-3-yl)-1,4-dihydro-4-oxoquinoline-3-carboxylate (Compound No.194)

A mixture of benzyl 2,4,5-trifluorobenzoylacetate (1.5 g), ethyl orthoformate (1.08 g) and acetic anhydride (2.24g) was stirred at 130° C. for 3 hours. After the excessive acetic anhydride and ethyl orthoformate were removed in vacuo, a solution of 3-amino-1,2,4-triazole (0.41 g) in methanol (25 ml ) was added to the residue. The mixture was stirred at room temperature for 3 days. The solvent was removed. The residue was purified with a silicagel column (chloroform/ethyl acetate 10:1–5:1 as an eluent). The title compound was obtained as pale yellow needles (1.10 g).

Melting point: 116°–124° C. ¹H-NMR(DMSO-d₆) δ; 5.23(d,J=4.9 Hz,2H), 7.22–7.41(m,5H), 7.58–7.70(m,1H), 7.74–7.88(m,1H), 8.80(s,1H), 9.42(s,1H)

EXAMPLE 120

6,7-Difluoro-1-(1,2,4-triazol-3-yl)-1,4-dihydro-4-oxoquinoline-3-carboxylic acid (Compound No.195) and 6,7-difluoro-1-(N-benzyl-1,2,4-triazol-3-yl)-1,4-dihydro-4-oxoquinoline-3-carboxylic acid (Compound No.196)

To a solution of compound No.194 (1.02 g) in tetrahydrofuran (50 ml) was added a solution of Pd/C (300 mg) ethanol (50 ml), then stirred under H2 gas atmosphere for 1 day. After removing the catalyst with a membrane filter, the filtrate was evaporated. The residue was purified with a silicagel column (chloroform/ethyl acetate 1:1 as an eluent). A colorless solid No. 195 was first obtained (53 mg), and next, a colorless solid of N-benzyl, No. 196 was obtained (95 mg).

The melting point and the ¹H-NMR data of the compound 195 are as follows:

Melting point: 170°–177° C. ¹H-NMR(DMSO-d₆) δ; 7.79–7.98(m,2H), 8.79(s,1H), 9.38(s,1H)

The melting point and the ¹H-NMR data of the compound 196 are as follows:

Melting point: 244–258° C. ¹H-NMR (DMSO-d₆) δ; 4.9 and 5.17(d,J=12.7 Hz,2H), 6.52(s,1H), 7.16–7.23(m,2H), 7.27–7.33(m,3H), 7.42–7.54(m,2H), 7.68 and 7.71(s,1H)

EXAMPLE 121

7-(3-(S)-Aminopyrrolidin-1-yl)-6-fluoro-1-(1,2,4-triazol-3-yl)-1,4-dihydro-4-oxoquinoline-3-carboxylic acid (Compound No.197)

A mixture of compound No.194 (50 mg) was dissolved in acetonitrile (5 ml), to which triethylamine (21 mg) and 3-(S)-aminopyrrolidine (21 mg) were added and stirred at 80° C. for 30 minutes. The precipitate was filtrated and washed with ethanol. The title compound No. 197 was obtained as a yellow solid (46 mg).

Melting point: 250°–260° C., colored from approx. 245° C. ¹H-NMR(DMSO-d₆) δ; 1.65–1.82(m,1H), 1.98–2.12(m,1H), 3.51–3.77(m,4H), 6.60(d,J=7.8 Hz,1H ), 8.88(d,J=16.1 Hz,1H), 8.94(s,1H), 9.22(s,1H)

EXAMPLE 122

Ethyl 2-(2,6-dichloro-5-fluoronicotinoyl)-3-(1-methyl-1,2,4-triazol-5-ylamino)acrylate (Compound No.198)

A mixture of ethyl 2,6-dichloro-5-fluoronicotinoylacetate (3.00 g), ethyl orthoformate (2.38 g) and acetic anhydride (3.85 g) was stirred at 130° C. for 2 hours. After the excessive acetic anhydride and ethyl orthoformate were removed in vacuo, the residue was dissolved in chloroform (50 ml). A solution of 5-amino-1-methyl-1,2,4-triazole (1.05 g) in chloroform (30 ml) was added thereto. The mixture was stirred at room temperature overnight. The solvent was removed. The residue was purified with a silicagel column (chloroform/ethyl acetate 5:1 as an eluent). The title compound No. 198 was obtained as a yellow solid (2.34 g).

Melting point: 102°–103° C. ¹H-NMR(CDCl₃) δ; 1.20 and 1.26(t,J=7 Hz,3H), 3.86 and 3.91(s,3H), 4.06–4.23(m,2H), 7.42 and 7.56(d,J=7 Hz,1H), 7.72 and 7.76(s,1H), 8.85 and 8.97(d,J=12.2 Hz,1H)

EXAMPLE 123

Ethyl 7-chloro-6-fluoro-1-(1-methyl-1,2,4-triazol-5-yl)-1,4-dihydro-4-oxo-1,8-naphthyridine-3-carboxylate (Compound No.199)

A solution of compound No.198 (1.00 g) and potassium carbonate (0.39 g) in dimethylformamide (20 ml) was stirred for 30 minutes at 90° C. The solvent was removed and a 5% citric acid solution (50 ml) and chloroform (50 ml) were added thereto. The organic phase was dehydrated with Glauber's salt, followed by evaporation of solvent. The residue was suspended in a small amount of ethyl acetate for filtration. The title compound No. 199 was obtained as a colorless solid (0.79 g).

Melting point: 256°–263° C. ¹H-NMR(CDCl₃) δ; 1.39(t,J=7 Hz,3H), 3.80(s,3H), 4.40(q,J=7 Hz,2H), 8.04(s,1H), 8.48(d,J=7.3 Hz,1H), 8.62(s,1H)

EXAMPLE 124

7-Chloro-6-fluoro-1-(1-methyl-1,2,4-triazol-5-yl)-1,4-dihydro-4-oxo-1,8-naphthyridine-3-carboxylic acid (Compound No.200)

Compound No.199 (0.1 g) was dissolved in acetic acid (10 ml) and 6N-HCl (3 ml). The solution was stirred at 110° C. for 1 hour. After evaporation of the solvent, the residue was suspended in diethylether for filtration. The title compound No. 200 was obtained as a colorless solid (80 mg).

Melting point: 238–242° C. ¹H-NMR(DMSO-d₆) δ; 3.71(s,3H), 8.22(s,1H), 8.75(d,J=7.8 Hz,1H), 9.06(s,1H)

EXAMPLE 125

7-(3-(S)-Aminopyrrolidin-1-yl)-6-fluoro-1-(1-methyl-1,2,4-triazol-5-yl)-1,4-dihydro-4-oxo-1,8-naphthyridine-3-carboxylic acid hydrochloride (Compound No.201)

A mixture of compound No.200 (50 mg), triethylamine (40 mg) and 3-(S)-aminopyrrolidine (24 mg) in acetonitrile (5 ml) was stirred at 80° C. for 60 minutes. The precipitate was filtrated and washed with ethanol, and was dissolved in 6N-HCl to obtain a hydrochloride. The solvent was removed and suspended in diethylether for filtration. The title compound No. 201 was obtained as a pale brown solid (47 mg).

Melting point: Colored from approx. 240° C., 265–275° C. decomposed ¹H-NMR(DMSO-d₆) δ; 2.13(brs,1H), 2.20(brs,1H), 3.72(s,3H), 8.14(d,J=12.2 Hz,1H), 8.20(s,1H), 8.35(brs,3H), 8.88(s,1H)

EXAMPLE 126

Compounds Nos. 202 and 203 listed in Table 42 were synthesized in a similar manner to Example 125.

umn (chloroform as an eluent). The title compound No. 204 was obtained as a yellow oil (0.43 g).

¹H-NMR(CDCl₃) δ; 1.05 and 1.21(t,J=7 Hz,3H), 3.83 and 3.88(s,3H), 4.10–4.22(m,2H), 6.87–6.97(m,1H), 7.29–7.37 and 7.47–7.37(m,1H), 7.68 and 7.72(s,1H), 8.57 and 8.84(d,J=12 Hz,1H)

EXAMPLE 128

Ethyl 6,7-difluoro-1-(1-methyl-1,2,4-triazol-5-yl)-1,4-dihydro-4-oxoquinoline-3-carboxylate (Compound No.205)

A solution of compound No.204 (347 mg) and potassium carbonate (148 mg) in dimethylformamide (8 ml) was stirred for 30 minutes at 90° C. The solution was removed. An aqueous 5% citric acid (25 ml) and chloroform (25 ml) were used for separation. The organic phase was dried over Na₂SO₄, followed by evaporation. A small amount of ethyl acetate was added to the residue and the precipitate was filtrated. The title compound No. 205 was obtained as a colorless solid (0.235 g).

Melting point: 230–231° C. ¹H-NMR(CDCl₃) δ; 1.40(t,J=7 Hz,3H), 3.81(s,3H), 4.40(q,J=7 Hz,2H), 6.67(dd,J=6 Hz,J=10 Hz,1H), 8.13(s,1H), 8.29(dd,J=8.3 Hz,J=9.8 Hz,1H), 8.39(s,1H)

TABLE 42

Compound:

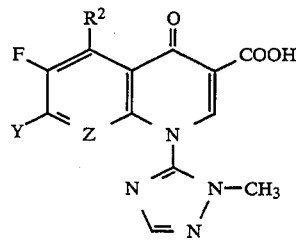

| Compound No. | R² | Y | Z | Property | Melting point (°C.) | ¹H-NMR | Solvent |
|---|---|---|---|---|---|---|---|
| 202 | H | H₂N–[piperidine with Me]–N— (3S, 4S).HCl | N | Pale yellow solid | 270 or more | [DMSO-d₆] δ; 1.06(d, J=6.4Hz, 3H), 2.40–2.70(brs, 1H), 3.72(s, 3H), 8.13(d, J=12.7Hz, 1H), 8.19(s, 1H), 8.86(s, 1H) | Et₃N/CH₃CN ↓ AcOH, HClaq |
| 203 | H | HN–[piperazine]–N— .HCl | N | Pale yellow solid | 270 or more | [DMSO-d₆] δ; 3.17(brs, 4H), 3.70(s, 4H), 3.72(s, 3H), 8.21(s, 1H), 8.27(d, J=13.2Hz, 1H), 8.97(s, 1H) | " |

EXAMPLE 127

Ethyl 2-(2,4,5-trifluorobenzoyl)-3-(1-methyl-1,2,4-triazol-5-ylamino)acrylate (Compound No.204)

A mixture of ethyl 2,4,5-trifluorobenzoylacetate (1.50 g), ethyl orthoformate (2.24 g) and acetic anhydride (1.09 g) was stirred at 130° C. for 3 hours. After the excessive acetic anhydride and ethyl orthoformate were removed in vacuo, a solution of 5-amino-1-methyl-1,2,4-triazole (0.48 g) in benzene (30 ml) and methanol (15 ml) was added to the residue. The mixture was stirred at room temperature overnight. The solvent was removed. The residue was purified with a silicagel col-

EXAMPLE 129

6,7-Difluoro-1-(1-methyl-1,2,4-triazol-5-yl)-1,4-dihydro-4-oxoquinoline-3-carboxylic acid (Compound No.206)

Compound No.205 (0.2 g) was dissolved in acetic acid (10 ml) and 6N-HCl (3 ml). The solution was stirred at 110° C. for 1 hour. After evaporation of the solvent, the residue was suspended in diethylether for filtration. The title compound No. 206 was obtained as colorless solid (166 mg).

Melting point: 254°–264° C. ¹H-NMR(DMSO-d₆) δ; 3.76(S,3H) , 7.37(dd,J=6.3 Hz,J=11.2 Hz,1H), 8.28(S,1H), 8.34(dd,J=8.3 Hz,J=10.3 Hz,1H), 9.16(s,1H)

EXAMPLE 130

7-(3-(S)-Aminopyrrolidin-1-yl)-6-fluoro-1-(1-methyl-1,2,4-triazol-5-yl)-1,4-dihydro-4-oxoquinoline-3-carboxylic acid hydrochloride (Compound No.207)

A mixture of compound No.206 (50 mg), triethylamine (39 mg) and 3-(S)-aminopyrrolidine (22 mg) in acetonitrile (5 ml) was stirred at 80° C. for 60 minutes. The precipitate was filtrated and washed with ethanol, then dissolved in 6N-HCl to obtain a hydrochloride. The solvent was removed and suspended in diethylether for filtration. The title compound No. 207 was obtained as a pale yellow solid (59 mg).

Melting point: Colored from approx. 257° C., 262–266° C. decomposed $^1$H-NMR(DMSO-$d_6$) δ; 2.01–2.16(brs,1H), 2.16–2.28(brs,1H), 3.40–3.52(brs,1H), 3.52–3.67(brs,2H), 3.75(s,3H), 3.82–3.93(brs,1H), 5.70(d,J=7.3 Hz,1H), 7.93 (d,J=14.2 Hz,1H), 8.32(s,1H), 9.00(s,1H)

EXAMPLE 131

Ethyl 2-(2,4,5-trifluorobenzoyl)-3-(1,2,3-triazol-4-ylamino)acrylate (Compound No.208)

A mixture of ethyl 2,4,5-trifluorobenzoylacetate (2.00 g), ethyl orthoformate (1.81 g) and acetic anhydride (3.73 g) was stirred at 130° C. for 3 hours. The excessive acetic acid and ethyl orthoformate were removed in vacuo, and the residue was dissolved in benzene (30 ml), to which a solution of 4-amino-1,2,3-triazole (0.68 g) in methanol (20 ml) was added. The mixture was stirred at room temperature overnight. The solvent was removed. The residue was purified with a silicagel column (chloroform/ethyl acetate 10:1 as an eluent). The title compound No. 208 was obtained as a yellow solid (1.93 g).

Melting point: 157°–159° C. $^1$H-NMR(CDCl$_3$) δ; 1.02 and 1.14(t,J=7 Hz,3H), 4.04–4.20(m,2H), 6.84–6.97(m,1H), 7.26–7.36 and 7.42–7.56 (m,1H), 7.57 and 7.61(s,1H), 8.52 and 8.70(d,J=13.2 Hz,1H)

EXAMPLE 132

Ethyl 6,7-difluoro-1-(1,2,3-triazol-4-yl)-1,4-dihydro-4-oxoquinoline-3-carboxylate (Compound No.209)

A solution of compound No.208 (300 mg) and potassium carbonate (124 mg) in dimethylformamide (6 ml) was stirred for 30 minutes at 90° C. The solvent was removed. The residue was suspended in water for filtration. The title compound No. 209 was obtained as a pale yellow solid (221 mg).

Melting point: 298° C. $^1$H-NMR(DMSO-$d_6$) δ; 1.27(t,J=7 Hz,3H), 4.23(B,J=7 Hz,2H), 7.36((dd,J=6.8 Hz, J=11.7 Hz,1H), 8.15(dd,J=8.8 Hz,J=10.7 Hz,1H), 8.51(s,1H), 8.59(s,1H)

EXAMPLE 133

6,7-Difluoro-1-(1,2,3-triazol-4-yl)-1,4-dihydro-4-oxoquinoline-3-carboxylic acid (Compound No.210)

Compound No.209 (0.1 g) was dissolved in tetrahydrofuran (10 ml) and 6N-HCl (3 ml). The solution was refluxed with heating for 1 hour. After evaporation of the solvent, the residue was suspended in diethylether for filtration. The title compound No. 210 was obtained as a pale yellow solid (82 mg).

Melting point: 215–224° C. $^1$H-NMR(DMSO-$d_6$) δ; 7.58(dd,J=6.8 Hz,J=11.7 Hz,1H), 8.34(dd,J=8.3 Hz, J=10.3 Hz,1H), 8.45–8.59(brs,1H), 8.88(s,1H)

EXAMPLE 134

7-(3-(S)-Aminopyrrolidin-1-yl)-6-fluoro-1-(1,2,3-triazol-4-yl)-1,4-dihydro-4-oxoquinoline-3-carboxylic acid (Compound No.211)

A mixture of compound No.210 (50 mg), triethylamine (38 mg) and 3-(S)-aminopyrrolidine (27 mg) in acetonitrile (5 ml) was stirred at 80° C. for 30 minutes. The precipitate was filtrated and washed with ethanol. The title compound No. 211 was obtained as a pale brown solid (47 mg).

Melting point: 300° C. $^1$H-NMR(DMSO-$d_6$) δ; 1.57–1.69(brs,1H), 1.69–1.83(brs,1H), 6.54(d,J=7.8 Hz,1H), 7.73(s,1H), 7.83(d,J=14.2 Hz,1H), 8.51(s,1H)

EXAMPLE 135

Ethyl 2-(2,6-dichloro-5-fluoronicotinoyl)-3-(1-methyl-1,2,3-triazol-5-ylamino)acrylate (Compound No.212)

A mixture of ethyl 2,6-dichloro-5-fluoronicotinoylacetate (2.80 g), ethyl orthoformate (2.22 g) and acetic anhydride (3.57 g) was stirred at 130° C. for 1.5 hours. After the excessive acetic acid and ethyl orthoformate were removed, the residue was dissolved in chloroform (50 ml). A solution of 5-amino-1-methyl-1,2,3-triazole (98 ml) in methanol (60 ml) was added thereto. The mixture was stirred at room temperature for 0.5 hour. The solvent was removed and then purified through a silicagel column (chloroform/methanol 40:1 as an eluent). The solidified substance was suspended in n-hexane for filtration. The title compound No. 212 was obtained as a colorless solid (2.94 g).

Melting point: 187–189° C. $^1$H-NMR(CDCl$_3$) δ; 0.96 and 1.12(t,J=7 Hz,3H), 4.05–4.25(m,2H), 4.10(s,3H), 7.43(d,J=6.8 Hz), 7.74(s,1H), 8.32 and 8.36(s,1H)

EXAMPLE 136

Ethyl 6-fluoro-7-chloro-1-(1-methyl-1,2,3-triazol-5-yl)-1,4-dihydro-4-oxo-1,8-naphthyridine-3-carboxylate (Compound No.213)

A solution of compound No.212 (300 mg) and potassium carbonate (107 mg) in dimethylformamide (6 ml) was stirred for 30 minutes at 90° C. The solvent was removed. An aqueous 5% citric acid (25 ml) and chloroform (100 ml) were used for separation. The organic phase was dried over Na$_2$SO$_4$ and the solvent was removed. The residue was suspended in diethylether for filtration. The title compound No. 213 was obtained as a colorless solid (249 mg).

Melting point: 251° C. decomposed $^1$H-NMR(CDCl$_3$) δ; 1.40(t,J=7 Hz,3H), 3.95(s,3H), 4.41(q,J=7 Hz,2H), 7.89(s,1H), 8.46(s,1H), 8.49(d,J=6.8 Hz,1H)

EXAMPLE 137

6-Fluoro-7-chloro-1-(1-methyl-1,2,3-triazol-5-yl)-1,4-dihydro-4-oxo-1,8-naphthyridine-3-carboxylic acid (Compound No.214)

Compound No.213 (1.51 g) was dissolved in acetic acid (70 ml) and 6N-HCl (20 ml). The solution was stirred at 110° C. for 1 hour. After evaporation of the solvent, the residue was suspended in diethylether for filtration to obtain the title compound No. 214 as a pale yellow solid (1.33 g).

Melting point: 240°-245° C. $^1$H-NMR (DMSO-d$_6$) δ; 3.87(s,3H), 8.12(s,1H), 8.78(d,J=8.3 Hz,1H), 9.00(s,1H)

EXAMPLE 138

7-(3-(S)-Aminopyrrolidin-1-yl)-6-fluoro-1-(1-methyl-1,2,3-triazol-5-yl)-1,4-dihydro-4-oxo-1,8-naphthyridine-3-carboxylic acid hydrochloride (Compound No.215)

A mixture of compound No.214 (50 mg), triethylamine (36 mg) and 3-(S)-aminopyrrolidine (19 mg) in acetonitrile (5 ml) was stirred at 80° C. for 60 minutes. After the precipitate was collected by filtration, it was washed with ethanol, then dissolved in 6N-HCl to obtain a hydrochloride. After the solvent was removed, the residue was suspended in diethylether for filtration. The title compound No. 215 was obtained as a pale orange solid (37 mg).

Melting point: 269° C. decomposed $^1$H-NMR(DMSO-d$_6$) δ; 1.92-2.13(brs,1H), 2.13-2.30(brs,1H), 3.88(s,3H), 8.09(s,1H), 8.14(d,J=12.2 Hz,1H), 8.28(brs,3H), 8.78(s,1H)

EXAMPLE 139

Compound Nos. 216–217 listed in Table 43 were synthesized in a similar manner to Example 138.

anol was added. The mixture was stirred at room temperature for 3 days. The solvent was removed. The residue was purified through a silicagel column (chloroform/ethyl acetate 10:1 as an eluent). The title compound No. 218 was obtained as a red-brown oil (516 mg).

$^1$H-NMR(CDCl$_3$) δ; 0.99 and 1.22(t,7 Hz,3H), 4.01-4.24(m,2H), 4.05 and 4.10(s,3H), 7.34 and 7.44(d,J=7.0 Hz,1H), 8.81 and 8.99(d,J=12 Hz,1H)

EXAMPLE 141

Ethyl 6-fluoro-7-chloro-1-(1-methyltetrazol-5-yl)-1,4-dihydro-4-oxo-1,8-naphthyridine-3-carboxylate (Compound No.219)

To a solution of compound No.218 (0.08 g) in tetrahydrofuran (8 ml), 11 mg of sodium hydride was added. Then the solution was stirred for 2 days at room temperature. After addition of 5% citric acid solution for neutralization, the solvent was removed. A citric acid solution and chloroform were used for separation. The organic phase was dried over Na$_2$SO$_4$ and the solvent was removed. The residue was purified through a silicagel column (chloroform:ethyl acetate=1:1). The title compound No. 219 was obtained as a pale yellow solid (21 mg).

Melting point: 210°-215° C. $^1$H-NMR(CDCl$_3$) δ; 1.40(t,J=7 Hz,3H), 4.06(s,3H), 4.41(q,J=7 Hz,2H), 8.

TABLE 43

Compound:

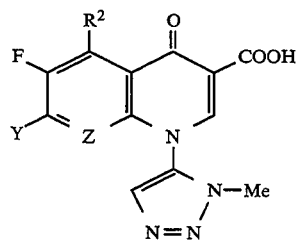

| Compound No. | R$^2$ | Y | Z | Property | Melting point (°C.) | $^1$H-NMR | Solvent |
|---|---|---|---|---|---|---|---|
| 216 | H | H$_2$N–[piperidine ring with Me]– (3S, 4S).HCl | N | Pale yellow solid | Decomposed from 255 | [DMSO-d$_6$] δ; 1.05(d, J=6Hz, 3H), 2.42-2.67(brs, 1H), 3.88(s, 3H), 8.09(s, 1H), 8.14(d, J=12.7Hz, 1H), 8.21(brs, 3H), 8.78(s, 1H) | Et$_3$N/CH$_3$CN |
| 217 | H | HN–[piperazine]–N– .HCl | N | Pale yellow solid | Decomposed from 275 | [DMSO-d$_6$] δ; 3.31(brs, 4H), 3.90(brs, 4H), 3.93(s, 3H), 8.07-8.14(brs, 1H), 8.17(d, J=13.2Hz, 1H), 8.88(s, 1H) | " |

EXAMPLE 140

Ethyl 2-(2,6-dichloro-5-fluoronicotinoyl)-3-(1-methyltetrazol-5-ylamino)acrylate (Compound No.218)

A mixture of ethyl 2,6-dichloro-5-fluoronicotinoylacetate (1.04 g), ethyl orthoformate (1.12 g) and acetic anhydride (1.80 g) was stirred at 130° C. for 2 hours. The excessive acetic anhydride and ethyl orthoformate were removed, and dissolved in chloroform (30 ml), to which a solution of 5-amino-1-methyltetrazole in meth- 51(d,J=6.8 Hz,1H), 8.65(s,1H)

EXAMPLE 142

6-Fluoro-7-chloro-1-(1-methyltetrazol-5-yl)-1,4-dihydro-4-oxo-1,8-naphthyridine-3-carboxylic acid (Compound No.220)

Compound No.219 (123 mg) was dissolved in acetic acid (5 ml) and 6N-HCl (5 ml). The solution was stirred at 110° C. for 2 hours. After evaporation of the solvent, the residue was submitted to a constant boiling with toluene. The residue was suspended in diethylether for filtration. The title compound No. 220 was obtained as a pale brown solid (101 mg).

Melting point: 213°-220° C. ¹H-NMR(DMSO-d₆) δ; 3.97(s,1H), 8.77(d,J=7.8 Hz,1H), 9.09(s,1H)

EXAMPLE 143

7-(3-(S)-Aminopyrrolidin-1-yl)-6-fluoro-1-(1-methyltetrazol-5-yl)-1,4-dihydro-4-oxo-1,8-naphthyridine-3-carboxylic acid hydrochloride (Compound No. 221)

A mixture of compound No.220 (45 mg), triethylamine (37 mg) and 3-(S)-aminopyrrolidine (13 mg) in acetonitrile (5 ml) was stirred at room temperature for 5 minutes. The precipitate was filtrated, washed with ethanol, and dissolved in 6N-HCl to obtain a hydrochloride. After the solvent was removed, the residue was suspended in diethylether for filtration. The title compound No. 221 was obtained as a pale yellow solid (38 mg).

Melting point: 258° C. decomposed ¹H-NMR(DMSO-d₆) δ; 1.96-2.15(brs,1H), 215-2.31(brs,1H), 3.87(brs, 2H), 3.94(s,1H), 3.99(s,3H), 8.15(d,J=12.7 Hz,1H), 8.30(brs,3H), 8.95(s,1H)

EXAMPLE 144

Compound No. 222 listed in Table 44 was synthesized in a similar manner to Example 143.

¹H-NMR(CDCl₃) δ; 1.01 and 1.16(t,J=7 Hz,3H), 2.22 and 2.28(d,J=2.2 Hz,3H), 2.46 and 2.51(s,3H), 4.05-4.2(m,2H), 6.7-6.9(m,1H), 8.62 and 8.79(d,J=12.6 Hz,1H)

EXAMPLE 146

Ethyl 5-methyl-6,7-difluoro-1-(4-methyl-1,2,5-oxadiazol-3-yl)-1,4-dihydro-4-oxoquinoline-3-carboxylate (Compound No.224)

To a solution of compound No.223 (3.4 g) in tetrahydrofuran (50 ml), 0.37 g of sodium hydride (60% in oil) was added. Then the solution was stirred for 7 hours at 70° C. After the solvent was removed and a 5% citric acid solution (10 ml) was added thereto, extraction was carried out with chloroform (100 ml), followed by drying over MgSO₄ and evaporation. To the residue was added isopropylether, and the precipitate was filtrated. The title compound No. 224 was obtained as a yellow solid (1.68 g).

Melting point: 173.5°-174.0° C. ¹H-NMR(DMSO-d₃) δ; 1.39(t,J=7 Hz,3H), 2.35(s,3H), 2.91(d,J=2.6 Hz,3H), 4.39(q,J=7 Hz,2H), 6.49(dd,J=6 Hz,J=11 Hz,1H), 8.25(s,1H)

EXAMPLE 147

5-Methyl-6,7-difluoro-1-(4-methyl-1,2,5-oxadiazol-3-

TABLE 44

Compound:

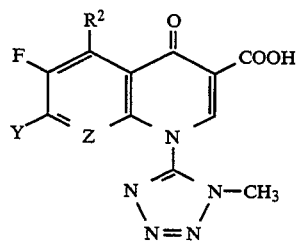

| Compound No. | R² | Y | Z | Property | Melting point (°C.) | ¹H-NMR | Solvent |
|---|---|---|---|---|---|---|---|
| 222 | H | H₂N—[piperidine with Me]—N— (3S, 4S).HCl | N | Pale brown solid | Decomposed from 248 | [DMSO-d₆] δ; 2.42-2.65(br, 1H), 3.76(brs, 2H), 3.94(s, 1H), 3.99(s, 3H), 8.15(d, J=12.7Hz, 1H), 8.29(brs, 3H), 8.94(s, 1H) | Et₃N/CH₃CN ↓ AcOH, HClaq | yl)-1,4-dihydro-4-oxoquinoline-3-carboxylic acid (Compound No.225)

Compound No.224 (1.68 g) was dissolved in acetic acid (20 ml) and 6N-HCl (6 ml). The solution was stirred at 110° C. for 50 minutes. After cooling, ice (50 ml) was added thereto, and the precipitate was filtrated, followed by washing with water, ethanol and isopropyl ether. The title compound No. 225 was obtained as a yellow solid (1.43 g).

Melting point: 199.5°-202° C. ¹H-NMR(DMSO-d₆) δ; 2.29(s,3H), 2.85(d,J=2.5 Hz,3H), 7.51(dd,J=6.8 Hz, J=11.1 Hz,1H), 9.08(s,1H)

EXAMPLE 145

Ethyl 2-(2-methyl-3,4,6-trifluorobenzoyl)-3-(4-methyl-1,2,5-oxadiazol-3-ylamino)acrylate (Compound No.223)

A mixture of ethyl 2-methyl-3,4,6-trifluorobenzoylacetate (2.6 g), ethyl orthoformate (2.5 ml) and acetic anhydride (2.8 ml) was stirred at 130° C. for 2 hours. After the solvent was removed in vacuo, a solution of 3-amino-4-methyl-1,2,5-oxadiazole (0.99 g) in chloroform(20 ml) was added to the residue. The mixture was stirred at room temperature for 24 hours. The solvent was removed. The residue was purified by chromatography on silicagel (chloroform as an eluent). The title compound No. 223 was obtained as a yellow oil (3.4 g).

EXAMPLE 148

Compounds Nos. 226–229 listed in Table 45 were synthesized in a similar manner to Example 117, proceeding from the compound No.225.

TABLE 45

Compound:

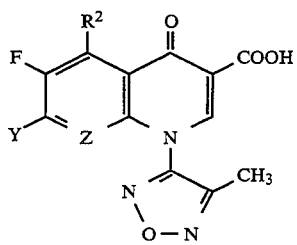

| Compound No. | R² | Y | Z | Property | Melting point (°C.) | ¹H-NMR | Solvent |
|---|---|---|---|---|---|---|---|
| 226 | Me | (S) H₂N-[piperidinyl]-N— .HCl | C\|H | Pale yellow solid | Decomposed from 266 | [DMSO-d₆] δ; 2.0–2.4(m, 2H), 2.33(s, 3H), 2.77(s, 3H), 3.4–3.9(m, 5H), 5.73(d, J=7.7Hz, 1H), 8.36(brs, 3H), 8.89(s, 1H) | Et₃N/CH₃CN ↓ AcOH, HClaq |
| 227 | Me | H₂N-[piperidinyl with Me]-N— (3S, 4S).HCl | C\|H | Pale yellow solid | 241–245 | [DMSO-d₆] δ; 1.08(d, J=6.5Hz, 3H), 2.33(s, 3H), 2.4–2.6(m, 1H), 2.76(s, 3H), 3.5–4.9(m, 5H), 5.70(d, J=6Hz, 1H), 8.37(brs, 3H) 8.89(s, 1H) | " |
| 228 | Me | HN-[piperazinyl]-N— .HCl | C\|H | Colorless solid | Decomposed from 273 | [DMSO-d₆] δ; 2.31(s, 3H), 2.79(s, 3H), 3.22(s, 4H), 3.4(s, 4H), 6.38(d, J=7.7Hz, 1H), 8.98(s, 1H), 9.42(brs, 2H) | " |
| 229 | Me | H₂N-[azetidinyl]-N— | C\|H | Colorless solid | 241–242.5 | [DMSO-d₆] δ; 2.29(s, 3H), 2.69(d, J=3Hz, 3H), 3.6–3.85(m, 3H), 4.24(brs, 2H), 5.53(d, J=8.1Hz, 1H), 8.82(s, 1H) | Et₃N CH₃CN |

EXAMPLE 149

Ethyl 2-(2,3,4,5-tetrafluorobenzoyl)-3-(4-methyl-1,2,5-oxadiazol-3-ylamino)acrylate (Compound No.230)

A mixture of ethyl 2,3,4,5-tetrafluorobenzoylacetate (1.06 g), ethyl orthoformate (1.2 ml) and acetic anhydride (1.3 ml) was stirred at 130° C. for 5 hours. After the solvent was removed in vacuo, a solution of 3-amino-4-methyl-1,2,5-oxadiazole (0.4 g) and triethylamine (0.4 g) in chloroform (10 ml) was added to the residue. The mixture was stirred at room temperature for 1 hour. The solvent was removed. The residue was purified by chromatography on silicagel (chloroform/ethyl acetate 10:1 as an eluent). The title compound No. 230 was obtained as a pale yellow solid (1.17 g).

Melting point: 88°–92° C. ¹H-NMR(CDCl₃) δ; 1.07 and 1.24(t,J=7 Hz,3H), 2.46 and 2.49(s,3H), 4.1–4.3(m,2H), 7.1–7.4(m,1H), 8.47 and 8.73 (d,J=12.6 Hz,1H)

EXAMPLE 150

Ethyl 6,7,8-trifluoro-1-(4-methyl-1,2,5-oxadiazol-3-yl)-1,4-dihydro-4-oxoquinoline-3-carboxylate (Compound No.231)

To a solution of compound No.230 (1.2 g) in tetrahydrofuran (50 ml), 0.128 g of sodium hydride (60% in oil) was added. Then the solution was stirred for 1 hour at 50° C. After addition of 5% citric acid solution (10 ml), tetrahydrofuran was removed in vacuo. The precipitate was filtrated and washed with water, ethanol and ether. The title compound No. 231 was obtained as a colorless solid (0.92 g).

Melting point: 201°–202° C. ¹H-NMR(CDCl₃) δ; 1.4(t,J=7 Hz,3H), 2.4(s,3H), 4.4(q,J=7 Hz,2H), 8.15–8.25(m,1H), 8.29(s,1H)

EXAMPLE 151

6,7,8-Trifluoro-1-(4-methyl-1,2,5-oxadiazol-3-yl)-1,4-dihydro-4-oxoquinoline-3-carboxylic acids(Compound No.232)

Compound No.231 (0.8 g) was dissolved in acetic acid (10 ml) and c-HCl (4 ml). The solution was stirred at 110° C. for 2 hours. After cooling, 50 ml of water was added, and the precipitate was filtrated and washed with water, ethanol and ether. The title compound No. 232 was obtained as a colorless solid (0.6 g).

Melting point: 204.5°–205° C. $^1$H-NMR(DMSO-d$_6$) δ; 2.4(s,3H), 8.2–8.3(m,1H), 9.08(s,1H)

EXAMPLE 152

6,8-Difluoro-7-(3-(S)-aminopyrrolidin-1-yl)-1-(4-methyl-1,2,5-oxadiazol-3-yl)-1,4-dihydro-4-oxoquinoline-3-carboxylic acid (Compound No.233)

A mixture of compound No.232 (100 mg),triethylamine 63 mg) and 3-(S)-aminopyrrolidine(40 mg) in acetonitrile (3 ml) was stirred at 80° C. for 3 minutes. After cooling, the precipitate was filtrated. The title compound No. 233 was obtained as a yellow solid (60 mg).

Melting point: 169°–170° C. $^1$H-NMR(DMSO-d$_6$+CF$_3$COO-d) δ; 1.99 and 2.17(brs,2H), 2.37(s,3H), 3.87(brs,3H), 7.86(d,J=13.7 Hz,1H), 8.11(brs,3H), 8.92(s,1H)

EXAMPLE 153

Compounds Nos. 234–239 listed in Tables 46 and 47 were synthesized in a similar manner to Example 4, proceeding from the compound No.3.

EXAMPLE 154

Compounds Nos. 240–243 listed in Table 48 were prepared in a similar manner to Example 11, proceeding from the compound No.159.

EXAMPLE 155

Compounds Nos. 244 and 245 listed in Table 49 were prepared in a similar manner to Example 41, proceeding from the compound No.79.

TABLE 46

Compound:

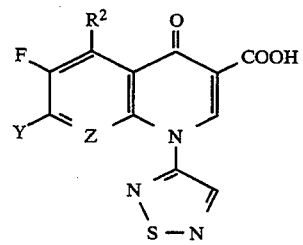

| Compound No. | R$^2$ | Y | Z | Property | Melting point (°C.) | $^1$H-NMR | Solvent |
|---|---|---|---|---|---|---|---|
| 234 | H | H$_2$N–(cyclohexyl, F)–N— trans | N | Dim yellow solid | Decomposed from 251 | [DMSO-d$_6$] δ; 3.05–4.2(m, 5H), 5.29 5.48(brs, 1H), 8.17(d, J=12.4Hz, 1H), 9.01(s, 1H), 9.38(s, 1H) | Et$_3$N CH$_3$CN |
| 235 | H | O=(piperidinyl)N— | N | Pale yellow solid | 244–246 | [DMSO-d$_6$] δ; 2.45–2.55(m, 4H), 3.9–4.0(m, 4H), 8.21(d, J=13.2Hz, 1H), 9.02(s, 1H), 9.31(s, 1H) | Et$_3$N CH$_3$CN |
| 236 | H | HO–(pyrrolidinyl,NH)N— | N | Brown solid | Decomposed from 172 | [DMSO-d$_6$] δ; 2.98(s, 2H), 3.74(brs, 1H), 4.48(s, 1H), 5.9–6.2(m, 1H), 7.96(d, J=12.2Hz, 1H), 8.76(s, 1H), 9.49(s, 1H) | Et$_3$N CH$_3$CN |

TABLE 47

| Compound No. | R$^2$ | Y | Z | Property | Melting point (°C.) | $^1$H-NMR | Solvent |
|---|---|---|---|---|---|---|---|
| 237 | H | H$_2$N–(azetidinyl)N— | N | Yellow solid | Decomposed from 280 | [DMSO-d$_6$+ ] δ; 2.9–3.2(m, 3H), 3.7–4.4(m, 4H), 8.04(d, J=11.1Hz, 1H), 8.99(s, 1H), 9.31(s, 1H) | Et$_3$N CH$_3$CN |
| 238 | H | (Me)$_2$N–(azetidinyl)N— | N | Pale yellow solid | 217–220 | [DMSO-d$_6$] δ; 2.20(s, 6H), 2.4–2.7(m, 2H), 2.97(brs, 1H), 3.4–4.6(m, 4H), 8.0(d, J=11.1Hz, 1H), 8.97(s, 1H), 9.31(s, 1H) | Et$_3$N CH$_3$CN |
| 239 | H (CH$_3$)$_3$CN— | H | | N | Red solid | 251–254 | [CDCl$_3$] δ; 1.3(s, 9H), 5.51(brs, 1H), 8.04(d, J=10.7Hz, 1H), 8.86(s, 1H), 8.89(s, 1H) | Et$_3$N CH$_3$CN |

TABLE 48

Compound:

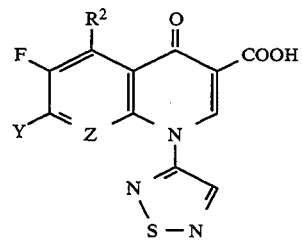

| Compound No. | R² | Y | Z | Property | Melting point (°C.) | ¹H-NMR | Solvent |
|---|---|---|---|---|---|---|---|
| 240 | Me | H₂N—[azetidine]—N— .HCl | C—H | Yellow solid | 257–259 | [DMSO-d₆] δ; 2.7(s, 3H), 3.67(brs, 2H), 3.8(brs, 1H), 4.21(brs, 2H), 5.79(d, J=6.8Hz, 1H), 8.81(s, 1H), 9.22(s, 1H) | Et₃N/CH₃CN ↓ AcOH, HClaq |
| 241 | Me | (Me)₂N—[azetidine]—N— .HCl | C—H | Colorless solid | 242–244.5 | [DMSO-d₆] δ; 2.71(s, 6H), 2.75(d, J=2.5Hz, 3H), 4.1–4.5(m, 5H), 5.98(d, J=7.7Hz, 1H), 8.86(s, 1H), 9.25(s, 1H) | " |
| 242 | Me | H₂N—CH₂—[azetidine]—N— | C—H | Pale yellow solid | Decomposed from 231 | [DMSO-d₆] δ; 2.7(s, 3H), 2.55–2.85(br, 3H), 3.78(brs, 2H), 4.06(brs, 2H), 5.77(d, J=8.1Hz, 1H), 8.78(s, 1H), 9.24(s, 1H) | Et₃N CH₃CN |
| 243 | Me | (Me)₂N—CH₂—[azetidine]—N— | C—H | Pale yellow solid | 221–224.5 | [DMSO-d₆] δ; 2.11(s, 6H), 2.4–2.6(m, 2H), 2.71(s, 3H), 2.75–2.9(br, 1H), 3.7(brs, 2H), 4.12(brs, 2H), 5.81(d, J=8.1Hz, 1H), 8.8(s, 1H), 9.23(s, 1H) | Et₃N CH₃CN |

TABLE 49

Compound:

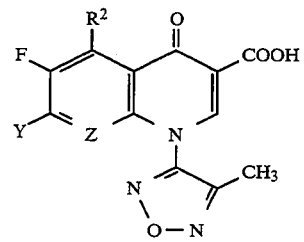

| Compound No. | R² | Y | Z | Property | Melting point (°C.) | ¹H-NMR | Solvent |
|---|---|---|---|---|---|---|---|
| 244 | H | H₂N—[piperidine]—N— .HCl | N | Pale yellow solid | 279–280.5 | [DMSO-d₆] δ; 1.45–1.7(m, 2H), 2.0–2.15(m, 2H), 2.31(s, 3H), 3.05–3.25(m, 2H), 4.1–4.25(m, 2H), 8.17(d, J=13.7Hz, 1H), 8.36(brs, 3H) 8.96(s, 1H) | Et₃N/CH₃CN ↓ AcOH, HClaq |
| 245 | H | H₂N—[azetidine]—N— | N | Colorless solid | 244–245 | [DMSO-d₆] δ; 2.32(s, 3H), 3.8–4.7(m, 3H), 8.04(d, J=11.1Hz, 1H), 8.86(s, 1H) | Et₃N CH₃CN |

EXAMPLE 156

7-{3-(S)-(2-(S)-t-Buthoxycarbonylaminopropionyl)aminopyrrolidin-1-yl}-6-fluoro-1-(4-methyl-1,2,5-oxadiazol-3-yl)-1,4-dihydro-4-oxo-1,8-naphthyridine-3-carboxylic acid (Compound No.246)

A solution of Boc-L-alanine (190 mg), 1-hydroxybenzotriazole (153 mg), WSC hydrochloride (192 mg) and triethylamine (101 mg) in chloroform (10 mg) was stirred at room temperature for 0.5 hour. To this solution was added a solution of compound No.81 (370 mg) in DMF (10 ml), then stirred at 50° C. for 1 day. After evaporation of the solvent, an aqueous 5% citric acid solution (20 ml) was added, then extracted with chloroform (100 ml). The organic phase was dried (MgSO4) and removed. After addition of isopropylether for solidification, the precipitate was filtrated. The title compound No. 246 was obtained as a yellow solid.

Melting point: 205.5°–207.5° C. $^1$H-NMR(CDCl$_3$) δ; 1.33(d,J=6.8 Hz,3H), 1.40(s,9H), 2.2(brs,2H), 2.35(s,3H), 4.1(brs,1H), 4.55(brs,1H), 5.03(brs,1H), 7.0–7.2(br,1H), 8.0(d,J=12 Hz,1H), 8.57(s,1H)

EXAMPLE 157

7-{3-(S)-(2-(S)-Aminopropionyl)aminopyrrolidin-1-yl}-6-fluoro-1-(4-methyl-1,2,5-oxadiazol-3-yl)-1,4-dihydro-4-oxo-1,8-naphthyridine-3-carboxylic acid hydrochloride (Compound No. 247)

Method a

Compound No.246 (90 mg) was dissolved in chloroform (10 ml) and 4N-HCl/dioxane (1 ml). The solution was stirred at room temperature for 20 minutes. After evaporation of the solvent, ether was added. The precipitate was filtrated. The title compound No. 247 was obtained as a yellow solid (80 mg).

Method b

Compound No.78 (2.1 g) synthesized in Example 39 and 3-(S)-aminopyrrolidine (0.86 g) was dissolved in chloroform (50 ml). The solution was stirred at room temperature for 10 hours. After evaporation of the solvent, ether was added to obtain a red solid (2.4 g).

To a solution of Boc-L-alanine (945 mg) and N-methylmorpholine (505 mg) in dichloromethane (20 ml), 0.65 ml of isobutylchloroformate was added with ice cooling. Then the solution was stirred for 20 minutes. To this solution was added the red solid (2.01 g) obtained above, then stirred at room temperature for 30 minutes. The reaction solution was washed with aqueous 5% citric acid, aqueous 5% NaHCO$_3$ and water successively. The organic phase was dried (MgSO$_4$) and evaporated. To the residue was added ether (20 ml). The precipitate was filtrated to obtain a pale red solid (2.5 g).

This compound is an ethyl ester derivative of compound No.244.

Melting point: 107°–113° C. $^1$H-NMR(CDCl$_3$) δ; 1.2–1.5(m,15H), 1.95–2.2(br,2H), 2.22(s,3H), 3.7–4.0(br,1H), 4.2–4.3(m,3H), 4.55–4.8(br,1H), 7.64(d,J=12 Hz,1H), 8.41(s,1H)

This red solid (1.5 g) was dissolved in tetrahydrofuran (30 ml) and 6N-HCl (5 ml). The solution was stirred at room temperature for 48 hours. After evaporation of the solvent, ethanol was added to the residue. The precipitate was filtrated. The title compound No. 247 was obtained as a yellow solid (0.98 g).

Melting point: 223.0°–225.0° C. $^1$H-NMR(DMSO-d$_6$) δ; 1.32(d,J=6.8 Hz,3H), 1.8–2.2(m,2H), 2.33(s,3H), 3.2–4.2(m,4H), 4.35(brs,1H), 8.08(d,J=12.4 Hz,1H), 8.26(brs,3H), 8.90(s,1H), 9.0(d,1H)

EXAMPLE 158

Compound Nos. 248–252 listed in Tables 50 and 51 were synthesized in a similar manner to Example 11, proceeding from the compound No.3.

TABLE 50

Compound:

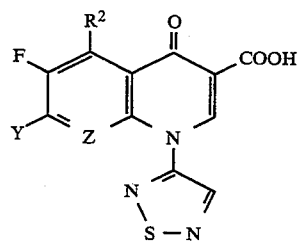

| Compound No. | R$^2$ | Y | Z | Property | Melting point (°C.) | $^1$H-NMR | Solvent |
|---|---|---|---|---|---|---|---|
| 248 | H | (piperidine with H$_2$N).HCl | N | Pale yellow solid | 258.5–259.5 | [DMSO-d$_6$] δ; 1.5–1.85(m, 3H), 1.99(brs, 1H), 3.2–3.55(m, 3H), 3.7–3.85(m, 1H), 4.05–4.2(m, 1H), 8.21(d, J=12.8Hz, 1H), 8.38(brs, 3H), 9.01(s, 1H), 9.33(s, 1H) | Et$_3$N/CH$_3$CN ↓ AcOH, HClaq |

TABLE 50-continued

Compound:

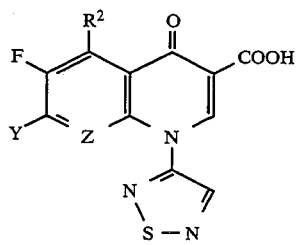

| Compound No. | R² | Y | Z | Property | Melting point (°C.) | ¹H-NMR | Solvent |
|---|---|---|---|---|---|---|---|
| 249 | H | (Me)₂N—◇—N— .HCl | N | Colorless solid | Decomposed from 272 | [DMSO-d₆] δ; 2.77(s, 6H), 4.2–4.8(m, 5H), 8.19(d, J=11.5Hz, 1H), 9.03(s, 1H), 9.33(s, 1H) | " |
| 250 | H | H₂N—◯—N— .HCl | N | Pale yellow solid | 247–250 | [DMSO-d₆] δ; 1.45–1.68(m, 2H), 1.9–2.1(m, 2H), 3.07–3.25(m, 2H), 4.1–4.3(m, 2H), 8.2(d, J=13Hz, 1H), 8.18(brs, 3H), 9.02(s, 1H), 9.28(s, 1H) | " |

TABLE 51

| Compound No. | R² | Y | Z | Property | Melting point (°C.) | ¹H-NMR | Solvent |
|---|---|---|---|---|---|---|---|
| 251 | H | [bicyclic NH structure] .HCl | N | Colorless powder | 214–216 (Decomposed) | [DMSO-d₆] δ; 1.60–1.85(m, 5H), 3.15–3.22(m, 1H), 3.51–4.15(m, 6H), 8.17(d, J=12.8Hz, 1H), 9.02(s, 1H), 9.30(brs, 1H) | Et₃N/CH₃CN ↓ AcOH, HClaq |
| 252 | H | (1S, 6S) [bicyclic NH structure] .HCl | N | Colorless powder | 215–218 (Decomposed) | [DMSO-d₆] δ; 1.60–1.85(m, 5H), 3.15–3.22(m, 1H), 3.51–4.15(m, 6H), 8.17(d, J=12.8Hz, 1H), 9.02(s, 1H), 9.30(brs, 1H) | " |

Now, synthetic methods of 3-amino-4-methyl-1,2,5-thiadiazol are described as reference examples:

Reference Example 1

4-Methyl-1,2,5-thiadiazol-3-carboxylic acid (Compound A)

To a mixture of sulfur monochloride (220 ml) and DMF (400 ml) was added 75 g of 2,3-diaminobutylic acid dihydrobromide with ice cooling, then stirred at room temperature for 2 hours. This solution was poured into water (3 liters), then extracted with ether (3L×4). The ether was removed in vacuo. The residue was dissolved in 5% aqueous NaHCO₃ solution (200 ml) and washed with 100 ml of carbondisulfide. After the solution was acidified with c-HCl it was extracted with ether (1.3L×2). The organic phase was dried (MgSO₄) and concentrated in vacuo. The title compound (A) was obtained as a pale yellow solid (7.5 g).

Melting point: 123°–129° C. ¹H-NMR(DMSO-d₆) δ; 2.72(s,3H)

Reference Example 2

3-t-Buthoxycarbonylamino-4-methyl-1,2,5-thiadiazole (Compound B)

A solution of compound A (7.5 g), triethylamine (5.8 g) and diphenylphosphorylazide (15.7 g) in 2-methyl-2-propanol (200 ml) was stirred for 20 hours under reflux with heating. The solvent was removed. After addition of ethyl acetate (500 ml), the solution was washed with water, 5% aqueous citric acid, and 5% aqueous NaHCO₃ successively, followed by drying (MgSO₄) and distillation. The residue was purified by column chromatography on silicagel(chloroform as an eluent). The title compound (B) was obtained as a colorless solid (10.4 g).

Melting point: 124°–128° C. ¹H-NMR(CDCl₃) δ; 1.53(s,9H), 2.50(s,3H), 7.1(brs,1H)

Reference Example 3

3-Amino-4-methyl-1,2,5-thiadiazole, hydrochloride (Compound C)

Compound B (15.2 g) was dissolved in ethanol (200 ml) and c-HCl (35 ml). The solution was stirred at 50° C. for 4 hours. After evaporation of the solvent, 100 ml of chloroform was added. The precipitate was filtrated. The title compound was obtained as a yellow solid (7.7 g).

Melting point: 121°–124° C. $^1$H-NMR(DMSO-d$_6$) δ; 2.31(s,3H), 7.55(brs,3H)

EXAMPLE 159

Antibacterial activity, absorption and excretion of the compounds indicated in Examples were tested as follows.

(1) Antibacterial activity

The minimum inhibitory concentration (MIC: microgram/ml) is measured by the standard method of Japan Society of Chemotherapy, (Chemotherapy, Volume 29, No.1, pp.76–79, 1981). The results are shown in Table 52 in which compound numbers are the same as those indicated in Examples.

TABLE 52

| Compound No. | Minimum Inhibitory Concentration (micro-g/ml) | | |
|---|---|---|---|
| | E. Coli NIH JC-2 (IFO* 12734) | S. aureus 209P (IFO 12732) | P. aeruginosa (IFO 3445) |
| 18 | <0.013 | 0.2 | 0.1 |
| 19 | <0.013 | 0.1 | 0.39 |
| 58 | 0.05 | 1.56 | 0.39 |
| 81 | 0.05 | 0.1 | 0.2 |
| 126 | 3.13 | 0.39 | 3.13 |
| 162 | 0.013 | 0.1 | 0.2 |
| 187 | 0.05 | 0.2 | 0.39 |

*Institute of Fermentation, Osaka

(2) Absorption and excretion

The absorption and excretion after oral administration of the compounds of the present invention were tested by measuring the recovery in urine and bile as follows.

(a) Recovery in urine

To a group of three male JCL-SD rats (6 weeks old) fasted overnight, a subject compound was orally administered as prepared to be 20 mg/10 ml/kg with 0.5% of methylcellulose solution. The sampling was carried out by collecting urine in 0 to 6 hours and 6 to 24 hours. The concentration of the subject compound in the urine was examined by a disk method by using Bacillus subtilis ATCC 6633 as a testing bacillus to obtain an excretion rate in urine for 24 hours.

(b) Recovery in bile

A subject compound was prepared in the same manner as the recovery test in urine and was orally administered to the rats. The bile was collected by using a polyethylene tube inserted into the choledochus over 24 hours. The concentration of the subject compound in the bile sample was examined in the same manner as the recovery in urine to obtain an excretion rate in bile for 24 hours.

The results are shown in Table 53.

TABLE 53

| Compound No. | Excretion Rate (24 hours, %) | |
|---|---|---|
| | In Urine | In Bile |
| 18 | 20 | 2 |

TABLE 53-continued

| Compound No. | Excretion Rate (24 hours, %) | |
|---|---|---|
| | In Urine | In Bile |
| 19 | 80.6 | 4.4 |

As described above, according to the present invention, the compounds represented by formula(1) and salts thereof, which are novel compounds, exhibit an extremely excellent antibacterial activity against gram-negative and gram-positive bacteria and possess a high oral absorbability.

Industrial Applicability

According to the present invention, the compounds represented by formula (1) and salts thereof are extremely valuable as antibacterial agents and very safe. Accordingly, they can be used as not only pharmaceuticals or medicines for the human body and animals but also medicines for fishes, agricultural chemicals and preservatives for foods. Further, the compounds of this invention are expected to have an anti viral action, especially an anti-HIV (human immuno deficiency virus) action, and therefore is considered to have preventive or curative activities against the AIDS.

We claim:

1. A quinolone derivative represented by the formula (1), or a salt thereof:

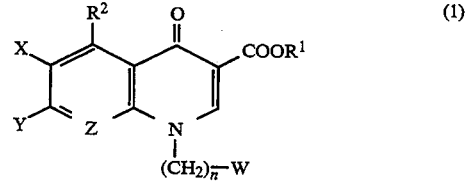

(1)

wherein $R^1$ represents a hydrogen atom, or a carboxyl protective group, $R^2$ represents a hydrogen atom, halogen atom or a lower alkyl group, X represents a hydrogen atom or a halogen atom, Y represents a halogen atom, a cyclic amino group having one or more nitrogen atoms as part of the ring and which group may have a substituent, a cyclo-lower alkenyl group which may have a substituent, or a group $R^3$-(CH$_2$)$_m$—A— (wherein $R^3$ represents a hydrogen atom or an amino group which may have a substituent, A represents an oxygen atom or a sulfur atom and m represents a number of 0 to 3), Z represents a nitrogen atom or a group C—$R^4$ (wherein $R^4$ represents a hydrogen atom or a halogen atom), W represents a five-membered heterocyclic group which may have a substituent and which has 3 or more hetero-atoms, among which at least 2 hetero-atoms are nitrogen atoms, and n represents a number of 0 to 2.

2. A quinolone derivative or a salt thereof according to claim 1, wherein said cyclic amino group represented by Y which may have a substituent is selected from the group consisting of saturated or unsaturated monocyclic 3 to 7 membered cyclic amino groups having one nitrogen atom, saturated or unsaturated monocyclic 3 to 7 membered cyclic amino groups having two nitrogen atoms, saturated or unsaturated monocyclic 3 to 7 membered cyclic amino groups having three or more nitrogen atoms, and saturated or unsaturated monocyclic 3 to 7 membered cyclic amino group further having a hetero-atom selected from the group consisting of oxygen and sulfur.

3. A quinolone derivative or a salt thereof according to claim 1, wherein said group represented by W is selected from the group consisting of thiadiazolyl group, triazolyl group, oxadiazolyl group and tetrazolyl group, each of which may have a substituent.

4. An antibacterial agent comprising the quinolone derivative or a salt thereof according to claim 1.

* * * * *

UNITED STATES PATENT AND TRADEMARK OFFICE
CERTIFICATE OF CORRECTION

PATENT NO.    : 5,412,098
DATED         : May 2, 1995
INVENTOR(S)   : Yasuhiro KURAMOTO, et al.

It is certified that error appears in the above-indentified patent and that said Letters Patent is hereby corrected as shown below:

On the title page, Item [75], the first and second inventors' names should read:

--Yasuhiro Kuramoto; Shuichiro Noda--

Also on the title page, Item [87], the PCT Publishing Date should read:

--Jul. 8, 1993--

Signed and Sealed this

Fourth Day of July, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,412,098
DATED        : May 2, 1995
INVENTOR(S)  : Yasuhiro KURAMOTO, et al.

It is certified that error appears in the above-indentified patent and that said Letters Patent is hereby corrected as shown below:

On the title page, Item [19], the first inventor's last name should read:

--Kuramoto et al.--

On the title page, Item [75], the first and second inventors' names should read:

--Yasuhiro Kuramoto; Shuichiro Noda--

On the title page, Item [87], the PCT Publishing Date should read:

--Jul. 8, 1993--

This certificate supersedes Certificate of Correction issued July 4, 1995.

Signed and Sealed this

Twenty-second Day of August, 1995

Attest:

BRUCE LEHMAN

Attesting Officer        Commissioner of Patents and Trademarks